(12) United States Patent
Konetzki et al.

(10) Patent No.: US 9,670,189 B2
(45) Date of Patent: Jun. 6, 2017

(54) SUBSTITUTED CONDENSED PYRIMIDINE COMPOUNDS

(71) Applicant: GRÜNENTHAL GMBH, Aachen (DE)

(72) Inventors: Ingo Konetzki, Aachen (DE); Florian Jakob, Aachen (DE); Tobias Craan, Aachen (DE); Christian Hesslinger, Zoznegg (DE); Paul Ratcliffe, Aachen (DE); Jason J. Shiers, Nottingham (GB)

(73) Assignee: GRÜNENTHAL GMBH, Aachen (DE)

( * ) Notice: Subject to any disclaimer, the term of this patent is extended or adjusted under 35 U.S.C. 154(b) by 0 days.

(21) Appl. No.: 14/817,630

(22) Filed: Aug. 4, 2015

(65) Prior Publication Data

US 2015/0344496 A1 Dec. 3, 2015

Related U.S. Application Data

(63) Continuation of application No. PCT/EP2014/000274, filed on Feb. 3, 2014.

(60) Provisional application No. 61/760,197, filed on Feb. 4, 2013.

(30) Foreign Application Priority Data

Feb. 4, 2013 (EP) .................... 13000550
May 3, 2013 (EP) .................... 13002373

(51) Int. Cl.
| | | |
|---|---|---|
| *A61K 31/519* | (2006.01) | |
| *C07D 495/04* | (2006.01) | |
| *C07D 409/04* | (2006.01) | |
| *C07D 417/04* | (2006.01) | |
| *C07D 239/70* | (2006.01) | |

(52) U.S. Cl.
CPC ......... *C07D 409/04* (2013.01); *C07D 239/70* (2013.01); *C07D 417/04* (2013.01); *C07D 495/04* (2013.01)

(58) Field of Classification Search
CPC ................................... C07D 495/04
See application file for complete search history.

(56) References Cited

U.S. PATENT DOCUMENTS

| | | |
|---|---|---|
| 5,712,298 A | 1/1998 | Amschler |
| 2006/0293343 A1 | 12/2006 | Naganuma et al. |
| 2011/0021501 A1 | 1/2011 | Pouzet et al. |

FOREIGN PATENT DOCUMENTS

| | | |
|---|---|---|
| WO | 95 01338 A1 | 1/1995 |
| WO | 2009 050248 A1 | 4/2009 |
| WO | 2012 054874 A1 | 4/2012 |

OTHER PUBLICATIONS

Schröter et al.; "Regioselective cross-coupling reactions of multiple halogenated nitrogen-, oxygen-, and sulfur-containing heterocycles"; Tetrahedron 61 (2005) pp. 2245-2267.
Han, et al.; "Recent development of peptide coupling reagents in organic synthesis"; Tetrahedron 60 (2004) pp. 2447-2467.
Bartrum, et al.; "An Approach to the Synthesis of anti-β2,3-Amino Acids: Application of β-Trifluoroacetamidoorganozinc Reagents"; Synlett, 2009, No. 14, pp. 2257-2260.
Schudt et al., "PDE Isoenzymes as Targets for Anti-Asthma Drugs"; European Respiratory Journal, 1995, vol. 8, pp. 1179-1183.
Mori, et al., "The human area postrema and other nuclei related to the emetic reflex express cAMP phosphodiesterases 4B and 4D"; Journal of Chemical Neuroanatomy, vol. 40, 2010, pp. 36-42.
Press, et al., "2 PDE4 Inhibitors—A review of the current field"; Progress in Medicinal Chemistry, vol. 47, 2009, pp. 37-74.
Robichaud, et al., "Deletion of phosphodiesterase 4D in mice shortens alpha2-adrenoceptor-mediated anesthesia, a behavioral correlate of emesis"; Journal of Clinical Investigation, vol. 110, No. 7, 2002, pp. 1045-1052.
Lee, et al., "Dynamic Regulation of Cystic Fibrosis Transmembrane Conductance Regulator by Competitive Interactions of Molecular Adaptors"; the Journal of Biological Chemistry, vol. 282, No. 14, Apr. 6, 2007, pp. 10414-10422.
Giembycz, "4D or not 4D—the emetogenic basis of PDE4 inhibitors uncovered?"; TRENDS in Pharmacological Sciences, vol. 23, No. 12, Dec. 2002, pp. 548.
Naganuma, et al., "Discovery of selective PDE4B inhibitors"; Bioorganic & Medicinal Chemistry Letters 19, 2009, pp. 3174-3176.
Goto et al., "Identification of the fused bicyclic 4-amino-2-phenylpyrimidine derivatives as novel and potent PDE4 inhibitors"; Bioorganic & Medicinal Chemistry Letters 23, 2013, pp. 3325-3328.
Hill, et al., "New Strategies for the Synthesis of Pyrimidine Derivatives"; Chemistry—A European Journal, vol. 14, 2008, pp. 6836-6844.
Bergmann; "Dehydration and Isomerization of Dimethylethynylcarbinol"; Journal of the Chimical Society, 1951, pp. 1218-1221.

(Continued)

*Primary Examiner* — Brian McDowell
(74) *Attorney, Agent, or Firm* — Norris McLaughlin & Marcus, P.A.

(57) ABSTRACT

The invention relates to novel substituted condensed pyrimidine compounds of general formula (I)

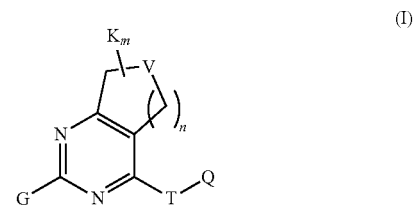

in which the chemical groupings, substituents and indices are as defined in the description, and to their use as medicaments, in particular as medicaments for the treatment of conditions and diseases that can be treated by inhibition of the PDE4 enzyme.

8 Claims, No Drawings

(56) References Cited

OTHER PUBLICATIONS

Kralijevic, et al., "Synthesis, X-ray crystal structure study and antitumoral evaluations of 5,6-disubstituted pyrimidine derivatives"; Bioorganic & Medicinal Chemistry, vol. 18, 2010, pp. 2704-2712.
Wuts et al., "Protection for the carboxyl group"; Green't Protective Groups in Organic Synthesis, Fourth Edition, 2007, pp. 538-616.
Saldou, et al.; "Comparison of Recombinant Human PDE4 Isoforms: Interaction with Substrate and Inhibitors"; Cell. Signal. vol. 10, No. 6, 1998, pp. 427-440.
"Remington's Pharmaceutical Sciences", Ed. A.R. Gennaro, 17th edition, Mack Publishing Company, Easton PA (1985), chapters 76.
"Remington's Pharmaceutical Sciences", Ed. A.R. Gennaro, 17th edition, Mack Publishing Company, Easton PA (1985), chapters 77.
"Remington's Pharmaceutical Sciences", Ed. A.R. Gennaro, 17th edition, Mack Publishing Company, Easton PA (1985), chapters 78.
"Remington's Pharmaceutical Sciences", Ed. A.R. Gennaro, 17th edition, Mack Publishing Company, Easton PA (1985), chapters 79.
"Remington's Pharmaceutical Sciences", Ed. A.R. Gennaro, 17th edition, Mack Publishing Company, Easton PA (1985), chapters 80.
"Remington's Pharmaceutical Sciences", Ed. A.R. Gennaro, 17th edition, Mack Publishing Company, Easton PA (1985), chapters 81.
"Remington's Pharmaceutical Sciences", Ed. A.R. Gennaro, 17th edition, Mack Publishing Company, Easton PA (1985), chapters 82.
"Remington's Pharmaceutical Sciences", Ed. A.R. Gennaro, 17th edition, Mack Publishing Company, Easton PA (1985), chapters 83.
"Remington's Pharmaceutical Sciences", Ed. A.R. Gennaro, 17th edition, Mack Publishing Company, Easton PA (1985), chapters 84.
"Remington's Pharmaceutical Sciences", Ed. A.R. Gennaro, 17th edition, Mack Publishing Company, Easton PA (1985), chapters 85.
"Remington's Pharmaceutical Sciences", Ed. A.R. Gennaro, 17th edition, Mack Publishing Company, Easton PA (1985), chapters 86.
"Remington's Pharmaceutical Sciences", Ed. A.R. Gennaro, 17th edition, Mack Publishing Company, Easton PA (1985), chapters 87.
"Remington's Pharmaceutical Sciences", Ed. A.R. Gennaro, 17th edition, Mack Publishing Company, Easton PA (1985), chapters 88.
"Remington's Pharmaceutical Sciences", Ed. A.R. Gennaro, 17th edition, Mack Publishing Company, Easton PA (1985), chapters 89.
"Remington's Pharmaceutical Sciences", Ed. A.R. Gennaro, 17th edition, Mack Publishing Company, Easton PA (1985), chapters 90.
"Remington's Pharmaceutical Sciences", Ed. A.R. Gennaro, 17th edition, Mack Publishing Company, Easton PA (1985), chapters 91.
"Remington's Pharmaceutical Sciences", Ed. A.R. Gennaro, 17th edition, Mack Publishing Company, Easton PA (1985), chapters 92.
"Remington's Pharmaceutical Sciences", Ed. A.R. Gennaro, 17th edition, Mack Publishing Company, Easton PA (1985), chapters 93.

SUBSTITUTED CONDENSED PYRIMIDINE COMPOUNDS

This application is a Continuation of International Application No. PCT/EP2014/000274, filed Feb. 3, 2014, which claims priority benefit under 35 U.S.C. §119(e) of U.S. Provisional Application No. 61/760,197, filed Feb. 4, 2013, and claims priority benefit under 35 U.S.C. §119(b) of European Application No. 13 000 550.7, filed Feb. 4, 2013, and European Application No. 13 002 373.2, filed May 3, 2013, the disclosures of which are incorporated herein by reference.

The present invention relates to novel substituted, condensed pyrimidine compounds and to their use as medicaments.

It is known that certain pyrimidine compounds are suitable for inhibiting specific phosphodiesterases (abbreviated as PDEs). Phosphodiesterases, or more accurately 3',5'-cyclonucleotide phosphodiesterases, are enzymes that catalyse the hydrolysis of the second messengers cAMP (cyclic adenosine monophosphate) and cGMP (cyclic guanosine monophosphate) to 5'-AMP (5'-adenosine monophosphate) and 5'-GMP (5'-guanosine monophosphate). Inhibition of phosphodiesterases thus represents a mechanism for modulating cellular processes and can be used to alleviate or cure disease conditions.

WO 95/01338 A1, for example, describes how suitable PDE inhibitors can be used to treat inflammatory respiratory diseases, dermatoses, and other proliferative, inflammatory and allergic skin diseases. WO 95/01338 A1 proposes, moreover, that such PDE inhibitors can find application in the treatment of diseases that are based on an excess release of TNF and leukotrienes, for example diseases from the arthritis spectrum (rheumatoid arthritis, rheumatoid spondylitis, osteoarthritis and other arthritic conditions). The international publication proposes, furthermore, the use of suitable PDE inhibitors as medicaments for diseases of the immune system (e.g. AIDS), symptoms of shock, as well as generalised inflammations in the gastrointestinal system (e.g. Crohn's disease and ulcerative colitis), diseases based on allergic and/or chronic, immunological adverse reactions in the upper respiratory tract (lateral pharyngeal space, nose) and adjacent regions (sinuses, eyes), such as for example allergic rhinitis/sinusitis, chronic rhinitis/sinusitis, allergic conjunctivitis and nasal polyps, but also diseases of the heart that can be treated by PDE inhibitors, such as for example heart failure, or diseases that can be treated because of the tissue-relaxing effect of PDE inhibitors, such as for example renal and ureteric colic in conjunction with kidney stones.

Phosphodiesterases are a group of enzymes encompassing 11 gene families (PDE1-11), which differ inter alia through their affinity to cAMP and cGMP.

The inhibition of the individual gene families with suitable substances is the subject of wide-ranging research. A known PDE5 inhibitor is sildenafil, which is commercially available under the trade name Viagra™ and which is used primarily for the treatment of erectile dysfunction.

The discovery that the second messenger cAMP plays an important role in many inflammatory processes and that PDE4 is strongly expressed in cells that control inflammation processes (see inter alia Schudt, C. et al. (1995). PDE isoenzymes as targets for anti-asthma drugs. *European Respiratory Journal* 8, 1179-1183), has led to the development of PDE4 inhibitors having an anti-inflammatory effect. One such PDE4 inhibitor having an anti-inflammatory effect is roflumilast for example (known under the trade name Daxas®), which was approved as a medicament for the treatment of COPD (chronic obstructive pulmonary disease). In addition to the desired anti-inflammatory effect of roflumilast, however, side-effects such as for example nausea, diarrhoea and headaches are observed, which limit the dose in humans.

Undesired side-effects in humans were observed with other PDE4 inhibitors too, so the therapeutic range (therapeutic window) of such medicaments is relatively narrow. The provision of PDE4 inhibitors having only little side-effects and a better therapeutic window would therefore be desirable.

Phosphodiesterase 4 (PDE4) is cAMP-specific and encompasses 4 different subtypes (PDE4A, PDE4B, PDE4C and PDE4D). As is described below, efforts are being made to find subtype-selective PDE4 inhibitors, above all PDE4B-selective inhibitors, that have less severe or no side-effects, such that the therapeutic range of these compounds is increased significantly.

The inhibition of PDE4D is associated with the occurrence of undesired side-effects, such as for example diarrhoea, vomiting and nausea (see in this regard Mori, F. et al. (2010). The human area postrema and other nuclei related to the emetic reflex express cAMP phosphodiesterases 4B and 4D. *Journal of Chemical Neuroanatomy* 40, 36-42; Press, N.J.; Banner K. H (2009). PDE4 inhibitors—A review of the current field. *Progress in Medicinal Chemistry* 47, 37-74; Robichaud, A. et al. (2002). Deletion of phosphodiesterase 4D in mice shortens α2-adrenoceptor-mediated anesthesia, a behavioral correlate of emesis. *The Journal of Clinical Investigation* 110, 1045-52; or Lee et al., (2007). Dynamic regulation of CFTR by competitive interactions of molecular adaptors. *Journal of Biological Chemistry* 282, 10414-10422); or Giembycz, M. A. (2002). 4D or not 4D—the emetogenic basis of PDE4 inhibitors uncovered? *Trends in Pharmacological Sciences* 23, 548).

In an article entitled "Discovery of selective PDE4B inhibitors" published in Bioorganic & Medicinal Chemistry Letters 19 (2009) p. 3174-3176, Kenji et al. disclose thirty-five pyrimidine compounds that exhibit PDE4B selectivity. Some of the compounds listed are said to show a 10-times higher inhibitory activity against PDE4B than against PDE4D.

The compounds examined by Kenji et al. are substantially encompassed by the general formula described in US 2006/0293343A1. US 2006/0293343A1 discloses specific pharmaceutically effective PDE4-inhibiting pyrimidine compounds having an anti-inflammatory effect, of the following general formula:

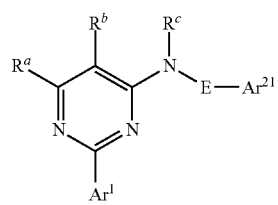

in which
Ar$^1$ is optionally substituted furyl, thienyl, triazolyl, thiazolyl, oxazolyl or benzothiazolyl;
E is a single bond or methylene;
Ar$^{21}$ is an optionally substituted phenyl or naphthyl;
R$^a$ and R$^b$ in each case independently of one another is hydrogen or alkyl, alkenyl, alkynyl, alkoxy, thioalkyl, alkyl sulfinyl, alkyl sulfonyl, each of which can optionally be substituted; and
R$^c$ is hydrogen or optionally substituted alkyl.

In the article by Kenji et al. the authors describe the examination of various structure-activity relationships, discussing inter alia the influence of the substituents at the 5- and 6-position on the pyrimidine ring (the substituent at the 5-position corresponds to $R^b$ in the general formula above, which was taken from US 2006/0293343A1, and the substituent at the 6-position corresponds to $R^a$). It can be inferred from the article that when an allyl, ethyl, cyano or formyl radical is bound at the 5-position of the pyrimidine ring, highly effective, selective PDE4B compounds were obtained. If, however, a larger chemical group is present at the same position, the inhibitory activity of the tested compounds decreases. With regard to possible modifications of the substituents at the 6-position of the pyrimidine ring, the authors ascertain that if methyl is replaced with ethyl at this position, the activity of the compound increases and the selectivity is lowered. Thus the authors reason that changes at the 5- and/or 6-position of the pyrimidine ring influence the activity and the selectivity of the pyrimidine compound. The authors allude to steric effects, without however giving any further information as to how the selectivity can be influenced without losing inhibitory activity.

In an unrevised article by Goto, T. et al. Bioorg. Med. Chem. Lett. (2013) entitled "Identification of the fused bicyclic 4-amino-2-phenylpyrimidine derivatives as novel and potent PDE4 inhibitors, which has been published online on Apr. 3, 2013, and which is now published in Bioorg. Med. Chem. Lett. 23 (2013) 3325-3328, several fused bicyclic compounds are described having a PDE4B inhibiting activity. Some compounds given in this article are represented by the following formula:

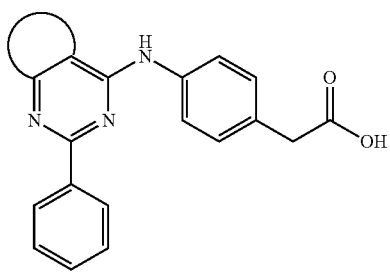 [SMILES: O=C(O)Cc1ccc(Nc2ccnc(-c3ccccc3)n2)cc1]

Based on the prior art the object of the present invention was to find compounds that are preferably PDE4B-selective (i.e. to find active compounds or compositions that with a particular amount of active ingredient inhibit PDE4B without inhibiting or only weakly inhibiting the PDE4D subtype). The advantage of such a PDE4B selectivity, as mentioned above, is that various side-effects do not occur or occur only to a small extent and that therefore a greater therapeutic range (=therapeutic window) of the pharmaceutical active ingredient is obtained. The therapeutic range of a pharmaceutical active ingredient or medicament describes the d between its therapeutic dose and a dose that would lead to a toxic or undesired effect. The greater the therapeutic range, the rarer or more unlikely the occurrence of certain toxic or undesired side-effects and hence the safer and more tolerable the pharmaceutical active ingredient or medicament. The therapeutic range is often also referred to as the therapeutic window or therapeutic index. These names are used synonymously in the present application.

The inventors have now found pyrimidine compounds that display the desired inhibiting and PDE4B-selective property and are superior to the corresponding pyrimidine compounds of the prior art. They are therefore particularly suitable for the treatment of diseases and conditions in which inhibition of the PDE4 enzyme, in particular the PDE4B enzyme, is advantageous.

The invention thus relates to pyrimidine compounds of the following general formula (I)

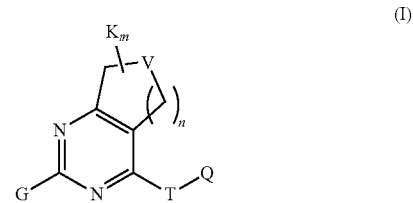

in which

G is a phenyl optionally substituted with at least one substituent Z or a 5- or 6-membered heteroaromatic ring optionally substituted with at least one substituent Z; G preferably is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z; or G preferably stands for one of the following optionally substituted groups G1 to G34

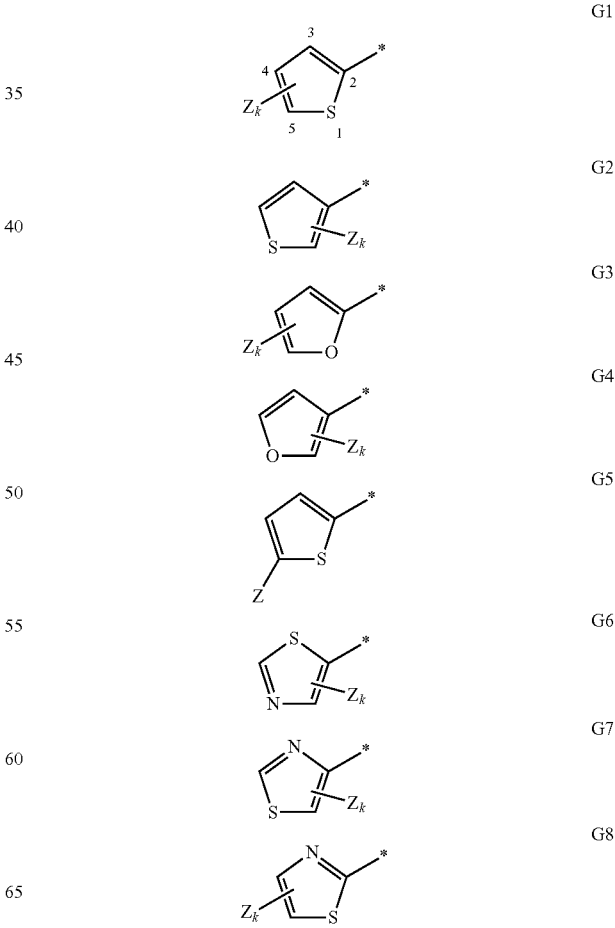

in which the site marked with an asterisk (*) indicates the binding site at position 2 of the pyrimidine ring;

G particularly preferably is selected from G1, G2, G3, G4, G5, G6, G7, G8, G9, G10, G11, G12, G13, G14, G15, G16, G17 and G34; G most particularly preferably is selected from G1, G2, G5, G6, G7, G8, G12, G13 and G34;

Z independently of one another is $(C_1\text{-}C_6)$ alkyl, $(C_1\text{-}C_6)$ hydroxyalkyl, $(C_1\text{-}C_6)$ alkoxy, $(C_1\text{-}C_6)$ haloalkyl, $(C_1\text{-}C_6)$ haloalkoxy, S($C_1$-$C_6$) alkyl, halogen, OH or CN, as well as S(O)($C_1$-$C_6$) alkyl, S(O)$_2$($C_1$-$C_6$) alkyl, CO—NH$_2$, CO—NH($C_1$-$C_6$) alkyl, or CO—N(($C_1$-$C_6$) alkyl)$_2$, wherein aforementioned alkyls are branched or straight-chain and can be substituted; Z preferably independently of one another is CH$_3$, OCH$_3$, CF$_3$, CHF$_2$, CH$_2$F, OCF$_3$, OCHF$_2$, OCH$_2$F, SCH$_3$, Cl, F, OH and CN, as well as Br, CONH$_2$ and SO$_2$CH$_3$;

V is CH$_2$ or a group S(O)$_x$ with x being 0, 1 or 2 (i.e. S, SO or SO$_2$), whereas one or two hydrogen atoms in the CH$_2$ group can be replaced by the same or a different substituent K;

k is 0, 1, 2, 3 or 4; k preferably is 0 or 1, or is 0, 1 or 2; or is 1, 2, 3, 4;

T is oxygen, CH$_2$, CHR$^1$ or CR$^1$R$^2$;

R$^1$ and R$^2$ independently of one another is ($C_1$-$C_8$) alkyl (preferably ($C_1$-$C_6$) or ($C_1$-$C_4$) alkyl), ($C_1$-$C_8$) hydroxyalkyl (preferably ($C_1$-$C_6$) or ($C_1$-$C_4$) hydroxyalkyl), ($C_1$-$C_8$) haloalkyl (preferably ($C_1$-$C_6$) or ($C_1$-$C_4$) haloalkyl; in particular CHF$_2$, CH$_2$F or CF$_3$) and ($C_1$-$C_8$) hydroxyhaloalkyl (preferably ($C_1$-$C_6$) or ($C_1$-$C_4$) hydroxyhaloalkyl), wherein the aforementioned alkyl chains are branched or straight-chain and can be substituted, or R$^1$ and R$^2$, together with the carbon atom to which they are bound, form a saturated 3- to 6-membered ring consisting of hydrocarbon groups (carbocycle), optionally substituted with branched or straight-chain ($C_1$-$C_6$) alkyl or hydroxyl groups, which can optionally have one or more heteroatoms (e.g. O, S, N) (heterocycle);

Q is a phenyl, pyrimidyl, pyrazinyl or pyridyl substituted with a substituent X$^1$ and optionally substituted with at least one substituent X, in which X$^1$ is preferably bound in para-position; Q is preferably selected from the following groups Q1 to Q13, in which the site marked with an asterisk indicates the binding site at group T;

p is 0, 1, 2, 3 or 4 and L has the meaning given below; p preferably is 0 or 1;

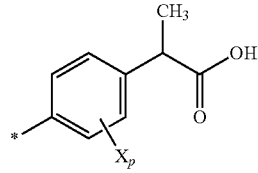
Q1

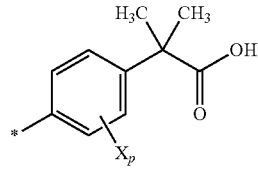
Q2

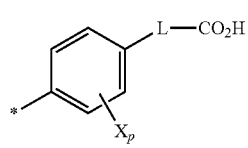
Q3

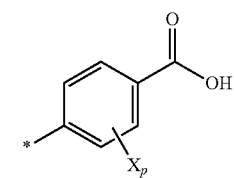
Q4

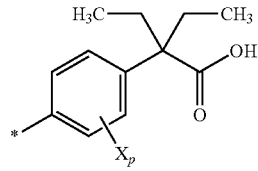
Q5

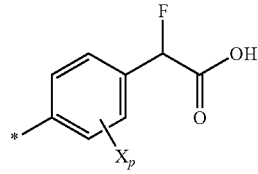
Q6

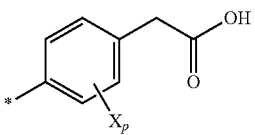
Q7

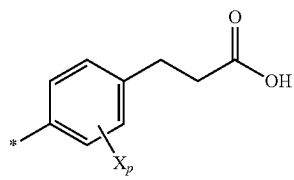
Q8

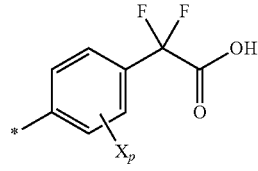
Q9

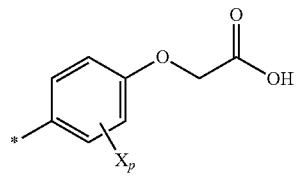
Q10

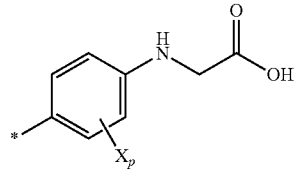
Q11

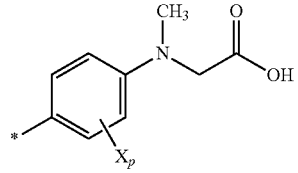
Q12

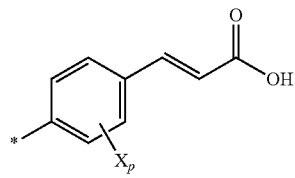
Q13

Q particularly preferably is selected from Q2, Q3, Q8 or Q9; most particularly preferably is sleeted from Q2 or Q3;

$X^1$ is an L-CO$_2$R$^3$ group;

X independently of one another is (C$_1$-C$_6$) alkyl, (C$_3$-C$_6$) cycloalkyl, (C$_1$-C$_6$) alkoxy, (C$_3$-C$_6$) cycloalkoxy, (C$_1$-C$_6$) haloalkyl, (C$_1$-C$_6$) haloalkoxy, halogen, hydroxyl, cyano, carboxyl, —NH$_2$, —NH(C$_1$-C$_6$) alkyl, —N((C$_1$-C$_6$) alkyl)$_2$, N-pyrrolidinyl, N-piperidinyl, N-morpholinyl, —NH—C(O)—(C$_1$-C$_6$) alkyl, —C(O)—NH$_2$, —C(O)—NH(C$_1$-C$_6$) alkyl, —C(O)—N((C$_1$-C$_6$) alkyl)$_2$, —S(O)$_2$—NH$_2$, —S(C$_1$-C$_6$) alkyl, —S(O)—(C$_1$-C$_6$) alkyl, or —S(O)$_2$—(C$_1$-C$_6$) alkyl, wherein the aforementioned alkyl chains are branched or straight-chain and can be substituted;

R$^3$ is hydrogen, branched or straight-chain (C$_1$-C$_6$) alkyl, preferably (C$_1$-C$_4$) alkyl;

L is a bond, (C$_1$-C$_6$) alkylene, (C$_2$-C$_6$) alkenylene, —O—(C$_1$-C$_4$) alkylene, —NH—(C$_1$-C$_4$) alkylene, or —NR$^3$—(C$_1$-C$_4$) alkylene, wherein aforementioned alkylenes or alkenylenes can each be substituted with one or more halogen atoms (in particular fluorine) or wherein aforementioned alkylenes or alkenylenes can be substituted with one or more (C$_1$-C$_6$) alkyl groups (preferably methyl or ethyl), or wherein in aforementioned alkylenes or alkenylenes a CH$_2$ unit can be replaced by an oxygen atom;

L preferably stands for a bond or methylene, wherein the methylene can be substituted with one or two halogen atoms (in particular fluorine);

n is 1 or 2;

K is (C$_1$-C$_6$) alkyl, preferably (C$_1$-C$_4$) alkyl, (C$_1$-C$_6$) alkoxy, preferably (C$_1$-C$_4$) alkoxy, (C$_1$-C$_6$) haloalkyl, preferably (C$_1$-C$_4$) haloalkyl, halogen, hydroxyl or cyano; and m is 0, 1, 2, 3 or 4, as well as pharmacologically tolerable salts, diastereomers, enantiomers, racemates, hydrates or solvates thereof.

The invention relates in an [embodiment A] to pyrimidine compounds of the following general formula (XX)

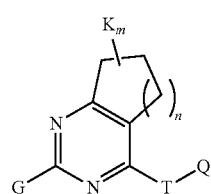
(XX)

in which

G is a phenyl optionally substituted with at least one substituent Z or a 5- or 6-membered heteroaromatic ring optionally substituted with at least one substituent Z; G preferably stands for one of the following optionally substituted groups G1 to G34

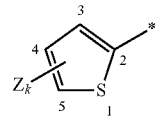
G1

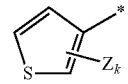
G2

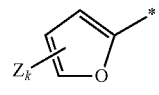
G3

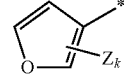
G4

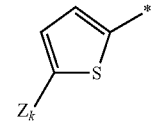
G5

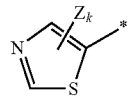
G6

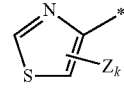
G7

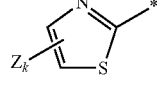
G8

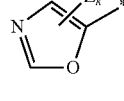
G9

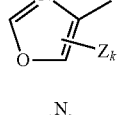
G10

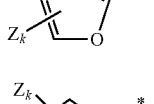
G11

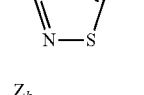
G12

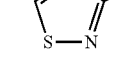
G13

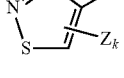
G14 in which the site marked with an asterisk (*) indicates the binding site at position 2 of the pyrimidine ring;

G particularly preferably is selected from G1, G2, G3, G4, G5, G6, G7, G8, G9, G10, G11, G12, G13, G14, G15, G16, G17 and G34; G most particularly preferably is selected from G1, G2, G5, G6, G7, G8, G12, G13 and G34;

Z independently of one another is $(C_1$-$C_6)$ alkyl, $(C_1$-$C_6)$ hydroxyalkyl, $(C_1$-$C_6)$ alkoxy, $(C_1$-$C_6)$ haloalkyl, $(C_1$-$C_6)$ haloalkoxy, —S$(C_1$-$C_6)$ alkyl, halogen, hydroxyl or cyano, wherein aforementioned alkyls are branched or straight-chain and can be substituted; Z preferably independently of one another is $CH_3$, $OCH_3$, $CF_3$, $CHF_2$, $CH_2F$, $OCF_3$, $OCHF_2$, $OCH_2F$, $SCH_3$, Cl, F, OH or CN;

k is 0, 1, 2; k preferably is 0 or 1;

T is oxygen, $CH_2$, $CHR^1$ or $CR^1R^2$;

$R^1$ and $R^2$ independently of one another is $(C_1$-$C_8)$ alkyl (preferably $(C_1$-$C_6)$ or $(C_1$-$C_4)$ alkyl), $(C_1$-$C_8)$ hydroxyalkyl (preferably $(C_1$-$C_6)$ or $(C_1$-$C_4)$ hydroxyalkyl), $(C_1$-$C_8)$ haloalkyl (preferably $(C_1$-$C_6)$ or $(C_1$-$C_4)$ haloalkyl; in particular $CHF_2$, $CH_2F$ or $CF_3$) and $(C_1$-$C_8)$ hydroxyhaloalkyl (preferably $(C_1$-$C_6)$ or $(C_1$-$C_4)$ hydroxyhaloalkyl), wherein the aforementioned alkyl chains are branched or straight-chain and can be substituted, or $R^1$ and $R^2$, together with the carbon atom to which they are bound, form a saturated 3- to 6-membered ring consisting of hydrocarbon groups (carbocycle), optionally substituted with branched or straight-chain $(C_1$-$C_6)$ alkyl or hydroxyl groups, which can optionally have one or more heteroatoms (e.g. O, S, N) (heterocycle);

Q is a phenyl, pyrimidyl, pyrazinyl or pyridyl substituted with a substituent $X^1$ and optionally substituted with at least one substituent X, in which $X^1$ is preferably bound in para-position; Q is preferably selected from the following groups Q1 to Q13, in which the site marked with an asterisk indicates the binding site at group T;

p is 0, 1, 2, 3 or 4 and L has the meaning given below; p preferably is 0 or 1;

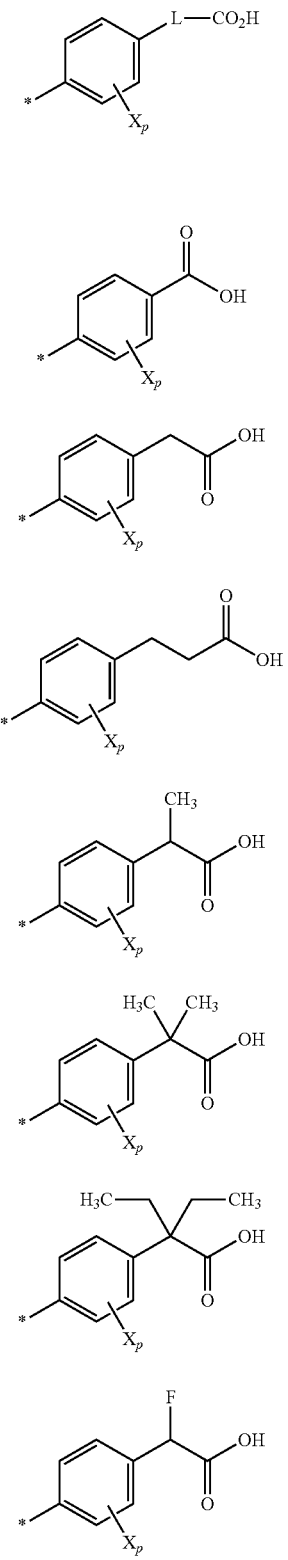

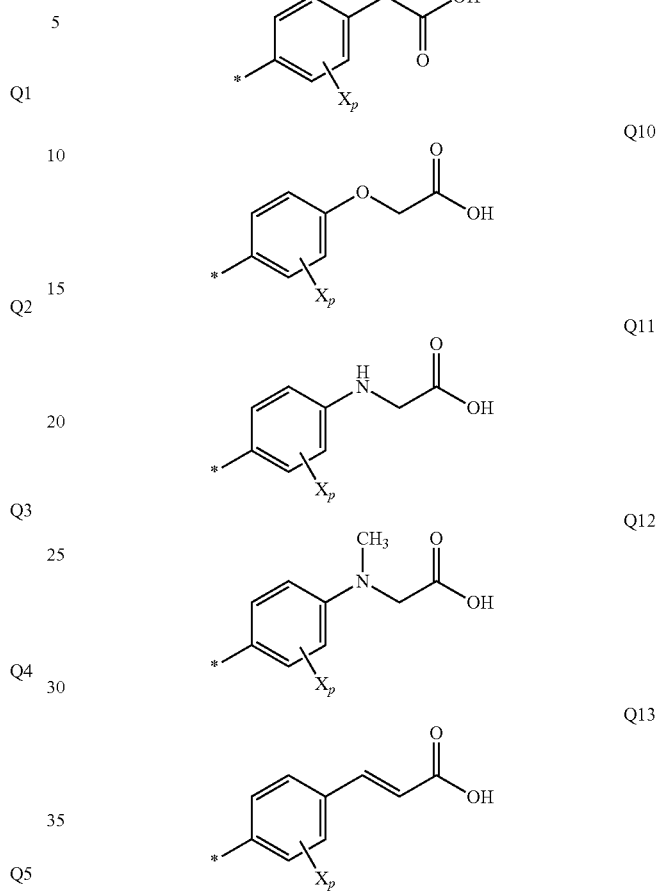

Q particularly preferably is selected from Q2, Q3, Q8 or Q9; most particularly preferably is sleeted from Q2 or Q3;

$X^1$ is an $L\text{-}CO_2R^3$ group;

X independently of one another is $(C_1\text{-}C_6)$ alkyl, $(C_3\text{-}C_6)$ cycloalkyl, $(C_1\text{-}C_6)$ alkoxy, $(C_3\text{-}C_6)$ cycloalkoxy, $(C_1\text{-}C_6)$ haloalkyl, $(C_1\text{-}C_6)$ haloalkoxy, halogen, hydroxyl, cyano, carboxyl, $-NH_2$, $-NH(C_1\text{-}C_6)$ alkyl, $-N((C_1\text{-}C_6)$ alkyl$)_2$, N-pyrrolidinyl, N-piperidinyl, N-morpholinyl, $-NH-C(O)-(C_1\text{-}C_6)$ alkyl, $-C(O)-NH_2$, $-C(O)-NH(C_1\text{-}C_6)$ alkyl, $-C(O)-N((C_1\text{-}C_6)$ alkyl$)_2$, $-S(O)_2-NH_2$, $-S(C_1\text{-}C_6)$ alkyl, $-S(O)-(C_1\text{-}C_6)$ alkyl, or $-S(O)_2-(C_1\text{-}C_6)$ alkyl, wherein the aforementioned alkyl chains are branched or straight-chain and can be substituted;

$R^3$ is hydrogen, branched or straight-chain $(C_1\text{-}C_6)$ alkyl, preferably $(C_1\text{-}C_4)$ alkyl;

L is a bond, $(C_1\text{-}C_6)$ alkylene, $(C_2\text{-}C_6)$ alkenylene, $-O-(C_1\text{-}C_4)$ alkylene, $-NH-(C_1\text{-}C_4)$ alkylene, or $-NR^3-(C_1\text{-}C_4)$ alkylene, wherein aforementioned alkylenes or alkenylenes can each be substituted with one or more halogen atoms (in particular fluorine) or wherein aforementioned alkylenes or alkenylenes can be substituted with one or more $(C_1\text{-}C_6)$ alkyl groups (preferably methyl or ethyl), or wherein in aforementioned alkylenes or alkenylenes a $CH_2$ unit can be replaced by an oxygen atom;

L preferably stands for a bond or methylene, wherein the methylene can be substituted with one or two halogen atoms (in particular fluorine);

n is 1 or 2;

K is (C$_1$-C$_6$) alkyl, preferably (C$_1$-C$_4$) alkyl, (C$_1$-C$_6$) alkoxy, preferably (C$_1$-C$_4$) alkoxy, (C$_1$-C$_6$) haloalkyl, preferably (C$_1$-C$_4$) haloalkyl, halogen, hydroxyl or cyano; and m is 0, 1, 2, 3 or 4, as well as pharmacologically tolerable salts, diastereomers, enantiomers, racemates, hydrates or solvates thereof.

In an [embodiment AA] the invention relates to pyrimidine compounds of general formula (XX-A)

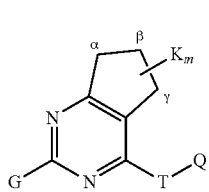

(XX-A)

wherein in general formula (XX-A) T is oxygen or methylene (CH$_2$) and the chemical groupings G and Q and the substituent K have the definitions described in connection with general formula (XX) and wherein m is 0, 1 or 2, m preferably denoting 0 or 1. Preferred pyrimidine compounds of formula (XX-A) are those in which Q is Q1, Q2 or Q3 and G is a chemical grouping G1, G2, G5, G6, G7, G8, G12, G13, G14 or G34 or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z.

In an [embodiment AB] the invention relates to pyrimidine compounds of general formula (XX-B)

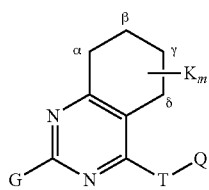

(XX-B)

wherein in general formula (XX-B) T is oxygen or methylene (CH$_2$), the chemical groupings G and Q and the substituent K have the definitions described in connection with general formula (XX) and wherein m is 0, 1 or 2, m preferably denoting 0 or 1. Preferred pyrimidine compounds of formula (XX-B) are those in which Q is Q1, Q2 or Q3 and G is a chemical grouping G1, G2, G5, G6, G7, G8, G12, G13, G14 or G34 or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z In an [embodiment AC] the invention relates to pyrimidine compounds of general formula (XX-C)

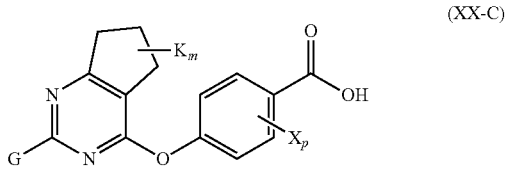

(XX-C)

wherein in general formula (XX-C) the chemical grouping G and the substituents K and X as well as the index p have the definitions described in connection with general formula (XX) and wherein m is 0, 1 or 2, m preferably denoting 0 or 1. Preferred pyrimidine compounds of formula (XX-C) are those in which G is a chemical grouping G1, G2, G5, G6, G7, G8, G12, G13, G14 or G34 or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z.

In an [embodiment AC-a] the invention relates to the compounds of [embodiment AC], in which G is G1.

In an [embodiment AC-b] the invention relates to the compounds of [embodiment AC], in which G is G2.

In an [embodiment AC-c] the invention relates to the compounds of [embodiment AC], in which G is G5.

In an [embodiment AC-d] the invention relates to the compounds of [embodiment AC], in which G is G6.

In an [embodiment AC-e] the invention relates to the compounds of [embodiment AC], in which G is G7.

In an [embodiment AC-f] the invention relates to compounds of [embodiment AC], in which G is G8.

In an [embodiment AC-g] the invention relates to the compounds of [embodiment AC], in which G is G12.

In an [embodiment AC-h] the invention relates to the compounds of [embodiment AC], in which G is G13.

In an [embodiment AC-i] the invention relates to the compounds of [embodiment AC], in which G is G14.

In an [embodiment AC-j] the invention relates to the compounds of [embodiment AC], in which G is G34.

In an [embodiment AD] the invention relates to the compounds of general formula (XX-D)

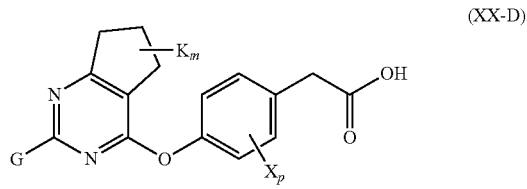

(XX-D)

wherein in general formula (XX-D) the chemical grouping G and the substituents K and X as well as the index p have the definitions described in connection with general formula (XX) and wherein m is 0, 1 or 2, m preferably denoting 0 or 1. Preferred pyrimidine compounds of formula (XX-D) are those in which G is a chemical grouping G1, G2, G5, G6, G7, G8, G12, G13, G14 or G34 or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z.

In an [embodiment AD-a] the invention relates to the compounds of [embodiment AD], in which G is G1.

In an [embodiment AD-b] the invention relates to the compounds of [embodiment AD], in which G is G2.

In an [embodiment AD-c] the invention relates to the compounds of [embodiment AD], in which G is G5.

In an [embodiment AD-d] the invention relates to the compounds of [embodiment AD], in which G is G6.

In an [embodiment AD-e] the invention relates to the compounds of [embodiment AD], in which G is G7.

In an [embodiment AD-f] the invention relates to the compounds of [embodiment AD], in which G is G8.

In an [embodiment AD-g] the invention relates to the compounds of [embodiment AD], in which G is G12.

In an [embodiment AD-h] the invention relates to the compounds of [embodiment AD], in which G is G13.

In an [embodiment AD-i] the invention relates to the compounds of [embodiment AD], in which G is G14.

In an [embodiment AD-j] the invention relates to the compounds of [embodiment AD], in which G is G34.

In an [embodiment AE] the invention relates to the compounds of general formula (XX-E)

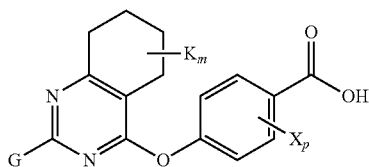

(XX-E)

wherein in general formula (XX-E) the chemical grouping G and the substituents K and X as well as the index p have the definitions described in connection with general formula (XX) and wherein m is 0, 1 or 2, m preferably denoting 0 or 1. Preferred pyrimidine compounds of formula (XX-E) are those in which G is a chemical grouping G1, G2, G5, G6, G7, G8, G12, G13, G14 or G34 or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z.

In an [embodiment AE-a] the invention relates to the compounds of [embodiment AE], in which G is G1.

In an [embodiment AE-b] the invention relates to the compounds of [embodiment AE], in which G is G2.

In an [embodiment AE-c] the invention relates to the compounds of [embodiment AE], in which G is G5.

In an [embodiment AE-d] the invention relates to the compounds of [embodiment AE], in which G is G6.

In an [embodiment AE-e] the invention relates to the compounds of [embodiment AE], in which G is G7.

In an [embodiment AE-f] the invention relates to the compounds of [embodiment AE], in which G is G8.

In an [embodiment AE-g] the invention relates to the compounds of [embodiment AE], in which G is G12.

In an [embodiment AE-h] the invention relates to the compounds of [embodiment AE], in which G is G13.

In an [embodiment AE-i] the invention relates to the compounds of [embodiment AE], in which G is G14.

In an [embodiment AE-j] the invention relates to the compounds of [embodiment AE], in which G is G34.

In an [embodiment AF] the invention relates to the compounds of general formula (XX-F)

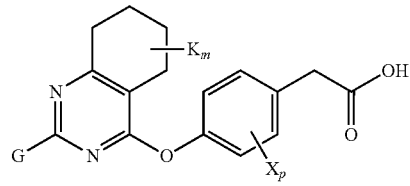

(XX-F)

wherein in general formula (XX-F) the chemical grouping G and the substituents K and X as well as the index p have the definitions described in connection with general formula (XX) and wherein m is 0, 1 or 2, m preferably denoting 0 or 1. Preferred pyrimidine compounds of formula (XX-F) are those in which G is a chemical grouping G1, G2, G5, G6, G7, G8, G12, G13, G14 or G34 or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z.

In an [embodiment AF-a] the invention relates to the compounds of [embodiment AF], in which G is G1.

In an [embodiment AF-b] the invention relates to the compounds of [embodiment AF], in which G is G2.

In an [embodiment AF-c] the invention relates to compounds of [embodiment AF], in which G is G5.

In an [embodiment AF-d] the invention relates to the compounds of [embodiment AF], in which G is G6.

In an [embodiment AF-e] the invention relates to the compounds of [embodiment AF], in which G is G7.

In an [embodiment AF-f] the invention relates to the compounds of [embodiment AF], in which G is G8.

In an [embodiment AF-g] the invention relates to the compounds of [embodiment AF], in which G is G12.

In an [embodiment AF-h] the invention relates to the compounds of [embodiment AF], in which G is G13.

In an [embodiment AF-i] the invention relates to the compounds of [embodiment AF], in which G is G14.

In an [embodiment AF-j] the invention relates to the compounds of [embodiment AF], in which G is G34.

In an [embodiment AG] the invention relates to the compounds of general formula (XX-G)

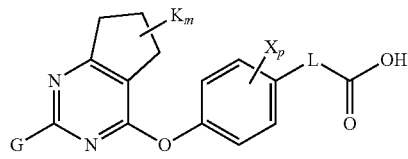

(XX-G)

wherein in general formula (XX-G) the chemical groupings G and L and the substituents K and X as well as the index p have the definitions described in connection with general formula (XX) and wherein m is 0, 1 or 2, m preferably denoting 0 or 1. Preferred pyrimidine compounds of formula (XX-G) are those in which G is a chemical grouping G1, G2, G5, G6, G7, G8, G12, G13, G14 or G34 or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z.

In an [embodiment AG-a] the invention relates to the compounds of [embodiment AG], in which G is G1.

In an [embodiment AG-b] the invention relates to the compounds of [embodiment AG], in which G is G2.

In an [embodiment AG-c] the invention relates to the compounds of [embodiment AG], in which G is G5.

In an [embodiment AG-d] the invention relates to the compounds of [embodiment AG], in which G is G6.

In an [embodiment AG-e] the invention relates to the compounds of [embodiment AG], in which G is G7.

In an [embodiment AG-f] the invention relates to the compounds of [embodiment AG], in which G is G8.

In an [embodiment AG-g] the invention relates to the compounds of [embodiment AG], in which G is G12.

In an [embodiment AG-h] the invention relates to the compounds of [embodiment AG], in which G is G13.

In an [embodiment AG-i] the invention relates to the compounds of [embodiment AG], in which G is G14.

In an [embodiment AG-j] the invention relates to the compounds of [embodiment AG], in which G is G34.

In an [embodiment AH] the invention relates to compounds of general formula (XX-H)

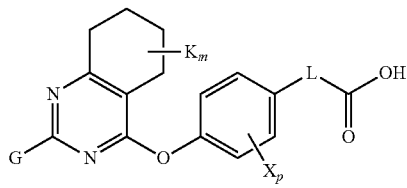

(XX-H)

wherein in general formula (XX-H) the chemical groupings G and L and the substituents K and X as well as the index p have the definitions described in connection with general formula (XX) and wherein m is 0, 1 or 2, m preferably denoting 0 or 1. Preferred pyrimidine compounds of formula (XX-H) are those in which G is a chemical grouping G1, G2, G5, G6, G7, G8, G12, G13, G14 or G34 or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z.

In an [embodiment AH-a] the invention relates to the compounds of [embodiment AH], in which G is G1.

In an [embodiment AH-b] the invention relates to the compounds of [embodiment AH], in which G is G2.

In an [embodiment AH-c] the invention relates to the compounds of [embodiment AH], in which G is G5.

In an [embodiment AH-d] the invention relates to the compounds of [embodiment AH], in which G is G6.

In an [embodiment AH-e] the invention relates to the compounds of [embodiment AH], in which G is G7.

In an [embodiment AH-f] the invention relates to the compounds of [embodiment AH], in which G is G8.

In an [embodiment AH-g] the invention relates to the compounds of [embodiment AH], in which G is G12.

In an [embodiment AH-h] the invention relates to the compounds of [embodiment AH], in which G is G13.

In an [embodiment AH-i] the invention relates to the compounds of [embodiment AH], in which G is G14.

In an [embodiment AH-j] the invention relates to the compounds of [embodiment AH], in which G is G34.

In an [embodiment AJ] the invention relates to the compounds of general formula (XX-J)

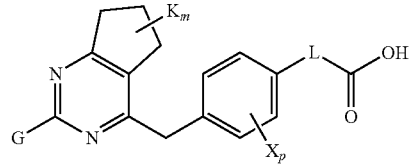

(XX-J)

wherein in general formula (XX-J) the chemical groupings G and L and the substituents K and X as well as the index p have the definitions described in connection with general formula (XX) and wherein m is 0, 1 or 2, m preferably denoting 0 or 1. Preferred pyrimidine compounds of formula (XX-J) are those in which G is a chemical grouping G1, G2, G5, G6, G7, G8, G12, G13, G14 or G34 or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z.

In an [embodiment AJ-a] the invention relates to the compounds of [embodiment AJ], in which G is G1.

In an [embodiment AJ-b] the invention relates to the compounds of [embodiment AJ], in which G is G2.

In an [embodiment AJ-c] the invention relates to the compounds of [embodiment AJ], in which G is G5.

In an [embodiment AJ-d] the invention relates to the compounds of [embodiment AJ], in which G is G6.

In an [embodiment AJ-e] the invention relates to the compounds of [embodiment AJ], in which G is G7.

In an [embodiment AJ-f] the invention relates to the compounds of [embodiment AJ], in which G is G8.

In an [embodiment AJ-g] the invention relates to the compounds of [embodiment AJ], in which G is G12.

In an [embodiment AJ-h] the invention relates to the compounds of [embodiment AJ], in which G is G13.

In an [embodiment AJ-i] the invention relates to the compounds of [embodiment AJ], in which G is G14.

In an [embodiment AJ-j] the invention relates to the compounds of [embodiment AJ], in which G is G34.

In an [embodiment AK] the invention relates to pyrimidine compounds of general formula (XX-K)

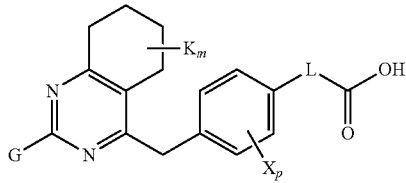

(XX-K)

wherein in general formula (XX-K) the chemical groupings G and L and the substituents K and X as well as the index p have the definitions described in connection with general formula (XX) and wherein m is 0, 1 or 2, m preferably denoting 0 or 1. Preferred pyrimidine compounds of formula (XX-K) are those in which G is a chemical grouping G1, G2, G5, G6, G7, G8, G12, G13, G14 or G34 or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z.

In an [embodiment AK-a] the invention relates to the compounds of [embodiment AK], in which G is G1.

In an [embodiment AK-b] the invention relates to the compounds of [embodiment AK], in which G is G2.

In an [embodiment AK-c] the invention relates to the compounds of [embodiment AK], in which G is G5.

In an [embodiment AK-d] the invention relates to the compounds of [embodiment AK], in which G is G6.

In an [embodiment AK-e] the invention relates to the compounds of [embodiment AK], in which G is G7.

In an [embodiment AK-f] the invention relates to the compounds of [embodiment AK], in which G is G8.

In an [embodiment AK-g] the invention relates to the compounds of [embodiment AK], in which G is G12.

In an [embodiment AK-h] the invention relates to the compounds of [embodiment AK], in which G is G13.

In an [embodiment AK-i] the invention relates to the compounds of [embodiment AK], in which G is G14.

In an [embodiment AK-j] the invention relates to the compounds of [embodiment AK], in which G is G34.

In an [embodiment AL] the invention relates to pyrimidine compounds of general formula (XX-L)

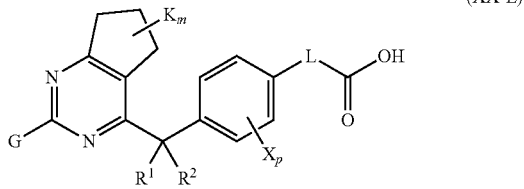

(XX-L)

wherein in general formula (XX-L) the chemical groupings G and L and the substituents $R^1$, $R^2$, K and X as well as the index p have the definitions described in connection with general formula (XX) and wherein m is 0, 1 or 2, m preferably denoting 0 or 1. Preferred pyrimidine compounds of formula (XX-L) are those in which G is a chemical grouping G1, G2, G5, G6, G7, G8, G12, G13, G14 or G34 or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z.

In an [embodiment AL-a] the invention relates to the compounds of [embodiment AL], in which G is G1.

In an [embodiment AL-b] the invention relates to the compounds of [embodiment AL], in which G is G2.

In an [embodiment AL-c] the invention relates to the compounds of [embodiment AL], in which G is G5.

In an [embodiment AL-d] the invention relates to the compounds of [embodiment AL], in which G is G6.

In an [embodiment AL-e] the invention relates to the compounds of [embodiment AL], in which G is G7.

In an [embodiment AL-f] the invention relates to the compounds of [embodiment AL], in which G is G8.

In an [embodiment AL-g] the invention relates to the compounds of [embodiment AL], in which G is G12.

In an [embodiment AL-h] the invention relates to the compounds of [embodiment AL], in which G is G13.

In an [embodiment AL-i] the invention relates to the compounds of [embodiment AL], in which G is G14.

In an [embodiment AL-j] the invention relates to the compounds of [embodiment AL], in which G is G34.

In an [embodiment AM] the invention relates to pyrimidine compounds of general formula (XX-M)

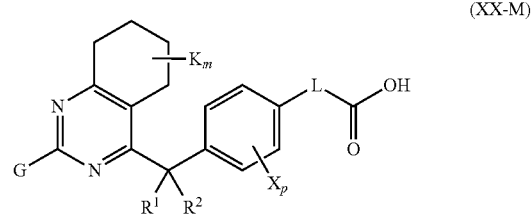

(XX-M)

wherein in general formula (XX-M) the chemical groupings G and L and the substituents $R^1$, $R^2$, K and X as well as the index p have the definitions described in connection with general formula (XX) and wherein m is 0, 1 or 2, m preferably denoting 0 or 1. Preferred pyrimidine compounds of formula (XX-M) are those in which G is a chemical grouping G1, G2, G5, G6, G7, G8, G12, G13, G14 or G34 or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z.

In an [embodiment AM-a] the invention relates to the compounds of [embodiment AM], in which G is G1.

In an [embodiment AM-b] the invention relates to the compounds of [embodiment AM], in which G is G2.

In an [embodiment AM-c] the invention relates to the compounds of [embodiment AM], in which G is G5.

In an [embodiment AM-d] the invention relates to the compounds of [embodiment AM], in which G is G6.

In an [embodiment AM-e] the invention relates to the compounds of [embodiment AM], in which G is G7.

In an [embodiment AM-f] the invention relates to the compounds of [embodiment AM], in which G is G8.

In an [embodiment AM-g] the invention relates to the compounds of [embodiment AM], in which G is G12.

In an [embodiment AM-h] the invention relates to the compounds of [embodiment AM], in which G is G13.

In an [embodiment AM-i] the invention relates to the compounds of [embodiment AM], in which G is G14.

In an [embodiment AM-j] the invention relates to the compounds of [embodiment AM], in which G is G34.

In an [embodiment AN] the invention relates to pyrimidine compounds of general formula (XX-N)

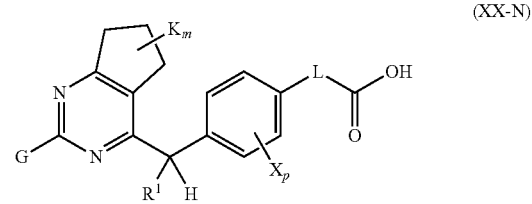

(XX-N)

wherein in general formula (XX-N) the chemical groupings G and L and the substituents $R^1$, K and X as well as the index p have the definitions described in connection with general formula (XX) and wherein m is 0, 1 or 2, m preferably denoting 0 or 1. Preferred pyrimidine compounds of formula (XX-N) are those in which G is a chemical grouping G1, G2, G5, G6, G7, G8, G12, G13, G14 or G34 or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z.

In an [embodiment AN-a] the invention relates to the compounds of [embodiment AN], in which G is G1.

In an [embodiment AN-b] the invention relates to the compounds of [embodiment AN], in which G is G2.

In an [embodiment AN-c] the invention relates to the compounds of [embodiment AN], in which G is G5.

In an [embodiment AN-d] the invention relates to the compounds of [embodiment AN], in which G is G6.

In an [embodiment AN-e] the invention relates to the compounds of [embodiment AN], in which G is G7.

In an [embodiment AN-f] the invention relates to the compounds of [embodiment AN], in which G is G8.

In an [embodiment AN-g] the invention relates to the compounds of [embodiment AN], in which G is G12.

In an [embodiment AN-h] the invention relates to the compounds of [embodiment AN], in which G is G13.

In an [embodiment AN-i] the invention relates to the compounds of [embodiment AN], in which G is G14.

In an [embodiment AN-j] the invention relates to the compounds of [embodiment AN], in which G is G34.

In an [embodiment AO] the invention relates to pyrimidine compounds of general formula (XX-O)

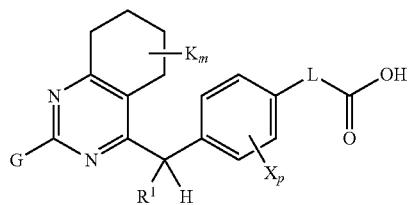

(XX-O)

wherein in general formula (XX-O) the chemical groupings G and L and the substituents $R^1$, K and X as well as the index p have the definitions described in connection with general formula (XX) and wherein m is 0, 1 or 2, m preferably denoting 0 or 1. Preferred pyrimidine compounds of formula (XX-O) are those in which G is a chemical grouping G1, G2, G5, G6, G7, G8, G12, G13, G14 or G34 or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z.

In an [embodiment AO-a] the invention relates to the compounds of [embodiment AO], in which G is G1.

In an [embodiment AO-b] the invention relates to the compounds of [embodiment AO], in which G is G2.

In an [embodiment AO-c] the invention relates to the compounds of [embodiment AO], in which G is G5.

In an [embodiment AO-d] the invention relates to the compounds of [embodiment AO], in which G is G6.

In an [embodiment AO-e] the invention relates to the compounds of [embodiment AO], in which G is G7.

In an [embodiment AO-f] the invention relates to the compounds of [embodiment AO], in which G is G8.

In an [embodiment AO-g] the invention relates to the compounds of [embodiment AO], in which G is G12.

In an [embodiment AO-h] the invention relates to the compounds of [embodiment AO], in which G is G13.

In an [embodiment AO-i] the invention relates to the compounds of [embodiment AO], in which G is G14.

In an [embodiment AO-j] the invention relates to the compounds of [embodiment AO], in which G is G34.

The invention relates in an [embodiment B] to pyrimidine compounds of the following general formula (XXI)

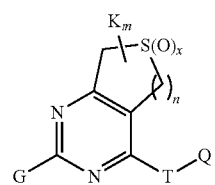

(XXI)

in which all chemical groups, substituents and indices have the definitions described in connection with the compounds of formula (I). Compounds are preferred wherein x is 2 or wherein x is 1.

In an [embodiment BA] the invention relates to pyrimidine compounds of general formula (XXI-A)

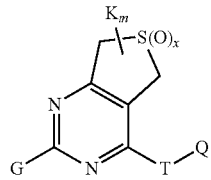

(XXI-A)

wherein in general formula (XXI-A) T is oxygen or methylene ($CH_2$) and the chemical groupings G and Q and the substituent K have the definitions described in connection with general formula (I) and wherein m is 0, 1 or 2, m preferably denoting 0 or 1. Preferred pyrimidine compounds of formula (XXI-A) are those in which Q is Q1, Q2 or Q3 and G is a chemical grouping G1, G2, G5, G6, G7, G8, G12, G13, G14 or G34, or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z, and wherein x is 2 or wherein x is 1.

In an [embodiment BB] the invention relates to pyrimidine compounds of general formula (XXI-B)

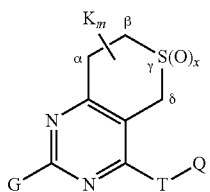

(XXI-B)

wherein in general formula (XXI-B) T is oxygen or methylene ($CH_2$), the chemical groupings G and Q and the substituent K have the definitions described in connection with general formula (I) and wherein m is 0, 1 or 2, m preferably denoting 0 or 1. Preferred pyrimidine compounds of formula (XXI-B) are those in which Q is Q1, Q2 or Q3 and G is a chemical grouping G1, G2, G5, G6, G7, G8, G12, G13, G14 or G34, or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z, and wherein x is 2 or wherein x is 1.

In an [embodiment BC] the invention relates to pyrimidine compounds of general formula (XXI-C)

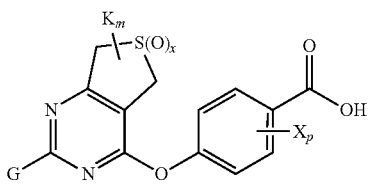

(XXI-C)

wherein in general formula (XXI-C) the chemical grouping G and the substituents K and X as well as the index p have the definitions described in connection with general formula (I) and wherein m is 0, 1 or 2, m preferably denoting 0 or 1. Preferred pyrimidine compounds of formula (XXI-C) are those in which G is a chemical grouping G1, G2, G5, G6, G7, G8, G12, G13, G14 or G34, or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z, and wherein x is 2 or wherein x is 1.

In an [embodiment BC-a] the invention relates to the compounds of [embodiment BC], in which G is G1.

In an [embodiment BC-b] the invention relates to the compounds of [embodiment BC], in which G is G2.

In an [embodiment BC-c] the invention relates to the compounds of [embodiment BC], in which G is G5.

In an [embodiment BC-d] the invention relates to the compounds of [embodiment BC], in which G is G6.

In an [embodiment BC-e] the invention relates to the compounds of [embodiment BC], in which G is G7.

In an [embodiment BC-f] the invention relates to the compounds of [embodiment BC], in which G is G8.

In an [embodiment BC-g] the invention relates to the compounds of [embodiment BC], in which G is G12.

In an [embodiment BC-h] the invention relates to the compounds of [embodiment BC], in which G is G13.

In an [embodiment BC-i] the invention relates to the compounds of [embodiment BC], in which G is G14.

In an [embodiment BC-j] the invention relates to the compounds of [embodiment BC], in which G is G34.

In an [embodiment BD] the invention relates to pyrimidine compounds of general formula (XXI-D)

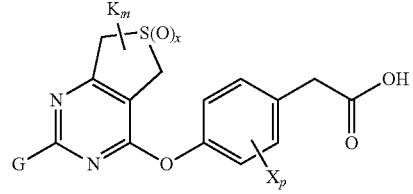

(XXI-D)

wherein in general formula (XXI-D) the chemical grouping G and the substituents K and X as well as the index p have the definitions described in connection with general formula (I) and wherein m is 0, 1 or 2, m preferably denoting 0 or 1. Preferred pyrimidine compounds of formula (XXI-D) are those in which G is a chemical grouping G1, G2, G5, G6, G7, G8, G12, G13, G14 or G34, or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z, and wherein x is 2 or wherein x is 1.

In an [embodiment BD-a] the invention relates to the compounds of [embodiment BD], in which G is G1.

In an [embodiment BD-b] the invention relates to the compounds of [embodiment BD], in which G is G2.

In an [embodiment BD-c] the invention relates to the compounds of [embodiment BD], in which G is G5.

In an [embodiment BD-d] the invention relates to the compounds of [embodiment BD], in which G is G6.

In an [embodiment BD-e] the invention relates to the compounds of [embodiment BD], in which G is G7.

In an [embodiment BD-f] the invention relates to the compounds of [embodiment BD], in which G is G8.

In an [embodiment BD-g] the invention relates to the compounds of [embodiment BD], in which G is G12.

In an [embodiment BD-h] the invention relates to the compounds of [embodiment BD], in which G is G13.

In an [embodiment BD-i] the invention relates to the compounds of [embodiment BD], in which G is G14.

In an [embodiment BD-j] the invention relates to the compounds of [embodiment BD], in which G is G34.

In an [embodiment BE] the invention relates to pyrimidine compounds of general formula (XXI-E)

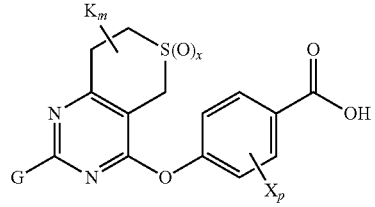

(XXI-E)

wherein in general formula (XXI-E) the chemical grouping G and the substituents K and X as well as the index p have the definitions described in connection with general formula (I) and wherein m is 0, 1 or 2, m preferably denoting 0 or 1. Preferred pyrimidine compounds of formula (XXI-E) are those in which G is a chemical grouping G1, G2, G5, G6, G7, G8, G12, G13, G14 or G34, or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z, and wherein x is 2 or wherein x is 1.

In an [embodiment BE-a] the invention relates to the compounds of [embodiment BE], in which G is G1.

In an [embodiment BE-b] the invention relates to the compounds of [embodiment BE], in which G is G2.

In an [embodiment BE-c] the invention relates to the compounds of [embodiment BE], in which G is G5.

In an [embodiment BE-d] the invention relates to the compounds of [embodiment BE], in which G is G6.

In an [embodiment BE-e] the invention relates to the compounds of [embodiment BE], in which G is G7.

In an [embodiment BE-f] the invention relates to the compounds of [embodiment BE], in which G is G8.

In an [embodiment BE-g] the invention relates to the compounds of [embodiment BE], in which G is G12.

In an [embodiment BE-h] the invention relates to the compounds of [embodiment BE], in which G is G13.

In an [embodiment BE-i] the invention relates to the compounds of [embodiment BE], in which G is G14.

In an [embodiment BE-j] the invention relates to the compounds of [embodiment BE], in which G is G34.

In an [embodiment BF] the invention relates to pyrimidine compounds of general formula (XXI-F)

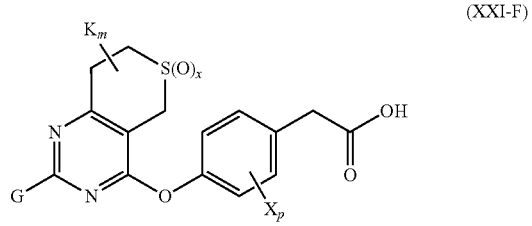

(XXI-F)

wherein in general formula (XXI-F) the chemical grouping G and the substituents K and X as well as the index p have the definitions described in connection with general formula (I) and wherein m is 0, 1 or 2, m preferably denoting 0 or 1. Preferred pyrimidine compounds of formula (XXI-F) are those in which G is a chemical grouping G1, G2, G5, G6, G7, G8, G12, G13, G14 or G34, or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z, and wherein x is 2 or wherein x is 1.

In an [embodiment BF-a] the invention relates to the compounds of [embodiment BF], in which G is G1.

In an [embodiment BF-b] the invention relates to the compounds of [embodiment BF], in which G is G2.

In an [embodiment BF-c] the invention relates to the compounds of [embodiment BF], in which G is G5.

In an [embodiment BF-d] the invention relates to the compounds of [embodiment BF], in which G is G6.

In an [embodiment BF-e] the invention relates to the compounds of [embodiment BF], in which G is G7.

In an [embodiment BF-f] the invention relates to the compounds of [embodiment BF], in which G is G8.

In an [embodiment BF-g] the invention relates to the compounds of [embodiment BF], in which G is G12.

In an [embodiment BF-h] the invention relates to the compounds of [embodiment BF], in which G is G13.

In an [embodiment BF-i] the invention relates to the compounds of [embodiment BF], in which G is G14.

In an [embodiment BF-j] the invention relates to the compounds of [embodiment BF], in which G is G34.

In an [embodiment BG] the invention relates to pyrimidine compounds of general formula (XXI-G)

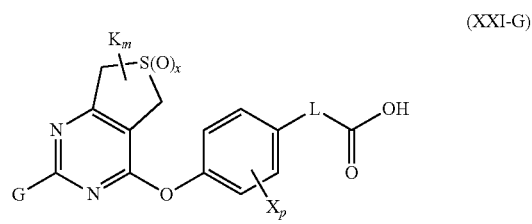

(XXI-G)

wherein in general formula (XXI-G) the chemical groupings G and L and the substituents K and X as well as the index p have the definitions described in connection with general formula (I) and wherein m is 0, 1 or 2, m preferably denoting 0 or 1. Preferred pyrimidine compounds of formula (XXI-G) are those in which G is a chemical grouping G1, G2, G5, G6, G7, G8, G12, G13, G14 or G34, or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z, and wherein x is 2 or wherein x is 1.

In an [embodiment BG-a] the invention relates to the compounds of [embodiment BG], in which G is G1.

In an [embodiment BG-b] the invention relates to the compounds of [embodiment BG], in which G is G2.

In an [embodiment BG-c] the invention relates to the compounds of [embodiment BG], in which G is G5.

In an [embodiment BG-d] the invention relates to the compounds of [embodiment BG], in which G is G6.

In an [embodiment BG-e] the invention relates to the compounds of [embodiment BG], in which G is G7.

In an [embodiment BG-f] the invention relates to the compounds of [embodiment BG], in which G is G8.

In an [embodiment BG-g] the invention relates to the compounds of [embodiment BG], in which G is G12.

In an [embodiment BG-h] the invention relates to the compounds of [embodiment BG], in which G is G13.

In an [embodiment BG-i] the invention relates to the compounds of [embodiment BG], in which G is G14.

In an [embodiment BG-j] the invention relates to the compounds of [embodiment BG], in which G is G34.

In an [embodiment BH] the invention relates to pyrimidine compounds of general formula (XXI-H)

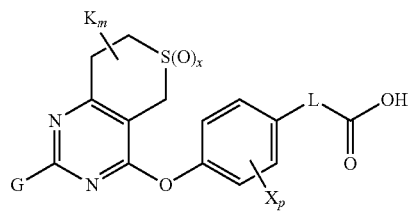

(XXI-H)

wherein in general formula (XXI-H) the chemical groupings G and L and the substituents K and X as well as the index p have the definitions described in connection with general formula (I) and wherein m is 0, 1 or 2, m preferably denoting 0 or 1. Preferred pyrimidine compounds of formula (XXI-H) are those in which G is a chemical grouping G1, G2, G5, G6, G7, G8, G12, G13, G14 or G34, or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z, and wherein x is 2 or wherein x is 1.

In an [embodiment BH-a] the invention relates to the compounds of [embodiment BH], in which G is G1.
In an [embodiment BH-b] the invention relates to the compounds of [embodiment BH], in which G is G2.
In an [embodiment BH-c] the invention relates to the compounds of [embodiment BH], in which G is G5.
In an [embodiment BH-d] the invention relates to the compounds of [embodiment BH], in which G is G6.
In an [embodiment BH-e] the invention relates to the compounds of [embodiment BH], in which G is G7.
In an [embodiment BH-f] the invention relates to the compounds of [embodiment BH], in which G is G8.
In an [embodiment BH-g] the invention relates to the compounds of [embodiment BH], in which G is G12.
In an [embodiment BH-h] the invention relates to the compounds of [embodiment BH], in which G is G13.
In an [embodiment BH-i] the invention relates to the compounds of [embodiment BH], in which G is G14.
In an [embodiment BH-j] the invention relates to the compounds of [embodiment BH], in which G is G34.

In an [embodiment BJ] the invention relates to pyrimidine compounds of general formula (XXI-J)

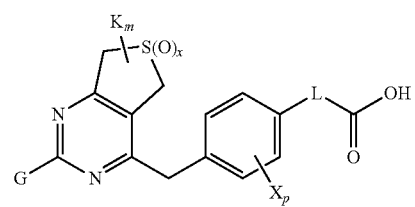

(XXI-J)

wherein in general formula (XXI-J) the chemical groupings G and L and the substituents K and X as well as the index p have the definitions described in connection with general formula (I) and wherein m is 0, 1 or 2, m preferably denoting 0 or 1. Preferred pyrimidine compounds of formula (XXI-J) are those in which G is a chemical grouping G1, G2, G5, G6, G7, G8, G12, G13, G14 or G34, or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z, and wherein x is 2 or wherein x is 1.

In an [embodiment BJ-a] the invention relates to the compounds of [embodiment BJ], in which G is G1.
In an [embodiment BJ-b] the invention relates to the compounds of [embodiment BJ], in which G is G2.
In an [embodiment BJ-c] the invention relates to the compounds of [embodiment BJ], in which G is G5.
In an [embodiment BJ-d] the invention relates to the compounds of [embodiment BJ], in which G is G6.
In an [embodiment BJ-e] the invention relates to the compounds of [embodiment BJ], in which G is G7.
In an [embodiment BJ-f] the invention relates to the compounds of [embodiment BJ], in which G is G8.
In an [embodiment BJ-g] the invention relates to the compounds of [embodiment BJ], in which G is G12.
In an [embodiment BJ-h] the invention relates to the compounds of [embodiment BJ], in which G is G13.
In an [embodiment BJ-i] the invention relates to the compounds of [embodiment BJ], in which G is G14.
In an [embodiment BJ-j] the invention relates to the compounds of [embodiment BJ], in which G is G34.

In an [embodiment BK] the invention relates to pyrimidine compounds of general formula (XXI-K)

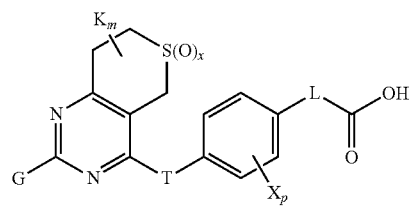

(XXI-K)

wherein in general formula (XXI-K) the chemical groupings G and L and the substituents K and X as well as the index p have the definitions described in connection with general formula (I) and wherein m is 0, 1 or 2, m preferably denoting 0 or 1. Preferred pyrimidine compounds of formula (XXI-K) are those in which G is a chemical grouping G1, G2, G5, G6, G7, G8, G12, G13, G14 or G34, or G is a phenyl optionally substituted with at least one substituent (preferably one, two or three substituents) Z, a thiazolyl optionally substituted with at least one substituent (preferably one or two substituents) Z or a thienyl optionally substituted with at least one substituent (preferably one or two substituents) Z, and wherein x is 2 or wherein x is 1.

In an [embodiment BK-a] the invention relates to the compounds of [embodiment BK], in which G is G1.
In an [embodiment BK-b] the invention relates to the compounds of [embodiment BK], in which G is G2.
In an [embodiment BK-c] the invention relates to the compounds of [embodiment BK], in which G is G5.
In an [embodiment BK-d] the invention relates to the compounds of [embodiment BK], in which G is G6.
In an [embodiment BK-e] the invention relates to the compounds of [embodiment BK], in which G is G7.
In an [embodiment BK-f] the invention relates to the compounds of [embodiment BK], in which G is G8.
In an [embodiment BK-g] the invention relates to the compounds of [embodiment BK], in which G is G12.
In an [embodiment BK-h] the invention relates to the compounds of [embodiment BK], in which G is G13.

In an [embodiment BK-i] the invention relates to the compounds of [embodiment BK], in which G is G14.

In an [embodiment BK-j] the invention relates to the compounds of [embodiment BK], in which G is G34.

In an [embodiment C] the invention relates to the compounds of formula (I) as defined herein characterised in that G is selected from the chemical groupings G1, G2, G3, G4, G5, G6, G7, G8, G9, G10, G11, G12, G13, G14, G15, G16, G17 and G34, as defined in claim 7, optionally substituted with at least one substituent Z; and Q is a chemical grouping Q2, Q3, Q8 or Q9, as defined in claim 7

Unless otherwise specified, the term ($C_1$-$C_6$) alkyl is understood to mean branched and unbranched alkyl groups consisting of 1 to 6 hydrocarbon atoms. Examples of ($C_1$-$C_6$) alkyl radicals are methyl, ethyl, n-propyl, 1-methylethyl (isopropyl), n-butyl, 1-methylpropyl, 2-methylpropyl, 1,1-dimethylethyl (tert-butyl), n-pentyl, 1-methylbutyl, 2-methylbutyl, 3-methylbutyl, 1,1-dimethylpropyl, 1,2-dimethylpropyl, 2,2-dimethylpropyl, n-hexyl, 1-methylpentyl, 2-methylpentyl, 3-methylpentyl, 4-methylpentyl. ($C_1$-$C_4$) alkyl radicals are preferred, ($C_1$-$C_3$) alkyl radicals being particularly preferred, in particular methyl, ethyl and propyl. Unless otherwise stated, the definitions of propyl, butyl, pentyl and hexyl encompass all possible isomeric forms of the individual radicals.

Unless otherwise specified, a haloalkyl radical is understood to be an alkyl radical in which at least one hydrogen is exchanged for a halogen atom, preferably fluorine, chlorine, bromine, particularly preferably fluorine. The haloalkyl radicals can be branched or unbranched and optionally mono- or polysubstituted. Preferred haloalkyl radicals are $CHF_2$, $CH_2F$, $CF_3$, $CH_2$—$CH_2F$, $CH_2$—$CHF_2$, $CH_2CF_3$. ($C_1$-$C_6$) haloalkyl radicals are preferred, with ($C_1$-$C_4$) haloalkyl radicals being particularly preferred and ($C_1$-$C_3$) haloalkyl radicals most particularly preferred, in particular $CHF_2$, $CH_2F$, $CF_3$, $CH_2$—$CH_2F$, $CH_2$—$CHF_2$ and $CH_2CF_3$.

Unless otherwise specified, a haloalkoxy radical is understood to be an alkoxy radical in which at least one hydrogen is exchanged for a halogen atom, preferably fluorine, chlorine, bromine, particularly preferably fluorine. The haloalkoxy radicals can be branched or unbranched and optionally mono- or polysubstituted. Preferred haloalkoxy radicals are $OCHF_2$, $OCH_2F$, $OCF_3$, $OCH_2$—$CFH_2$, $OCH_2$—$CF_2H$, $OCH_2CF_3$. ($C_1$-$C_6$) haloalkoxy radicals are preferred, with ($C_1$-$C_4$) haloalkoxy radicals being particularly preferred and ($C_1$-$C_3$) haloalkoxy radicals most particularly preferred, in particular $OCHF_2$, $OCH_2F$, $OCF_3$, $OCH_2$—$CFH_2$, $OCH_2$—$CF_2H$, $OCH_2CF_3$.

Unless otherwise specified, the term ($C_2$-$C_6$) alkenyl is understood to mean branched and unbranched alkyl groups consisting of 2 to 6 hydrocarbon atoms and having at least one double bond. Examples of ($C_2$-$C_6$) alkenyls are ethenyl (also referred to as vinyl), prop-1-enyl, prop-2-enyl (also referred to as allyl), but-1-enyl, but-2-enyl, but-3-enyl, pent-1-enyl and hex-1-enyl. The designation ($C_2$-$C_6$) alkenyl includes all possible isomers, i.e. structural isomers (constitutional isomers) and stereoisomers ((Z) and (E) isomers).

Unless otherwise specified, the term carbocycle is understood to mean preferably 3- to 7-membered rings consisting of hydrocarbon groups, which rings can be saturated or unsaturated.

Unless otherwise specified, the term heterocycle is understood to mean preferably 5- to 7-membered rings consisting of hydrocarbon groups, which rings contain one or more heteroatoms selected from the group comprising nitrogen, oxygen and sulfur, preferably nitrogen and/or oxygen, and which can be saturated or unsaturated. Examples of saturated heterocycles are 1,4-dioxane, tetrahydrofuran and 1,4-oxathiane. Examples of unsaturated heterocycles are furan, thiophene, pyridine, pyrimidine, thiazole, oxazole, isoxazole, pyridazine, pyrazine, indole, indazole, quinoline, isoquinoline, phthalazine and quinazoline. Unsaturated aromatic heterocycles are also called heteroaromatics.

Owing to their excellent pharmacological activity, the compounds according to the invention of the general structure of formula (I) and of the substructures of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) are suitable for the treatment of various diseases or conditions in which inhibition of the PDE4 enzyme is advantageous.

Such conditions and diseases are inter alia
- inflammatory diseases of the joints, in particular rheumatoid arthritis, psoriatic arthritis, ankylosing spondylitis (Bechterew's disease), gout, osteoarthritis;
- inflammatory diseases of the skin, in particular psoriasis, atopic dermatitis, lichen planus;
- inflammatory diseases of the eyes, in particular uveitis;
- gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps;
- inflammatory diseases of the internal organs, in particular SLE (systemic lupus erythematosus) including lupus nephritis, chronic prostatitis, interstitial cystitis;
- hyperplastic diseases, in particular benign prostatic hyperplasia;
- respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia;
- diseases of the fibrotic spectrum, in particular hepatic fibrosis, systemic sclerosis, scleroderma;
- cancers, in particular haematopoietic cancers, inter alia B-cell lymphoma, T-cell lymphoma, in particular CLL and CML (chronic lymphatic and chronic myeloid leukaemia), ALL and AML (acute lymphatic and acute myeloid leukaemia), and gliomas;
- metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension);
- psychological disorders, in particular schizophrenia, depression, in particular bipolar or manic depression, dementia, memory loss, generalised anxiety disorder (GAD); and
- diseases of the peripheral or central nervous system, in particular Parkinson's disease, multiple sclerosis, Alzheimer's disease, stroke, ALS (amyotrophic lateral sclerosis).

One of the advantages of the compounds according to the invention of the general structure of formula (I) and of a substructures of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) is that they are selective PDE4B inhibitors. The advantage of this selectivity lies in the fact that the PDE4D enzyme for example is not inhibited or is only partly inhibited, and hence the use of such selective PDE4B inhibitors gives rise to no side-effects or to markedly reduced side-effects. Undesired side-effects are for example emesis and nausea, in particular indisposition, vomiting and sickness. The therapeutic range of the compounds according to the invention is therefore advantageous.

The invention therefore also provides a pharmaceutical composition (medicament) containing at least one compound according to the invention of the general structure of formula (I) or of a substructures of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio.

The invention therefore also provides a compound according to the invention of the general structure of formula (I) or of a substructures of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio for use as a medicament, in particular for the treatment of conditions or diseases that can be treated by inhibition of the PDE4 enzyme, in particular the PDE4B enzyme.

The invention also provides a compound according to the invention of the general structure of formula (I) or of a substructures of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio for use as a medicament for the treatment of inflammatory diseases of the joints, in particular rheumatoid arthritis, psoriatic arthritis, ankylosing spondylitis (Bechterew's disease), gout, osteoarthritis; and/or inflammatory diseases of the skin, in particular psoriasis, atopic dermatitis, lichen planus; and/or inflammatory diseases of the eyes, in particular uveitis; gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps; inflammatory diseases of the internal organs, in particular SLE (systemic lupus erythematosus) including lupus nephritis, chronic prostatitis, interstitial cystitis; and/or hyperplastic diseases, in particular benign prostatic hyperplasia; respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia; diseases of the fibrotic spectrum, in particular hepatic fibrosis, systemic sclerosis, scleroderma; cancers, in particular haematopoietic cancers, inter alia B-cell lymphomas, T-cell lymphomas, in particular CLL and CML (chronic lymphatic and chronic myeloid leukaemia), ALL and AML (acute lymphatic and acute myeloid leukaemia), and gliomas; metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension); psychological disorders, in particular schizophrenia, depression, in particular bipolar or manic depression, dementia, memory loss, generalised anxiety disorder (GAD); and/or diseases of the peripheral or central nervous system, in particular Parkinson's disease, multiple sclerosis, Alzheimer's disease, stroke, ALS (amyotrophic lateral sclerosis).

The invention also provides a compound according to the invention of the general structure of formula (I) or of a substructures of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio for use as a medicament for the treatment of inflammatory diseases of the joints (in particular rheumatoid arthritis, psoriatic arthritis, ankylosing spondylitis (Bechterew's disease), gout, osteoarthritis), the skin (in particular psoriasis, atopic dermatitis, lichen planus) or the eyes (in particular uveitis), of respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia; of metabolic diseases, in particular type 2 diabetes, metabolic syndrome, obesity/adiposity, fatty liver disease (not alcohol-induced), and/or cardiovascular diseases, in particular arteriosclerosis, PAH (pulmonary arterial hypertension).

The invention also provides a compound according to the invention of the general structure of formula (I) or of a substructure of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio for use as a medicament for the treatment of rheumatoid arthritis, psoriatic arthritis, ankylosing spondylitis (Bechterew's disease), psoriasis, COPD (chronic obstructive pulmonary disease), asthma, type 2 diabetes and/or metabolic syndrome.

The invention also provides the use of a compound according to the invention of the general structure of formula (I) (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of inflammatory diseases of the joints, in particular rheumatoid arthritis, psoriatic arthritis, ankylosing spondylitis (Bechterew's disease), gout, osteoarthritis; inflammatory diseases of the skin, in particular psoriasis, atopic dermatitis, lichen planus; inflammatory diseases of the eyes, in particular uveitis; gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps; inflammatory diseases of the internal organs, in particular SLE (systemic lupus erythematosus) including lupus nephritis, chronic prostatitis, interstitial cystitis; hyperplastic diseases, in particular benign prostatic hyperplasia; respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia; diseases of the fibrotic spectrum, in particular hepatic fibrosis, systemic sclerosis, scleroderma; cancers, in particular haematopoietic cancers, inter alia B-cell lymphomas, T-cell lymphomas, in particular CLL and CML (chronic lymphatic and chronic myeloid leukaemia), ALL and AML (acute lymphatic and acute myeloid leukaemia), and gliomas; metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension); psychological disorders, in particular schizophrenia, depression, in particular bipolar or manic depression, dementia, memory loss, generalised anxiety disorder (GAD); and/or diseases of the peripheral or central nervous system, in particular Parkinson's disease, multiple sclerosis, Alzheimer's disease, stroke, ALS (amyotrophic lateral sclerosis).

Preferred according to the invention is the use of a compound according to the invention of the general structure of formula (I) or of a compound of the general structure of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of inflammatory diseases of the joints (in particular rheumatoid arthritis, psoriatic arthritis, ankylosing spondylitis (Bechterew's disease), gout, osteoarthritis), skin (in particular psoriasis, atopic dermatitis, lichen planus) or eyes (in particular uveitis).

Preferred according to the invention is the use of a compound according to the invention of the general structure of formula (I) or of a compound of the general structure of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps.

Preferred according to the invention is the use of a compound according to the invention of the general structure of formula (I) or of a compound of the general structure of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of inflammatory diseases of the internal organs, in particular SLE (systemic lupus erythematosus) including lupus nephritis, chronic prostatitis, interstitial cystitis.

Preferred according to the invention is the use of a compound according to the invention of the general structure of formula (I) or of a compound of the general structure of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of hyperplastic diseases, in particular benign prostatic hyperplasia.

Preferred according to the invention is the use of a compound according to the invention of the general structure of formula (I) or of a compound of the general structure of formula substructures of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia.

Preferred according to the invention is the use of a compound according to the invention of the general structure of formula (I) or of a compound of the general structure of formula substructures of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of diseases of the fibrotic spectrum, in particular hepatic fibrosis, systemic sclerosis, scleroderma.

Preferred according to the invention is the use of a compound according to the invention of the general structure of formula (I) or of a compound of the general structure of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of cancers, in particular haematopoietic cancers, inter alia B-cell lymphomas, T-cell lymphomas, in particular CLL and CML (chronic lymphatic and chronic myeloid leukaemia), ALL and AML (acute lymphatic and acute myeloid leukaemia), and gliomas.

Preferred according to the invention is the use of a compound according to the invention of the general structure of formula (I) or of a compound of the general structure of formula substructures of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension).

Preferred according to the invention is the use of a compound according to the invention of the general structure of formula (I) or of a compound of the general structure of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of psychological disorders, in particular schizophrenia, depression, in particular bipolar or manic depression, dementia, memory loss, generalised anxiety disorder (GAD).

Preferred according to the invention is the use of a compound according to the invention of the general structure of formula (I) or of a compound of the general structure of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of diseases of the peripheral or central nervous system, in particular Parkinson's disease, multiple sclerosis, Alzheimer's disease, stroke, ALS (amyotrophic lateral sclerosis).

Particularly preferred is the use of a compound according to the invention of the general structure of formula (I) or of a compound of the general structure of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of one or more of the following diseases or conditions: rheumatoid arthritis, psoriatic arthritis, ankylosing spondylitis (Bechterew's disease), psoriasis, COPD (chronic obstructive pulmonary disease) and asthma.

The invention also provides a method for the treatment of inflammatory diseases of the joints, in particular rheumatoid arthritis, psoriatic arthritis, ankylosing spondylitis (Bechterew's disease), gout, osteoarthritis; inflammatory diseases of the skin, in particular psoriasis, atopic dermatitis, lichen planus; inflammatory diseases of the eyes, in particular uveitis; gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps; inflammatory diseases of the internal organs, in particular SLE (systemic lupus erythematosus) including lupus nephritis, chronic prostatitis, interstitial cystitis; hyperplastic diseases, in particular benign prostatic hyperplasia; respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia; diseases of the fibrotic spectrum, in particular hepatic fibrosis, systemic sclerosis, scleroderma; cancers, in particular haematopoietic cancers, inter alia B-cell lymphomas, T-cell lymphomas, in particular CLL and CML (chronic lymphatic and chronic myeloid leukaemia), ALL and AML (acute lymphatic and acute myeloid leukaemia), and gliomas; metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension); psychological disorders, in particular schizophrenia, depression, in particular bipolar or manic depression, dementia, memory loss, generalised anxiety disorder (GAD); and/or diseases of the peripheral or central nervous system, in particular Parkinson's disease, multiple sclerosis, Alzheimer's disease, stroke, ALS (amyotrophic lateral sclerosis) in a human, which is characterised in that a therapeutically effective amount of at least one compound according to the invention of the general structure of formula (I) or of a substructures of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of inflammatory diseases of the joints (in particular rheumatoid arthritis, psoriatic arthritis, ankylosing spondylitis (Bechterew's disease), gout, osteoarthritis), skin (in particular psoriasis, atopic dermatitis, lichen planus) or eyes (in particular uveitis) in a human is preferred which is characterised in that a therapeutically effective amount of at least one compound according to the invention of the general structure of formula (I) or of a substructure of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps, in a human is preferred which is characterised in that a therapeutically effective amount of at least one compound according to the invention of the general structure of formula (I) or of a substructure of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of inflammatory diseases of the internal organs, in particular SLE (systemic lupus erythematosus) including lupus nephritis, chronic prostatitis and/or interstitial cystitis, in a human is preferred which is characterised in that a therapeutically effective amount of at least one compound according to the invention of the general structure of formula (I) or of a substructure of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of hyperplastic diseases, in particular benign prostatic hyperplasia, in a human is preferred which is characterised in that a therapeutically effective amount of at least one compound according to the invention of the general structure of formula (I) or of a substructure of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis and/or pneumonia in a human is preferred which is characterised in that a therapeutically effective amount of at least one compound according to the invention of the general structure of formula (I) or of a substructure of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of diseases of the fibrotic spectrum, in particular hepatic fibrosis, systemic sclerosis and/or scleroderma, in a human is preferred which is characterised in that a therapeutically effective amount of at least one compound according to the invention of the general structure of formula (I) or of a substructures of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of cancers, in particular haematopoietic cancers, inter alia B-cell lymphomas, T-cell lymphomas, in particular CLL and CML (chronic lymphatic and chronic myeloid leukaemia), ALL and AML (acute lymphatic and acute myeloid leukaemia), and gliomas in a human is preferred which is characterised in that a therapeutically effective amount of at least one compound according to the invention of the general structure of formula (I) or of a substructures of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension), in a human is preferred which is characterised in that a therapeutically effective amount of at least one compound according to the invention of the general structure of formula (I) or of a substructures of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of psychological disorders, in particular schizophrenia, depression, in particular bipolar or manic depression, dementia, memory loss and/or generalised anxiety disorder (GAD), in a human is preferred which is characterised in that a therapeutically effective amount of at least one compound according to the invention of the general structure of formula (I) or of a substructures of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of diseases of the peripheral or central nervous system, in particular Parkinson's disease, multiple sclerosis, Alzheimer's disease, stroke and/or ALS (amyotrophic lateral sclerosis), in a human is preferred which is characterised in that a therapeutically effective amount of at least one compound according to the invention of the general structure of formula (I) or of a substructures of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of one or more of the following diseases or conditions: rheumatoid arthritis, psoriatic arthritis, ankylosing spondylitis (Bechterew's disease), psoriasis, COPD (chronic obstructive pulmonary disease), asthma and also type 2 diabetes and metabolic syndrome in a human is preferred which is characterised in that a therapeutically effective amount of at least one compound according to the invention of the general structure of formula (I) or of a substructures of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

The amount of active ingredient to be administered to the person or patient varies and is dependent on the patient's weight, age and medical history and on the type of administration, the indication and the severity of the illness. Conventionally 0.1 to 5000 mg/kg, in particular 1 to 500 mg/kg, preferably 2 to 250 mg/kg of body weight of at least one compound according to the invention of the general structure of formula (I) or of a substructure of formula substructures of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) are administered.

The invention relates furthermore to a method (01) for producing a compound according to the invention of general formula (XX) and (XXI), respectively in which Q is Q1 and T is oxygen (if n=1 then the target compound corresponds to a compound of formula (XX-G) and (XXI-G), respectively and if n=2 then the target compound corresponds to a compound of formula (XX-H) and (XXI-H), respectively, encompassing the following steps:

Step (i): Reaction of an amidine compound of general formula (II) with a β-keto ester of general formula (III) or (III-a) to form a 4-hydroxypyrimidine compound of formula (IV) or (VI-a)

in a solvent such as for example ethanol, n-propanol, isopropanol or dimethylformamide and in the presence of a base (e.g. sodium ethanolate, caesium carbonate or N,N-diisopropylethylamine (so-called Hünig base) at a temperature in the range from approximately 0° C. to approximately 130° C.;

Step (ii): Chlorination of the 4-hydroxypyrimidine compound of formula (IV) or (IV-a) with a chlorinating agent to form a compound (V) or (V-a)

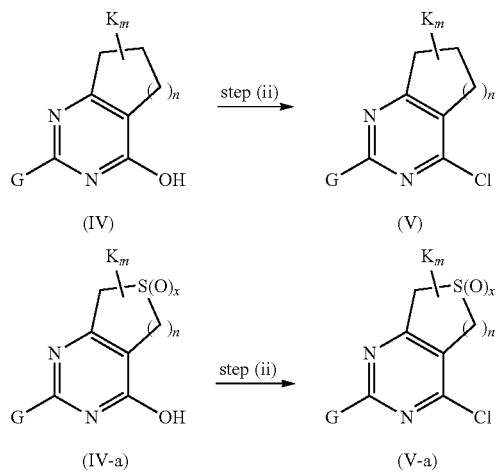

in a solvent, wherein the chlorinating agent can be phosphorus oxychloride;

Step (iii): Reaction of the 4-chloropyrimidine compound of formula (V) or (V-a) with a phenol of formula (VI) to form a compound of formula (VII) or (VII-a)

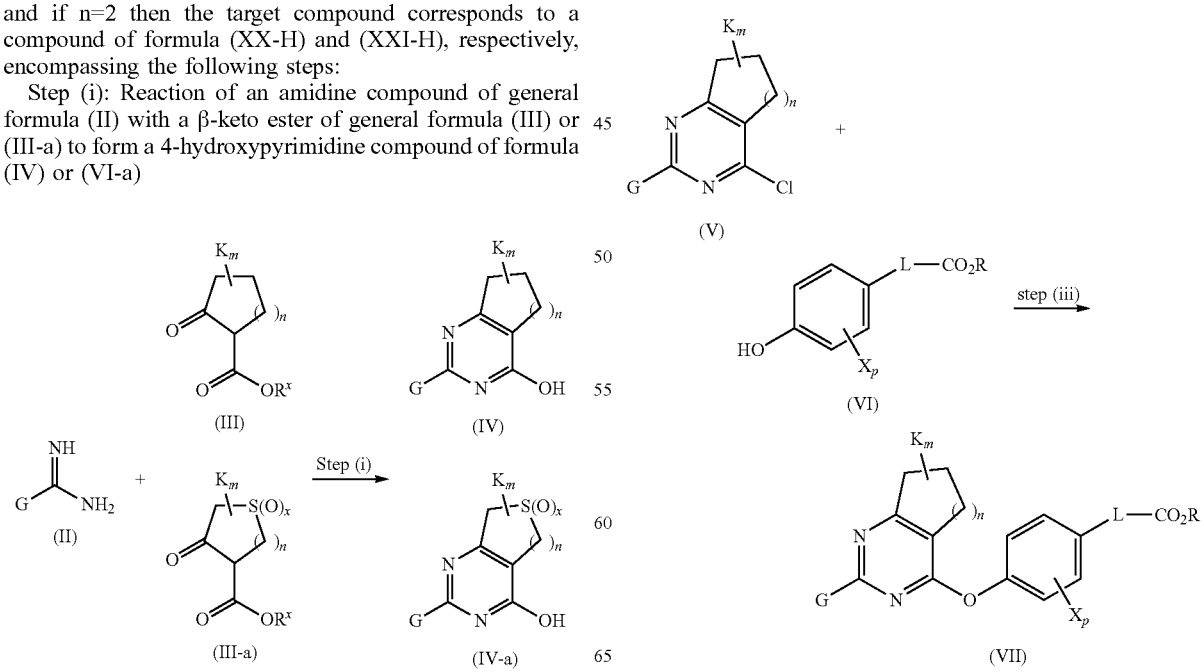

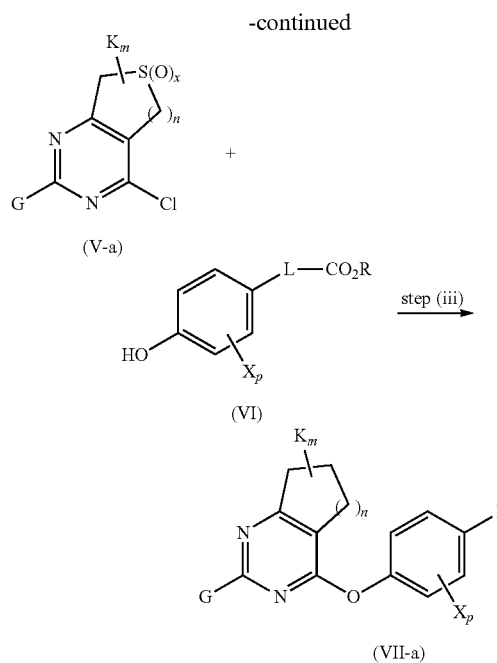

in a solvent and optionally in the presence of a base;

Step (iv): Acid or basic ester cleavage of the compound of formula (VII) or (VII-a) to form the target compound of formula (XX) or (XXI) in an organic solvent, which can contain water.

Step (i) of method (01), namely the reaction of an amidine compound of general formula (II) with a β-keto ester of general formula (III) or (III-a) to form a 4-hydroxypyrimidine compound of formula (IV) or (IV-a), is a condensation reaction. The β-keto ester of general formula (III) or (III-a) can also be present in the tautomeric enol form. Condensation reactions are generally known (see for example Chemistry—A European Journal 2008, 14, 6836-6844).

Step (ii) of method (01) is a generally known method by which the hydroxyl group of the 4-hydroxypyrimidine of general formula (IV) or (IV-a) can be chlorinated by standard methods (see for example Journal of the Chemical Society 1951, 1218-1221; Bioorganic & Medicinal Chemistry 2010, 18, 2704-2712). For example, compounds of general formula (V) and (V-a), respectively can be produced by reacting a 4-hydroxypyrimidine of general formula (IV) and (IV-a), respectively with phosphorus oxychloride at a temperature in the range from approximately 20° C. to approximately 100° C., preferably at a temperature in the range from approximately 50° C. to approximately 100° C.

Step (iii) of method (01), namely the reaction of the 4-chloropyrimidine compounds of general formula (V) and (V-a), respectively with the corresponding phenols of general formula (VI) to form the compounds of general formula (VII) and (VII-a), respectively takes place by standard methods in a solvent and optionally in the presence of a base. Suitable solvents are known to the person skilled in the art. Examples of such solvents are dioxane, tetrahydrofuran, dimethylformamide or dimethylsulfoxide. Examples of suitable bases are 1,8-diazabicyclo[5.4.0]undec-7-ene (DBU), triethylamine, sodium hydroxide solution and caesium or potassium carbonate. The reaction can take place at a temperature in the range from approximately 20° C. to approximately 200° C. The reaction preferably takes place at a temperature in the range from 50° C. to 130° C.

The ester cleavage (ester hydrolysis) in step (iv) of method (01) takes place by known methods. Ester cleavages are described for example by P. G. M. Wuts, T. W. Greene in Greene's Protective Groups in Organic Synthesis, 4th Edition, 2007, pages 538-616, Wiley-Interscience. They can be performed hydrolytically, for example, in the presence of acids or bases (e.g. alkali hydroxides such as for example lithium or sodium hydroxide) in an organic solvent to which varying proportions of water can be added. Other frequently used methods of ester cleavage involve the acid-catalysed cleavage of a tert-butyl ester (R=tert-butyl) by generally known methods, for example using trifluoroacetic acid in dichloromethane, or the hydrogenolysis of benzyl esters.

For the preparation of compounds of formula (XXI), it is favorable to use in step (i) starting materials of formula (III-a) wherein x is 0 and to convert the resulting compounds by an oxidation reaction to the corresponding compounds wherein x is 1 or 2. Accordingly, method 01 then additionally comprise an oxidation step (step (ox)) between step (iii) and (iv) which comprises reacting a compound of (VII-a) wherein x is 0 with an oxidizing agent (e.g. m-chloroperoxybenzoic acid) under appropriate reaction conditions (such as e.g. under cooling or at room temperature and in a solvent (e.g. $CH_2Cl_2$) for a certain time period). By choosing the appropriate amount or equivalents of the oxidizing agent based on the amount of used starting material of formula (III-a), the oxidation reaction can be controlled so that a compound of formula (VII-a) with x being 1 or, alternatively, with x being 2 can be synthesized.

The invention likewise relates to a method (02) for producing a compound according to the invention of general formula (XX) in which Q is Q1 and T is oxygen (if n=1 then the target compound corresponds to a compound of formula (XX-G) and if n=2 then the target compound corresponds to a compound of formula (XX-H)), encompassing the following steps:

Step (i'): Reacting a compound of formula (VIII) with a compound of formula (VI) to form a compound of formula (IX)

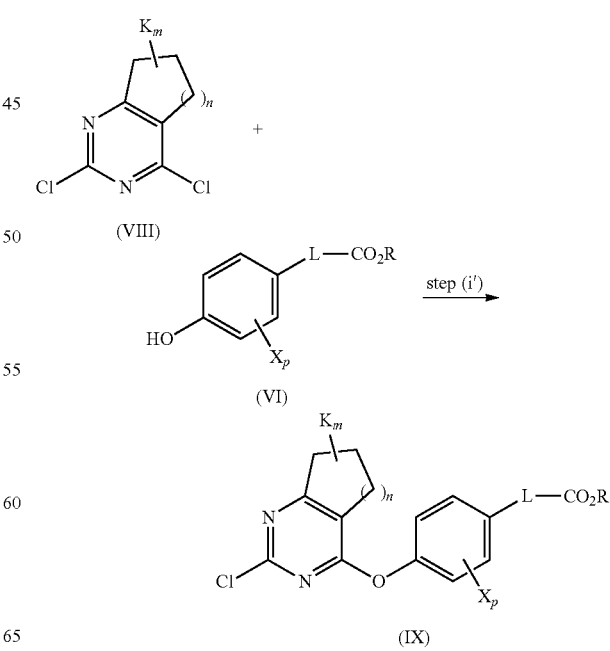

in a solvent (e.g. dioxane, tetrahydrofuran, dimethylformamide or dimethylsulfoxide) and optionally in the presence of a base (e.g. 1,8-diazabicyclo[5.4.0]undec-7-ene (DBU), triethylamine, sodium hydroxide solution, caesium or potassium carbonate) at a temperature in the range from approximately 20° C. to approximately 200° C., preferably from approximately 50° C. to approximately 130° C.;

Step (ii'): Reacting the compound of formula (IX) with a compound G-M to form a compound of formula (VII) under the conditions of a Suzuki coupling or a Stille coupling

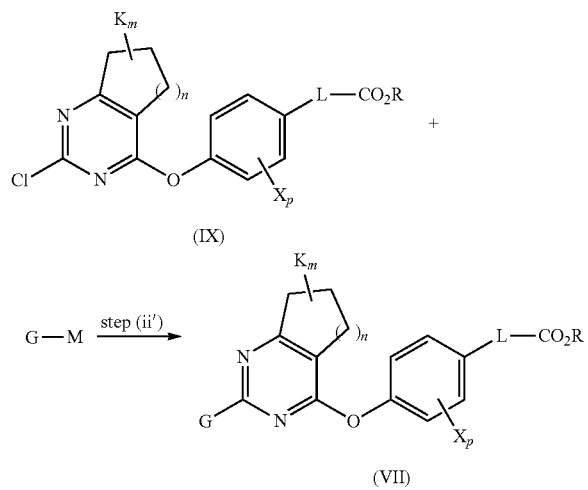

wherein G in the compound G-M has the meaning described in connection with the compounds according to the invention and M has the following meaning:

In the case of a Suzuki coupling M is $B(OH)_2$ (boronic acid), $B(OR^x)_2$ (boronic acid ester) or an optionally ($C_1$-$C_6$) alkyl-substituted 1,3,2-dioxaborolane (e.g. 4,4,5,5-tetramethyl-1,3,2-dioxaborolane) and in the case of a Stille coupling M is $SnR^x_3$ (e.g. trimethylstannyl or tributylstannyl compounds (M=$Sn(CH_3)_3$, $SnBn_3$));

Step (iii'): Obtaining of the target compound of formula (XX) by acid or basic ester cleavage of the compound of formula (VII) by the method described in method (01) for step (iv).

Step (i') of method (02), namely the reaction of a 2,4-dichloropyrimidine compound of general formula (VIII) with suitable phenols (VI) to produce compounds of formula (IX), takes place by known methods of nucleophilic aromatic substitution. The reaction can be performed for example in a solvent such as dioxane, tetrahydrofuran, dimethylformamide or dimethylsulfoxide in the presence of a base such as 1,8-diazabicyclo[5.4.0]undec-7-ene (DBU), triethylamine, sodium hydroxide solution, caesium or potassium carbonate at a temperature in the range from approximately 20° C. to approximately 200° C., preferably from approximately 50° C. to approximately 130° C.

Step (ii') of method (02), namely the reaction under Stille or Suzuki coupling reaction conditions takes place by known methods (cf. Tetrahedron 2005, 61, 2245-67). The Suzuki coupling can be performed for example in the presence of a catalyst such as tetrakis(triphenylphosphine)palladium(0) complex or [1,1'-bis(diphenylphosphino)ferrocene]dichloropalladium(II) complex and a base (e.g. caesium carbonate) in a solvent or solvent blend (e.g. dioxane or acetonitrile/water blend). Step (ii') of method (02) can also be performed in the production of a compound of formula (XI) starting from a compound of formula (X).

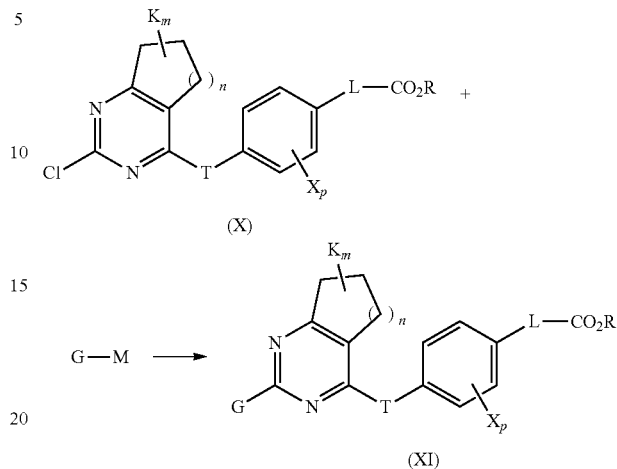

The invention likewise relates to a method (03) for preparing a compound according to the invention of general formula (XX) in which Q is Q1 and T is oxygen (if n=1 then the target compound corresponds to a compound of formula (XX-G) and if n=2 then the target compound corresponds to a compound of formula (XX-H), encompassing the following steps:

Step (i"): Reacting the compound of formula (IV) with a compound of formula (VI) to form a compound of formula (VII)

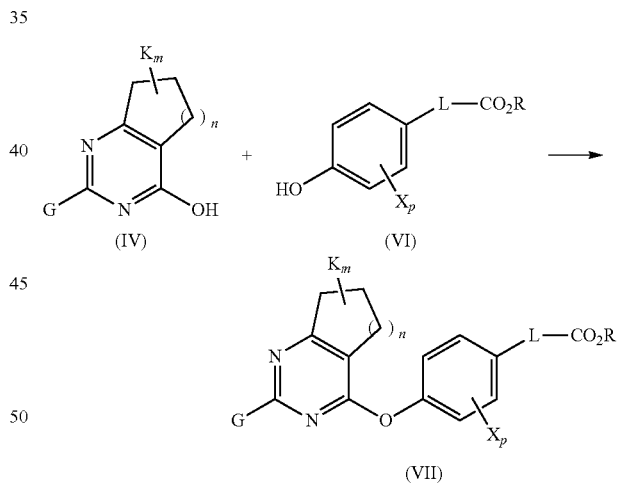

in the presence of a coupling reagent (e.g. 1H-benzotriazol-1-yloxy-tris(dimethylamino)-phosphoniumhexafluorophosphate (BOP)) and a base (e.g. caesium carbonate) in a solvent (e.g. tetrahydrofuran); and Step (ii'): Obtaining the target compound of formula (XX) by acid or basic ester cleavage of the compound of formula (VII) by the method described in method (01) for step (iv).

Step (i') of method (03), namely the reaction of a 4-hydroxypyrimidine compound of general formula (IV) with the corresponding phenol of general formula (VI) to form a compound of formula (VII) takes place by known methods from peptide chemistry (e.g. Tetrahedron 2004, 60, 2447-2467). In these methods carbodiimides or other coupling reagents (e.g. 1H-benzotriazol-1-yloxy-tris(dimethylamino) phosphoniumhexafluorophosphate (BOP)) are used in a solvent (e.g. tetrahydrofuran) and in the presence of a base (e.g. caesium carbonate).

The invention relates furthermore to a method (04) for preparing a compound according to the invention of general formula (XX) and (XXI), respectively in which Q is Q1 and T is $CH_2$, $CHR^1$ or $CR^1R^2$ (if n=1 then the target compound corresponds to a compound of formula (XX-J) and (XXI-J), respectively, or (XX-L) or (XX-N) and if n=2 then the target compound corresponds to a compound of formula (XX-K), and (XXI-K), respectively, or (XX-M), (XX-O)), encompassing the following steps:

Step (a): Synthesising a 4-chloropyrimidine compound of formula (V) and (V-a), respectively as described in method (01);

Step (b): Reacting the 4-chloropyrimidine compound of formula (V) and (V-a), respectively with suitable zinc halides of formula (X), in which X is chlorine, bromine and iodine, preferably bromine and iodine, by means of a palladium-catalysed cross-coupling reaction, to produce compounds of formula (XI) and (XI-a), respectively in which T has the aforementioned meaning; and

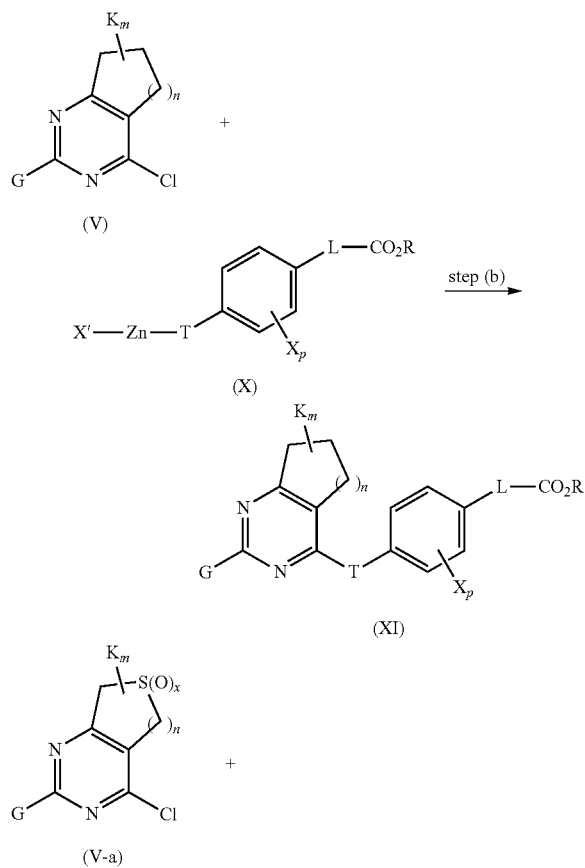

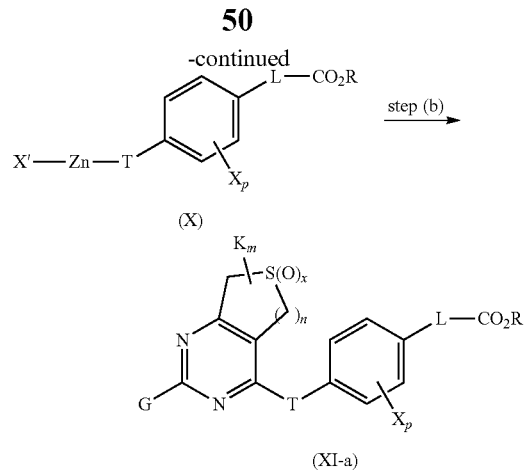

Step (c): Obtaining the target compound of formula (XX) and (XXI), respectively by acid or basic ester cleavage of the compound of formula (XI) and (XI-a), respectively by the method described in method (01) for step (iv).

Step (b) of method (04), namely the palladium-catalysed cross-coupling reaction of suitable zinc halides of formula (X) with a 4-chloropyrimidine compound of formula (V), takes place by known methods (see for example Synlett 2009, 14, 2257-2260).

For the preparation of compounds of formula (XXI), it is favorable to use in step (a) starting materials of formula (V-a) wherein x is 0 and to convert the resulting compounds by an oxidation reaction to the corresponding compounds wherein x is 1 or 2. Accordingly, method 04 then additionally comprise an oxidation step (step (ox)) between step (b) and (c) which comprises reacting a compound of (XI-a) wherein x is 0 with an oxidizing agent (e.g. m-chloroperoxybenzoic acid) under appropriate reaction conditions (such as e.g. under cooling or at room temperature and in a solvent (e.g. $CH_2Cl_2$) for a certain time period). By choosing the appropriate amount or equivalents of the oxidizing agent based on the amount of used starting material of formula (XI-a), the oxidation reaction can be controlled so that a compound of formula (XI-a) with x being 1 or, alternatively, with x being 2 can be synthesized.

Unless otherwise specified, the radicals R and $R^x$ in the general formulae of the compounds that are used or reacted in the aforementioned methods (01), (02), (03) and (04) are defined as follows:

R is a leaving group (e.g. methyl, ethyl, tert-butyl or benzyl) and $R^x$ is ($C_1$-$C_6$) alkyl, preferably methyl.

All other chemical groupings, substituents and indices have the meanings given in relation to the compound of formula (I).

The compounds according to the invention can be produced in the manner described here or in an analogous manner.

The compounds according to the invention are specified in the table below, without limiting the invention thereto.

TABLE 1

| No. | General formula | G | Z | k | T | Q | K | m | p | x |
|---|---|---|---|---|---|---|---|---|---|---|
| 1 | (XX-A) | G34 | 4-OMe, 3-F | 2 | O | Q3 | — | 0 | 0 | — |
| 2 | (XX-A) | G34 | 4-OMe, 3-Cl | 2 | O | Q3 | — | 0 | 0 | — |
| 3 | (XX-A) | G34 | 4-F, 3-F | 2 | O | Q3 | — | 0 | 0 | — |

TABLE 1-continued

| No. | General formula | G | Z | k | T | Q | K | m | p | x |
|---|---|---|---|---|---|---|---|---|---|---|
| 4 | (XX-A) | G34 | 4-OMe, 3-F | 2 | O | Q2 | — | 0 | 0 | — |
| 5 | (XX-A) | G34 | 4-OMe, 3-Cl | 2 | O | Q2 | — | 0 | 0 | — |
| 6 | (XX-A) | G34 | 4-F, 3-F | 2 | O | Q2 | — | 0 | 0 | — |
| 7 | (XX-A) | G5 | Cl | 1 | O | Q3 | — | 0 | 0 | — |
| 8 | (XX-A) | G5 | Cl | 1 | O | Q2 | — | 0 | 0 | — |
| 9 | (XX-A) | G5 | Cl | 1 | CH2 | Q3 | — | 0 | 0 | — |
| 10 | (XX-B) | G5 | Cl | 1 | O | Q3 | — | 0 | 0 | — |
| 11 | (XX-B) | G5 | Cl | 1 | O | Q2 | — | 0 | 0 | — |
| 12 | (XX-B) | G5 | Cl | 1 | O | Q3 | γ-F, γ-F | 2 | 0 | — |
| 13 | (XX-A) | G34 | 4-OH, 3-Cl | 2 | O | Q3 | — | 0 | 0 | — |
| 14 | (XX-A) | G34 | 4-OMe, 3-Br | 2 | O | Q3 | — | 0 | 0 | — |
| 15 | (XXI-A) | G5 | F | 1 | O | Q3 | — | 0 | 0 | 2 |
| 16 | (XXI-A) | G34 | 4-OMe, 3-F | 2 | O | Q3 | — | 0 | 0 | 2 |
| 17 | (XXI-A) | G34 | 4-OMe, 3-Cl | 2 | O | Q3 | — | 0 | 0 | 2 |
| 18 | (XXI-A) | G34 | 4-OMe | 1 | O | Q3 | — | 0 | 0 | 2 |
| 19 | (XXI-A) | G5 | Cl | 1 | O | Q3 | — | 0 | 0 | 0 |
| 20 | (XXI-A) | G5 | Cl | 1 | O | Q3 | — | 0 | 0 | 1 |
| 21 | (XXI-A) | G5 | Cl | 1 | O | Q3 | — | 0 | 0 | 2 |
| 22 | (XXI-B) | G5 | Cl | 1 | O | Q3 | — | 0 | 0 | 0 |
| 23 | (XXI-B) | G5 | Cl | 1 | O | Q3 | — | 0 | 0 | 1 |
| 24 | (XXI-B) | G5 | Cl | 1 | O | Q3 | — | 0 | 0 | 2 |
| 25 | (XXI-A) | G34 | 4-OMe, 3-F | 2 | O | Q3 | — | 0 | 0 | 1 |
| 26 | (XXI-A) | G34 | 4-OMe, 3-F | 2 | O | Q3 | — | 0 | 0 | 0 |
| 27 | (XXI-A) | G34 | 4-OMe, 3-Cl | 2 | O | Q3 | — | 0 | 0 | 1 |
| 28 | (XXI-A) | G34 | 4-OMe, 3-Cl | 2 | O | Q3 | — | 0 | 0 | 0 |
| 29 | (XXI-A) | G34 | 4-F, 3-F | 2 | O | Q3 | — | 0 | 0 | 2 |
| 30 | (XXI-A) | G34 | 4-F, 3-F | 2 | O | Q3 | — | 0 | 0 | 1 |
| 31 | (XXI-A) | G34 | 4-F, 3-F | 2 | O | Q3 | — | 0 | 0 | 0 |
| 32 | (XXI-A) | G5 | Cl | 1 | CH2 | Q3 | — | 0 | 0 | 2 |
| 33 | (XXI-A) | G5 | Cl | 1 | CH2 | Q3 | — | 0 | 0 | 1 |
| 34 | (XXI-A) | G5 | Cl | 1 | CH2 | Q3 | — | 0 | 0 | 0 |
| 35 | (XXI-A) | G34 | 4-OH, 3-Cl | 2 | O | Q3 | — | 0 | 0 | 2 |
| 36 | (XXI-A) | G34 | 4-OMe, 3-Br | 2 | O | Q3 | — | 0 | 0 | 2 |
| 37 | (XXI-A) | G34 | 4-OMe, 3-Br | 2 | O | Q3 | — | 0 | 0 | 1 |
| 38 | (XXI-A) | G34 | 4-OMe, 3-Br | 2 | O | Q3 | — | 0 | 0 | 0 |
| 39 | (XX-A) | G5 | F | 1 | O | Q3 | — | 0 | 0 | — |
| 40 | (XXI-A) | G5 | F | 1 | O | Q3 | — | 0 | 0 | 1 |
| 41 | (XXI-A) | G5 | F | 1 | O | Q3 | — | 0 | 0 | 0 |
| 42 | (XX-A) | G34 | 4-OMe | 1 | O | Q3 | — | 0 | 0 | — |
| 43 | (XXI-A) | G34 | 4-OMe | 1 | O | Q3 | — | 0 | 0 | 1 |
| 44 | (XXI-A) | G34 | 4-OMe | 1 | O | Q3 | — | 0 | 0 | 0 |
| 45 | (XX-A) | G6 | — | 0 | O | Q3 | — | 0 | 0 | 0 |
| 46 | (XX-A) | G6 | 2-Cl | 1 | O | Q3 | — | 0 | 0 | 0 |
| 47 | (XX-A) | G1 | 5-CONH2 | 1 | O | Q3 | — | 0 | 0 | 0 |
| 48 | (XX-A) | G1 | 5-CN | 1 | O | Q3 | — | 0 | 0 | 0 |
| 49 | (XX-A) | G1 | 5-Br | 1 | O | Q3 | — | 0 | 0 | 0 |
| 50 | (XX-A) | G1 | 5-CH3, 4-Br | 2 | O | Q3 | — | 0 | 0 | 0 |
| 51 | (XX-A) | G1 | 5-SCH3 | 1 | O | Q3 | — | 0 | 0 | 0 |
| 52 | (XX-A) | G1 | 5-SO2CH3 | 1 | O | Q3 | — | 0 | 0 | 0 |
| 53 | (XX-A) | G34 | 4-Br | 1 | O | Q3 | — | 0 | 0 | 0 |
| 54 | (XX-A) | G34 | 2-Br | 1 | O | Q3 | — | 0 | 0 | 0 |
| 55 | (XX-A) | G7 | — | 0 | O | Q3 | — | 0 | 0 | 0 |
| 56 | (XX-A) | G7 | 2-Cl | 1 | O | Q3 | — | 0 | 0 | 0 |
| 57 | (XX-A) | G34 | 3-F, 5-F, 4-OCH3 | 3 | O | Q3 | — | 0 | 0 | 0 |
| 58 | (XX-A) | G1 | 5-CH3 | 1 | O | Q3 | — | 0 | 0 | 0 |
| 59 | (XX-A) | G1 | 5-CH3 | 1 | O | Q3 | β-CH3 | 1 | 0 | 0 |

The medicaments, drugs and pharmaceutical compositions according to the invention can take the form of and be administered as liquid, semi-solid or solid dosage forms and as for example injection solutions, drops, juices, syrups, sprays, suspensions, granules, tablets, pellets, transdermal therapeutic systems, capsules, plasters, suppositories, ointments, creams, lotions, gels, emulsions or aerosols and contain, in addition to at least one compound according to the invention of the general structure of formula (I) or of a substructures of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) according to the pharmaceutical form and depending on the administration route, pharmaceutical auxiliary substances such as for example carrier materials, fillers, solvents, diluting agents, surface-active substances, dyes, preservatives, disintegrants, slip additives, lubricants, flavourings and/or binders. These auxiliary substances can be, for example: water, ethanol, 2-propanol, glycerol, ethylene glycol, propylene glycol, polyethylene glycol, polypropylene glycol, glucose, fructose, lactose, sucrose, dextrose, molasses, starch, modified starch, gelatine, sorbitol, inositol, mannitol, microcrystalline cellulose, methyl cellulose, carboxymethyl cellulose, cellulose acetate, shellac, cetyl alcohol, polyvinyl pyrrolidone, paraffins, waxes, natural and synthetic rubbers, acacia gum, alginates, dextran, saturated and unsaturated fatty acids, stearic acid, magnesium stearate, zinc stearate, glyceryl stearate, sodium lauryl sulfate, edible oils, sesame oil, coconut oil, groundnut oil, soya bean oil, lecithin, sodium lactate, polyoxyethylene and polyoxypropylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potash, calcium phosphate, dicalcium phosphate, potassium bromide, potassium iodide, talc, kaolin, pectin, crospovidone, agar and bentonite.

The choice of auxiliary substances and the amounts thereof to use depends on whether the medicament/drug is to be administered by oral, subcutaneous, parenteral, intravenous, vaginal, pulmonary, intraperitoneal, transdermal, intramuscular, nasal, buccal or rectal means or locally, for example for infections of the skin, mucous membranes and eyes. Preparations in the form of inter alia tablets, pastilles, capsules, granules, drops, juices and syrups are suitable for oral administration; solutions, suspensions, easily reconstitutable powders for inhalation and sprays are suitable for parenteral, topical and inhalative administration. Compounds according to the invention of the general structure (I) in a depot formulation, in dissolved form or in a plaster, optionally with addition of agents promoting skin penetration, are suitable preparations for percutaneous administration.

Preparation forms that are suitable for rectal, transmucosal, parenteral, oral or percutaneous administration can deliver the compounds according to the invention of the general structure (I) on a delayed release basis.

Preparation of the medicaments and pharmaceutical compositions according to the invention takes place using agents, equipment, methods and procedures that are well-known from the prior art of pharmaceutical formulation, such as are described for example in "Remington's Pharmaceutical Sciences", Ed. A. R. Gennaro, 17$^{th}$ edition, Mack Publishing Company, Easton Pa. (1985), in particular in part 8, chapters 76 to 93.

Thus, for example, for a solid formulation such as a tablet, the active ingredient of the medicament, i.e. a compound of the general structure of formula (I) or of a substructures of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) or of one of its pharmaceutically acceptable salts is granulated with a pharmaceutical carrier, e.g. conventional tablet ingredients such as corn starch, lactose, sucrose, sorbitol, talc, magnesium stearate, dicalcium phosphate or pharmaceutically acceptable rubbers, and pharmaceutical diluting agents such as water for example, to form a solid composition containing a compound according to the invention or a pharmaceutically acceptable salt thereof in a homogeneous distribution. A homogeneous distribution is understood here to mean that the active ingredient is evenly distributed throughout the entire composition so that the composition can be readily divided into identically effective single-unit dosage forms such as tablets, pills or capsules. The solid composition is then divided into single-unit dosage forms. The tablets or pills of the medicament according to the invention or of the compositions according to the invention can also be coated or compounded in another way so as to provide a delayed-release dosage form. Suitable coating agents are inter alia polymeric acids and mixtures of polymeric acids with materials such as for example shellac, cetyl alcohol and/or cellulose acetate.

The amount of active ingredient to be administered to the patient varies and is dependent on the patient's weight, age and medical history and on the type of administration, the indication and the severity of the illness. Conventionally 0.1 to 5000 mg/kg, in particular 1 to 500 mg/kg, preferably 2 to 250 mg/kg of body weight of at least one compound according to the invention of the general structure of formula (I) or of a substructures of formula (XX), (XX-A), (XX-B), (XX-C), (XX-D), (XX-E), (XX-F), (XX-G), (XX-H), (XX-J), (XX-K), (XX-L), (XX-M), (XX-N), (XX-O), (XXI), (XXI-A), (XXI-B), (XXI-C), (XXI-D), (XXI-E), (XXI-F), (XXI-G), (XXI-H), (XXI-J), (XXI-K) derived from formula (I) are administered.

The compounds according to the invention can be produced in the manner described below.

The following abbreviations are used hereafter: eq.=equivalent; calc.=calculated; f.=found; d=day; h=hour; min=minute; Rt=retention time; BINAP=2,2'-bis(diphenylphosphino)-1,1'-binaphthyl; BOP=(benzotriazol-1-yloxy)tris(dimethylamino)phosphonium hexafluorophosphate; CDI=carbonyldiimidazole; dba=dibenzylidene-acetone; DMAP=N,N-dimethylpyridin-4-amine; DMF=N,N-dimethylformamide; DMSO=dimethylsulfoxide; NMP=N-methyl-2-pyrrolidone; tBuXPhos=2-di-tert-butylphosphino-2,4,6-triisopropyl-1,1-biphenyl; tert=tertiary; THF=tetrahydrofuran; APCI=atmospheric pressure chemical ionization; ES-MS=electrospray mass spectrometry (ES-MS); PyBOP benzotriazole-1-yl-oxytripyrrolidinophosphonium hexafluorophosphate; TOFMS=time-of-flight mass spectrometer.

Synthesis Example 1: 2-(4-(2-(3-Fluoro-4-methoxyphenyl)-6,7-dihydro-5H-cyclopenta[d]pyrimidin-4-yloxy)phenyl)acetic acid (compound no. 1)

1a) 6,7-Dihydro-1H-cyclopenta[d]pyrimidine-2,4 (3H,5H)-dione

Trimethylsilyl chloride (4.18 g, 38.5 mmol) was added to a suspension of urea (3.78 g, 63 mmol) in DMF (3 ml). After cooling to 0° C., 2-oxo-cyclopentanecarboxylic acid methyl ester (5.0 g, 35 mmol) was added dropwise. The solution was heated to room temperature and stirred overnight, forming a colourless solid. 2N sodium hydroxide solution (50 ml) was added to the suspension and it was heated to 90° C. until the solid dissolved. Then it was cooled to room temperature and adjusted to pH 1 with concentrated hydrochloric acid. The resulting solid was filtered off, suspended in toluene and freed from solvent in a rotary evaporator. Drying with toluene was repeated a further two times. White solid. Yield: 4.9 g (92% of theory).

1H NMR (400 MHz, DMSO-d6, δ ppm): 1.90-1.98 (2H), 2.41-2.45 (2H), 2.60-2.64 (2H), 10.69 (s, 1H), 11.01 (s, 1H)

LC/MS (method 2): $R_t$=0.40 min, [M+H]$^+$ calc. for $C_7H_9N_2O_2$ 153.15. found 153.20.

1b) 2,4-Dichloro-6,7-dihydro-5H-cyclopenta[d]pyrimidine

A solution of 6,7-dihydro-1H-cyclopenta[d]pyrimidine-2,4(3H,5H)-dione (13.8 g, 90.7 mmol) and phosphorus oxychloride (45 ml) was heated to 100° C. for 8 h and then to 85° C. for 16 h. The reaction mixture was cooled and slowly poured onto ice-cold saturated sodium hydrogen carbonate solution.

Then extraction was performed with dichloromethane and the combined organic phases were dried with magnesium sulfate. The solvent was removed in a rotary evaporator and the residue was purified by column chromatography [cyclohexane/ethyl acetate 8:1]. Colourless solid. Yield: 12.1 g (70% of theory).

1H NMR (400 MHz, CDCl3, δ ppm): 2.14-2.25 (2H), 2.98 (t, J=7.5, 2H), 3.06 (t, J=7.9, 1H)

LC/MS (method 2): $R_t$=3.00 min, [M+H]$^+$ calc. for $C_7H_7Cl_2N_2$ 190.05. found 190.20.

1c) 2-(4-(2-Chloro-6,7-dihydro-5H-cyclopenta[d]pyrimidin-4-yloxy)phenyl)acetic acid methyl ester 1,8-Diazabicyclo[5.4.0]undec-7-ene (1.5 ml, 10 mmol) was added to 2,4-dichloro-6,7-dihydro-5H-cyclopenta[d]pyrimidine (1.89 g, 10 mmol) and 2-(4-hydroxyphenyl)acetic acid methyl ester (1.66 g, 10 mmol) in dioxane (40 ml) and the mixture was refluxed for 2 h while stirring. Water was added to the suspension and extraction was performed with dichloromethane. After drying the combined organic phases with magnesium sulfate, the solvent was removed and the residue was purified by column chromatography [cyclohexane/ethyl acetate 5:1]. White solid. Yield: 2.56 g (80% of theory).

1H NMR (400 MHz, CDCl3, δ ppm): 2.20 (2H), 2.93 (t, J=7.5, 2H), 3.00 (t, J=7.8, 2H), 3.64 (s, 2H), 3.71 (s, 3H), 7.12 (d, J=8.5, 2H), 7.32 (d, J=8.5, 2H)

LC/MS (method 2): $R_t$=3.67 min, [M+H]$^+$ calc. for $C_{16}H_{16}ClN_2O_3$ 319.76. found 319.20.

1d) 2-(4-(2-(3-Fluoro-4-methoxyphenyl)-6,7-dihydro-5H-cyclopenta[d]pyrimidin-4-yloxy)phenyl)acetic acid A solution of the product from reaction 1c) (319 mg, 1 mmol), 3-fluoro-4-methoxyphenyl boronic acid (204 mg, 1.2 mmol), potassium carbonate (207 mg, 1.5 mmol) and bis(triphenylphosphine)palladium(II) dichloride (5 mol %, 35 mg, 50 μmol) in dioxane/water (12 ml, 5:1) was refluxed for 1 h while stirring. Then 4N sodium hydroxide solution (0.5 ml) was added and the mixture was refluxed for 1 h while stirring. The solution was filtered and 2N hydrochloric acid (2 ml) and water (5 ml) were added to the filtrate. The solid that formed was separated off and purified by column chromatography [ethyl acetate]. White solid. Yield: 130 mg (33% of theory).

1H NMR (400 MHz, DMSO-d6, δ ppm): 2.14 (2H), 2.90 (t, J=7.5, 2H), 2.97 (t, J=7.8, 2H), 3.64 (s, 2H), 3.68 (s, 3H), 7.20 (d, J=12.0, 1H), 7.23 (d, J=8.5, 2H), 7.36 (d, J=8.5, 2H), 7.79 (dd, J=2.1, 12.9, 1H), 7.23 (ddd, J=1.1, 2.1, 8.7, 1H)

13C NMR (100 MHz, DMSO-d6, δ ppm): 21.5, 26.2, 33.7, 56.0, 66.3, 113.5 (d, 4JC,F=1.5), 114.4 (d, 2JC,F=19.6), 117.8, 121.2, 124.2 (d, 3JC,F=3.1), 129.9 (d, 3JC,F=6.5), 130.3, 131.9, 149.1 (d, 2JC,F=10.7), 150.9, 151.1 (d, 1JC,F=243), 160.9 (d, 4JC,F=2.9), 164.7, 172.6, 177.2

LC/MS (method 2): $R_t$=3.97 min, [M+H]$^+$ calc. for $C_{22}H_{20}FN_2O_4$ 395.41. found 395.20.

Synthesis Example 2: 2-(4-(2-(3-Chloro-4-methoxyphenyl)-6,7-dihydro-5H-cyclopenta[d]pyrimidin-4-yloxy)phenyl)acetic acid (compound no. 2)

A solution of the pyrimidine from 1c) (319 mg, 1 mmol), 3-chloro-4-methoxyphenyl boronic acid (187 mg, 1 mmol), caesium carbonate (391 mg, 1.2 mmol) and bis(triphenylphosphine)palladium(II) dichloride (5 mol %, 35 mg, 50 μmol) in dioxane/water (12 ml, 5:1) was refluxed for 1 h while stirring, 4N sodium hydroxide solution (0.5 ml) was added and the mixture was refluxed for a further hour while stirring. Then it was filtered and 2N hydrochloric acid (2 ml) and water (5 ml) were added. The precipitated deposit was separated off and washed with water and dichloromethane. White solid. Yield: 323 mg (78% of theory)

1H NMR (400 MHz, DMSO-d6, δ ppm): 2.14 (2H), 2.91 (t, J=7.5, 2H), 3.00 (t, J=7.8, 2H), 3.63 (s, 2H), 3.88 (s, 3H), 7.19 (d, J=8.8, 1H), 7.21 (d, J=8.5, 2H), 7.36 (d, J=8.5, 2H), 8.02 (dd, J=2.2, 8.7, 1H), 8.08 (d, J=2.1, 1H)

13C NMR (100 MHz, DMSO-d6, δ ppm): 21.5, 26.2, 39.9, 56.2, 66.3, 112.6, 117.9, 121.0, 121.2, 127.6, 128.7, 130.2, 130.3, 131.9, 150.9, 156.2, 160.7, 164.7, 172.5, 177.3

LC/MS (method 2): $R_t$=4.07 min, [M+H]$^+$ calc. for $C_{22}H_{20}ClN_2O_4$ 411.86. found 411.20.

Synthesis Example 3: 2-(4-(2-(3,4-Difluorophenyl)-6,7-dihydro-5H-cyclopenta[d]pyrimidin-4-yloxy)phenyl)acetic acid (compound no. 3)

The target compound was produced from the pyrimidine obtained by procedure 1c) (319 mg, 1 mmol), 3,4-difluorophenyl boronic acid (158 mg, 1 mmol), potassium carbonate (207 mg, 1.5 mmol) and bis(triphenylphosphine)palladium (II) dichloride (5 mol %, 35 mg, 50 μmol) in an analogous manner to procedure 1d). Contrary thereto, the raw product was not subsequently purified over silica gel but was washed with water and dichloromethane. White solid. Yield: 275 mg (72% of theory)

$^1$H NMR (400 MHz, DMSO-d6, δ ppm): 2.15 (2H), 2.94 (t, J=7.5, 2H), 3.02 (t, J=7.8, 2H), 3.64 (s, 2H), 7.22 (d, J=8.5, 1H), 7.36 (d, J=8.5, 2H), 7.50 (m, 1H), 7.91-7.98 (2H), 12.34 (s, 1H)

$^{13}$C NMR (100 MHz, DMSO-d6, δ ppm): 21.5, 26.3, 33.7, 37.8, 66.3, 116.1 (d, $^2J_{C,F}$=18.7), 117.7 (d, $^2J_{C,F}$=17.4), 118.8, 121.2, 124.4 (dd, $^4J_{C,F}$=3.1, $^3J_{C,F}$=6.8), 130.4, 132.0, 134.5 (dd, $^4J_{C,F}$=3.6, $^3J_{C,F}$=6.1), 149.4 (dd, $^2J_{C,F}$=12.8, $^1J_{C,F}$=245.2), 150.8, 151.0 (dd, $^2J_{C,F}$=12.3, $^1J_{C,F}$=249.9), 160.0 (dd, $^5J_{C,F}$=1.4, $^4J_{C,F}$=2.5), 164.8, 172.5, 177.5

LC/MS (method 2): $R_t$=4.14 min, [M+H]$^+$ calc. for $C_{21}H_{17}F_2N_2O_3$ 383.37. found 383.20.

Synthesis Example 4: 4-(2-(3-Fluoro-4-methoxyphenyl)-6,7-dihydro-5H-cyclopenta[d]pyrimidin-4-yloxy)benzoic acid (compound no. 4)

4a) 4-(2-Chloro-6,7-dihydro-5H-cyclopenta[d]pyrimidin-4-yloxy)benzoic acid methyl ester 4-Hydroxybenzoic acid (1.80 g, 11.83 mmol) and caesium carbonate (4.50 g, 13.81 mmol) were added to a solution of the dichlorine compound from 1b) (2.30 g, 12.17 mmol) in DMF (6 ml). It was then stirred for 1 h at 130° C. The mixture was cooled, water was added and extraction was performed with dichloromethane. The combined organic phases were dried with sodium sulfate and concentrated to small volume under vacuum until dry. The remaining brown solid (2.87 g) was suspended in methanol, stirred for 1 h, filtered, washed with methanol and dried. Yellow solid. Yield: 2.35 g (81% of theory)

13C-NMR (101 MHz, DMSO-d6, δ ppm): 22.0, 26.4, 34.2, 52.2, 119.7, 121.2, 127.5, 131.3, 155.8, 158.2, 165.2, 166.3, 178.8

4b) 4-(2-(3-Fluoro-4-methoxyphenyl)-6,7-dihydro-5H-cyclopenta[d]pyrimidin-4-yloxy)benzoic acid methyl ester PdCl$_2$(dppf) (81.7 mg, 0.1 mmol) was added under argon to the chlorine compound from procedure 4a) (304.7 mg, 1 mmol), 3-fluoro-4-methoxyphenyl boronic acid (178.8 mg, 1.05 mmol) and caesium carbonate (1.3 g, 4 mmol) in dioxane (4 ml) and the mixture was stirred for 2 h at 95° C. Then the reaction mixture (brown oil) was purified by chromatography [cyclohexane, then dichloromethane/cyclohexane 1:1]. White solid. Yield: 226 mg (57% of theory)

13C-NMR (101 MHz, CDCl3, δ ppm): 22.1, 26.8, 34.5, 52.2, 56.2, 112.7, 112.7, 115.6, 115.9, 118.3, 121.2, 121.4, 124.5, 124.5, 126.9, 130.4, 131.1, 131.4, 149.7, 149.8, 151.0, 153.4, 156.6, 162.2, 164.7, 166.5, 177.6

4c) 4-(2-(3-Fluoro-4-methoxyphenyl)-6,7-dihydro-5H-cyclopenta[d]pyrimidin-4-yloxy)benzoic acid 1N sodium hydroxide solution (1.8 ml) was added to a solution of the ester from 4b) (226 mg, 0.57 mmol) in methanol (5.5 ml) and dioxane (3.3 ml) and the mixture was stirred for 0.5 h at 95° C. 1N hydrochloric acid (1.8 ml) was added to the reaction mixture and the precipitated solid was filtered, washed with water and methanol and dried. Light-brown solid. Yield: 157 mg (72% of theory)

13C-NMR (101 MHz, DMSO-d6, δ ppm): 21.5, 26.2, 33.8, 56.1, 113.6, 114.3, 114.5, 118.2, 121.6, 124.3, 124.3, 127.7, 129.7, 129.8, 130.9, 149.1, 149.3, 150.0, 152.4, 155.9, 161.0, 161.0, 164.3, 166.7, 177.8

Synthesis Example 5: 4-(2-(3-Chloro-4-methoxyphenyl)-6,7-dihydro-5H-cyclopenta[d]pyrimidin-4-yloxy)benzoic acid (compound no. 5)

5a) 4-(2-(3-Chloro-4-methoxyphenyl)-6,7-dihydro-5H-cyclopenta[d]pyrimidin-4-yloxy)benzoic acid methyl ester The chlorine compound from 4a) (304.7 mg, 1 mmol) and 3-chloro-4-methoxyphenyl boronic acid (147.2 mg, 0.79 mmol) were reacted in an analogous manner to procedure 4b). White solid. Yield: 166 mg (51% of theory)

13C-NMR (101 MHz, CDCl3, δ ppm): 22.1, 26.8, 34.4, 52.1, 56.2, 111.5, 118.3, 121.4, 122.6, 126.9, 127.9, 130.7, 131.1, 156.6, 156.8, 162.1, 164.7, 166.5, 177.7

5b) 4-(2-(3-Chloro-4-methoxyphenyl)-6,7-dihydro-5H-cyclopenta[d]pyrimidin-4-yloxy)benzoic acid The target compound was produced from the ester obtained in 5a) (161.3 mg, 0.39 mmol) in an analogous manner to procedure 4c) by treatment with 1N sodium hydroxide solution. Light-brown solid. Yield: 115 mg (74% of theory); melting point: 220-225° C.

13C-NMR (101 MHz, CDCl3, δ ppm): 21.5, 26.3, 33.5, 54.6, 111.4, 118.6, 120.9, 122.2, 127.7, 129.3, 131.0, 156.0, 156.8, 161.4, 164.7, 167.8, 176.5

Synthesis Example 6: 4-(2-(3,4-Difluorophenyl)-6,7-dihydro-5H-cyclopenta[d]pyrimidin-4-yloxy)benzoic acid (compound no. 6)

6a) 4-(2-(3,4-Difluorophenyl)-6,7-dihydro-5H-cyclopenta[d]pyrimidin-4-yloxy)benzoic acid methyl ester Produced from the chlorine compound from 4a) (304.7 mg, 1 mmol) and 3,4-difluorophenyl boronic acid (165.8 mg, 1.05 mmol) in an analogous manner to procedure 4b). The reaction mixture (brown oil) thus obtained was purified by chromatography [cyclohexane; dichloromethane/cyclohexane 1:1]. White solid. Yield: 140 mg (37% of theory)

13C-NMR (101 MHz, CDCl3, δ ppm): 22.1, 26.8, 34.4, 52.2, 117.0, 117.2, 117.2, 119.0, 121.2, 121.4, 124.4, 124.4, 124.4, 124.5, 127.1, 131.1, 131.2, 134.4, 149.0, 149.2, 150.7, 150.9, 151.5, 151.6, 153.2, 153.4, 156.4, 161.4, 164.8, 166.5, 177.8

6b) 4-(2-(3,4-Difluorophenyl)-6,7-dihydro-5H-cyclopenta[d]pyrimidin-4-yloxy)benzoic acid The target compound was produced from the ester obtained in 6a) in an analogous manner to procedure 4c) by treatment with 1N sodium hydroxide solution. Light-brown solid. Yield: 66.5 mg (49% of theory); melting point: 240-244° C.

13C-NMR (101 MHz, DMSO-d6, δ ppm): 21.5, 26.3, 33.8, 116.0, 116.2, 117.7, 117.9, 119.2, 121.5, 124.4, 124.5, 124.5, 127.8, 131.0, 134.3, 134.4, 134.4, 134.4, 148.1, 148.2, 149.7, 149.8, 150.6, 152.3, 155.8, 160.1, 164.3, 166.7, 178.0

Synthesis Example 7: 2-(4-(2-(5-Chlorothiophen-2-yl)-6,7-dihydro-5H-cyclopenta[d]pyrimidin-4-yloxy)phenyl)acetic acid (compound no. 7)

7a) 2-(4-(2-(5-Chlorothiophen-2-yl)-6,7-dihydro-5H-cyclopenta[d]pyrimidin-4-yloxy)phenyl)acetic acid methyl ester 4-Chloro-2-(5-chlorothiophen-2-yl)-6,7-dihydro-5H-cyclopenta[d]pyrimidine (200 mg, 0.738 mmol) and 2-(4-hydroxyphenyl)acetic acid methyl ester (123 mg, 0.738 mmol) and potassium carbonate (306 mg, 2.213 mmol) in DMF (4 ml) were stirred for 18 h at 70° C. After adding water and ethyl acetate the organic phase was separated off and washed successively with water and saturated sodium chloride solution and dried with magnesium sulfate. The solvent was distilled off under vacuum and the residue purified by chromatography [hexane/ethyl acetate 0-20%]. White solid. Yield: 160 mg (54% of theory)

LC-MS (method 1): $R_t$=2.98 min, m/z [M+H]$^+$=401 (ES$^+$)

7b) 2-(4-(2-(5-Chlorothiophen-2-yl)-6,7-dihydro-5H-cyclopenta[d]pyrimidin-4-yloxy)phenyl)acetic acid Aqueous 1M lithium hydroxide solution (0.8 ml) was added to the product from procedure 7a) (160 mg, 0.399 mmol) in THF (5 ml) and water (1 ml) and it was stirred for 1 h at 55° C. and then overnight at room temperature. Then the THF was distilled off and the reaction mixture acidified with acetic acid. The precipitated solid was filtered off, washed with water and dried under vacuum. White solid. Yield: 143 mg (93% of theory)

LC-MS (method 1): $R_t$=2.58 min, m/z [M+H]$^+$=387 (ES$^+$), [M−H]$^-$=385 (ES$^-$)

Synthesis Example 8: 4-(2-(5-Chlorothiophen-2-yl)-6,7-dihydro-5H-cyclopenta[d]pyrimidin-4-yloxy)benzoic acid (compound no. 8)

8a) 4-(2-(5-Chlorothiophen-2-yl)-6,7-dihydro-5H-cyclopenta[d]pyrimidin-4-yloxy)benzoic acid methyl ester Produced from 4-chloro-2-(5-chlorothiophen-2-yl)-6,7-dihydro-5H-cyclopenta[d]pyrimidine (200 mg, 0.738 mmol)

and 4-hydroxybenzoic acid methyl ester (112 mg, 0.738 mmol) in an analogous manner to procedure 7a). Light-yellow solid. Yield: 130 mg (46% of theory); mass spectroscopy: [M+H]$^+$=387 (ES$^+$)

LC-MS (method 1): R$_t$=3.10 min, m/z [M+H]$^+$=387 (ES$^+$)

8b) 4-(2-(5-Chlorothiophen-2-yl)-6,7-dihydro-5H-cyclopenta[d]pyrimidin-4-yloxy)benzoic acid The methyl ester obtained in 8a) (150 mg, 0.388 mmol) was converted to the target compound in an analogous manner to procedure 7b). White solid. Yield: 100 mg (69% of theory)

LC-MS (method 1): R$_t$=2.58 min, m/z [M+H]$^+$=373 (ES$^+$), [M−H]$^-$=371 (ES$^-$)

Synthesis Example 9: 2-(4-(2-(5-Chlorothiophen-2-yl)-5,6,7,8-tetrahydroquinazolin-4-yloxy)phenyl) acetic acid (compound no. 10)

9a) 2-(4-(2-Chloro-5,6,7,8-tetrahydroquinazolin-4-yloxy)phenyl)acetic acid methyl ester 2,4-Dichloro-5,6,7,8-tetrahydroquinazoline (300 mg, 1.477 mmol), 2-(4-hydroxyphenyl)acetic acid methyl ester (245 mg, 1.477 mmol) and potassium carbonate (408 mg, 2.95 mmol) in DMF (4 ml) were stirred for 1 h at 80° C. After adding water the precipitated solid was filtered off, washed with water and dried under vacuum. White solid. Yield: 441 mg (90% of theory)

LC-MS (method 1): R$_t$=2.43 min, m/z [M+H]$^+$=333 (ES$^+$)

9b) 2-(4-(2-(5-Chlorothiophen-2-yl)-5,6,7,8-tetrahydroquinazolin-4-yloxy)phenyl)acetic acid A solution of caesium carbonate (648 mg, 1.988 mmol) in water (1 ml) was added to the chlorine compound from 9a) (441 mg, 1.325 mmol) and 5-chlorothiophen-2-yl boronic acid (473 mg, 2.92 mmol) in acetonitrile (3 ml). Tetrakis (triphenylphosphine)palladium(0) (77 mg, 0.066 mmol) was added under a nitrogen atmosphere and the mixture was heated to 150° C. for 3 h under microwave radiation (15 watts). Then 1M hydrochloric acid (3 ml) and ethyl acetate were added and the aqueous phase was extracted with ethyl acetate. The combined organic phases were concentrated to small volume under vacuum and then purified by column chromatography [silica gel, first rinsed with ethyl acetate/1% acetic acid prior to equilibration with hexane. Eluent=hexane/ethyl acetate 0-100%]. Light-yellow solid. Yield: 86 mg (16% of theory)

LC-MS (method 1): R$_t$=2.79 min, m/z [M+H]$^+$=401 (ES$^+$), [M−H]$^-$=399 (ES$^-$)

Synthesis Example 10: 4-(2-(5-Chlorothiophen-2-yl)-5,6,7,8-tetrahydroquinazolin-4-yloxy)benzoic acid (compound no. 11)

10a) 4-(2-Chloro-5,6,7,8-tetrahydroquinazolin-4-yloxy)benzoic acid methyl ester The compound was produced in an analogous manner to procedure 9a) from 2,4-dichloro-5,6,7,8-tetrahydroquinazoline (300 mg, 1.477 mmol) and 4-hydroxybenzoic acid methyl ester (225 mg, 1.477 mmol). Yield: 436 mg (93% of theory)

LC-MS (method 1): R$_t$=2.50 min, m/z [M+H]$^+$=319 (ES$^+$)

10b) 4-(2-(5-Chlorothiophen-2-yl)-5,6,7,8-tetrahydroquinazolin-4-yloxy)benzoic acid methyl ester A solution of tributyl(5-chlorothiophen-2-yl)stannane (384 mg, 0.941 mmol) in DMF (3 ml) was added to 4-(2-chloro-5,6,7,8-tetrahydroquinazolin-4-yloxy)benzoic acid methyl ester (200 mg, 0.627 mmol) and bis(triphenylphosphine)palladium(II) chloride (22 mg, 0.031 mmol). Then nitrogen was introduced into the solution for 5 min and it was then stirred for 3 h at 90° C. After adding ethyl acetate and water the organic phase was separated off and washed successively with water and saturated sodium chloride solution, dried with magnesium sulfate and concentrated to small volume. The residue was purified by chromatography [silica gel, hexane/ethyl acetate 0-30%]. Light-yellow solid, which was able to be reacted further with no additional purification. Yield: 128 mg (90% purity)

LC-MS (method 1): R$_t$=3.24 min, m/z [M+H]$^+$=400 (ES$^+$)

10c) 4-(2-(5-Chlorothiophen-2-yl)-5,6,7,8-tetrahydroquinazolin-4-yloxy)benzoic acid The methyl ester obtained from the previous reaction (128 mg, 90%, 0.128 mmol) was converted to the target compound in an analogous manner to procedure 7b). Yield: 23 mg (21% of theory)

LC-MS (method 1): R$_t$=2.86 min, m/z [M+H]$^+$=387 (ES$^+$), [M−H]$^-$=385 (ES$^-$)

Synthesis Example 11: 2-(4-((2-(5-Chlorothiophen-2-yl)-6,7-dihydro-5H-cyclopenta[d]pyrimidin-4-yl) methyl)phenyl)acetic acid (compound no. 9)

11a) 2-(4-((2-(5-Chlorothiophen-2-yl)-6,7-dihydro-5H-cyclopenta[d]pyrimidin-4-yl)methyl)phenyl) acetic acid methyl ester Iodine (47 mg, 0.185 mmol) was added to a suspension of zinc dust (403 mg, 6.17 mmol) in DMF (0.4 ml). The initially yellow mixture loses its colour when heated. After cooling, 2-(4-(bromomethyl)phenyl)acetic acid methyl ester (250 mg, 1.028 mmol) dissolved in DMF (0.6 ml) was added, resulting in a further temperature rise. After cooling again, a suspension of 4-chloro-2-(5-chlorothiophen-2-yl)-6,7-dihydro-5H-cyclopenta[d]pyrimidine (279 mg, 1.028 mmol), tetrakis(triphenylphosphine)palladium(0) (119 mg, 0.103 mmol) in DMF (2 ml) was added and stirred for 1 h at room temperature, then for 3 h at 55° C. and subsequently overnight at room temperature. The reaction mixture was acidified with 1M hydrochloric acid and ethyl acetate and water were added. The organic phase was separated off, washed successively with water and saturated sodium chloride solution and dried with magnesium sulfate. After distilling off the solvent the residue was purified by chromatography, first over a silica gel [hexane/ethyl acetate 0-50%] and then over an SCX column. White solid. Yield: 52 mg (12% of theory)

LC-MS (method 1): R$_t$=2.99 min, m/z [M+H]$^+$=399 (ES$^+$)

11b) 2-(4-((2-(5-Chlorothiophen-2-yl)-6,7-dihydro-5H-cyclopenta[d]pyrimidin-4-yl)methyl)phenyl) acetic acid Produced in an analogous manner to procedure 7b) from 2-(4-((2-(5-chlorothiophen-2-yl)-6,7-dihydro-5H-cyclopenta[d]pyrimidin-4-yl)methyl)phenyl)acetic acid methyl ester (64 mg, 0.160 mmol). Yield: 51 mg (83% of theory)

LC-MS (method 1): $R_t$=2.55 min, m/z [M+H]$^+$=385 (ES$^+$), [M−H]$^-$=383 (ES$^-$)

Synthesis Example 12: 2-(4-(2-(5-Chlorothiophen-2-yl)-6,6-difluoro-5,6,7,8-tetrahydroquinazolin-4-yloxy)phenyl)acetic acid (compound no. 12)

12a) 5,5-Difluoro-2-hydroxycyclohex-1-ene carboxylic acid ethyl ester 4,4-Difluoroheptanedicarboxylic acid diethyl ester (2.50 g, 9.91 mmol) was added to a suspension of potassium ethanolate (1.25 g, 14.86 mmol) in THF (10 ml) and the mixture was refluxed for 1 h while stirring. 1N hydrochloric acid (20 ml) and saturated sodium chloride solution were added to the reaction mixture and extraction was performed with diethyl ether. The combined organic phases were dried with magnesium sulfate, filtered and concentrated to small volume under vacuum. The residue was purified by column chromatography [silica gel 60, cyclohexane/ethyl acetate 19:1]. Colourless oil. According to the NMR spectrum the compound was predominantly in the enol form. Yield: 1.40 g (69% of theory)

13C-NMR (101 MHz, DMSO-d6, δ ppm): 13.9, 26.4, 26.5, 26.5, 28.2, 28.5, 28.7, 31.1, 31.3, 31.6, 60.6, 93.0, 93.0, 93.1, 120.1, 122.5, 124.8, 168.1, 169.7, 170.9, 202.5, 202.5

12b) 2-(5-Chlorothiophen-2-yl)-6,6-difluoro-5,6,7,8-tetrahydroquinazolin-4(3H)-one A suspension of the ethyl ester from 12a) (1.16 g, 5.63 mmol), 5-chlorothiophene-2-carboximidamide (741 mg, 3.75 mmol) and caesium carbonate (1.47 g, 4.50 mmol) in DMF (4 ml) was stirred for 1 h at 130° C. (oil bath temperature). Saturated sodium chloride solution was added to the reaction mixture and extraction was performed with THF. A beige solid was precipitated from the two-phase solution, which was filtered off, washed with water and THF and then discarded. The combined organic phases were dried with magnesium sulfate, filtered and evaporated under vacuum. The residue (790 mg) was purified by column chromatography [silica gel 60, cyclohexane/ethyl acetate 4:1→1:1]. White solid. Yield: 367 mg (32% of theory)

LC-MS (method 2): $R_t$=3.8 min, [M+H]$^+$=303.1

12c) 2-(4-(2-(5-Chlorothiophen-2-yl)-6,6-difluoro-5,6,7,8-tetrahydroquinazolin-4-yloxy)phenyl)acetic acid methyl ester BOP (452 mg, 1.02 mmol) and caesium carbonate (660 mg, 2.04 mmol) were added to the product from 12b) (155 mg, 0.51 mmol) in THF (3 ml) under an argon atmosphere and the mixture was stirred for 1 h at room temperature. 2-(4-Hydroxyphenyl)acetic acid methyl ester (169 mg, 1.02 mmol) and further caesium carbonate (660 mg, 2.04 mmol) were added to the colourless suspension. Then the mixture was stirred for 1 h at room temperature and water and ethyl acetate were added. After separating off a non-soluble solid (educt) the aqueous phase was extracted with ethyl acetate. The combined organic phases were dried with magnesium sulfate, filtered and evaporated under vacuum. The residue was purified over a silica gel column [cyclohexane/ethyl acetate 4:1]. Colourless solid. Yield: 161 mg (70% of theory)

LC-MS (method 2): $R_t$=4.3 min, m/z: [M+H]$^+$=451.2

13C-NMR (101 MHz, DMSO-d6, δ ppm): 28.9, 29.0, 29.1, 29.4, 30.8, 31.1, 31.1, 31.2, 39.4, 51.7, 110.3, 110.3, 110.4, 120.7, 121.5, 122.9, 125.1, 128.3, 131.6, 132.3, 140.6, 150.7, 156.4, 164.5, 166.4, 171.6

12d) 2-(4-(2-(5-Chlorothiophen-2-yl)-6,6-difluoro-5,6,7,8-tetrahydroquinazolin-4-yloxy)phenyl)acetic acid 1N sodium hydroxide solution (1.05 ml, 1.05 mmol) was added to a suspension of the methyl ester from 12c) (148 mg, 0.33 mmol) in methanol (5 ml) and the mixture was stirred for 16 h at room temperature. The reaction mixture was filtered and 1N hydrochloric acid (1.05 ml) was added to the filtrate. The precipitated deposit was separated off, washed with water and diethyl ether and then dried under vacuum. White solid. Yield: 56 mg (39% of theory)

LC-MS (method 2): $R_t$=4.2 min, m/z: [M+H]$^+$=437.1

13C-NMR (101 MHz, DMSO-d6, δ ppm): 29.0, 31.1, 39.9, 110.4, 120.3, 121.1, 121.3, 122.7, 125.1, 128.3, 128.4, 130.4, 132.3, 132.3, 140.6, 150.6, 156.4, 164.4, 166.4, 172.6

Synthesis Example 13: 2-(4-(2-(3-Chloro-4-hydroxyphenyl)-6,7-dihydro-5H-cyclopenta[d]pyrimidin-4-yloxy)phenyl)acetic acid (compound no. 13)

13a) 2-(4-(2-(3-Chloro-4-hydroxyphenyl)-6,7-dihydro-5H-cyclopenta[d]pyrimidin-4-yloxy)phenyl) acetic acid methyl ester A solution of the pyrimidine from 1c) (319 mg, 1.5 mmol), 3-chloro-4-hydroxyphenyl boronic acid (260 mg, 1.8 mmol), potassium phosphate (450 mg, 2.25 mmol) and bis(triphenylphosphine)palladium(II) dichloride (5 mol %, 54 mg, 75 μmol) in dioxane/water (18 ml, 5:1) was stirred for 1 h at 70° C. Then further boronic acid (259 mg, 1.5 mmol) was added and the mixture was stirred again for 1 h at 70° C. Water was added to the reaction mixture and extraction was performed with ethyl acetate. The combined organic phases were dried with magnesium sulfate, the solvent was removed and the residue was purified by column chromatography [cyclohexane/ethyl acetate 6:1]. Colourless solid. Yield: 222 mg (36% of theory).

1H NMR (400 MHz, CDCl3, δ ppm): 2.20 (2H), 2.97 (t, J=7.5, 2H), 3.07 (t, J=7.8, 2H), 3.69 (s, 2H), 3.73 (s, 3H), 5.80 (s, 1H), 7.00 (d, J=8.6, 1H), 7.17 (d, J=8.5, 2H), 7.34 (d, J=8.5, 2H), 8.04 (dd, J=2.0, 8.6, 1H), 8.23 (d, J=2.0, 1H)

LC/MS (method 2): $R_t$=4.01 min, [M+H]$^+$ calc. for $C_{22}H_{20}ClN_2O_4$ 411.86. found 411.20.

13b) 2-(4-(2-(3-Chloro-4-hydroxyphenyl)-6,7-dihydro-5H-cyclopenta[d]pyrimidin-4-yloxy)phenyl) acetic acid A 2N sodium hydroxide solution (1 ml) was added to a solution of the pyrimidine from 13a) (222 mg, 0.54 mmol) in methanol (4 ml) and the mixture was stirred for 12 h at room temperature. Then 2N hydrochloric acid (1 ml) and water (10 ml) were added. The precipitated deposit was filtered off, washed with water and dried. Colourless solid. Yield: 140 mg (65% of theory)

1H NMR (400 MHz, DMSO-d6, δ ppm): 2.12 (2H), 2.90 (t, J=7.4, 2H), 2.97 (t, J=7.7, 2H), 3.63 (s, 2H), 6.97 (d, J=8.5, 1H), 7.20 (d, J=8.5, 2H), 7.38 (d, J=8.5, 2H), 7.88 (dd, J=2.1, 8.5, 1H), 8.01 (ddd, J=2.1, 1H), 11.08 (s, 1H)

13C NMR (100 MHz, DMSO-d6, δ ppm): 21.4, 26.2, 33.7, 39.9, 116.4, 117.5, 119.7, 121.1, 127.4, 129.0, 129.1, 130.3, 131.9, 150.9, 155.2, 161.1, 164.6, 172.6, 177.2

LC/MS (method 2): $R_t$=3.87 min, [M+H]$^+$ calc. for $C_{21}H_{18}ClN_2O_4$ 397.83. found 397.20.

Synthesis Example 14: 2-(4-(2-(3-Bromo-4-methoxyphenyl)-6,7-dihydro-5H-cyclopenta[d]pyrimidin-4-yloxy)phenyl)acetic acid (compound no. 14)

14a) 2-(4-(2-(4-Hydroxyphenyl)-6,7-dihydro-5H-cyclopenta[d]pyrimidin-4-yloxy)phenyl)acetic acid methyl ester A solution of 2-(4-(2-chloro-6,7-dihydro-5H-cyclopenta[d]pyrimidin-4-yloxy)phenyl)acetic acid methyl ester (2.00 g, 6.27 mmol), 4-hydroxyphenyl boronic acid (1.73 g, 12.5 mmol), potassium phosphate (2.70 g, 12.5 mmol) and tetrakis(triphenylphosphine)palladium(0) (5 mol %, 362 mg, 0.31 mmol) in dioxane/water (60 ml, 5:1) was stirred for 1.5 h at 70° C. Then saturated sodium chloride solution was added to the reaction mixture and the aqueous phase was extracted with ethyl acetate. The combined organic phases were dried with magnesium sulfate, the solvent was removed and the residue was purified by column chromatography [silica gel 60; cyclohexane/ethyl acetate 3:1]. Colourless solid. Yield: 2.25 g (95% of theory)

1H NMR (400 MHz, DMSO-d6, δ ppm): 2.09 (2H), 2.89 (t, J=7.5, 2H), 2.97 (t, J=7.8, 2H), 3.65 (s, 3H), 3.75 (s, 2H), 6.75 (d, J=8.5, 2H), 7.21 (d, J=8.5, 2H), 7.35 (d, J=8.5, 2H), 7.93 (d, J=8.5, 2H), 9.84 (s, 1H)

LC/MS (method 2): $R_t$=3.83 min, [M+H]$^+$ calc. for $C_{22}H_{20}N_2O_4$ 377.42. found 377.20.

14b) 2-(4-(2-(3-Bromo-4-hydroxyphenyl)-6,7-dihydro-5H-cyclopenta[d]pyrimidin-4-yloxy)phenyl) acetic acid methyl ester Aluminium chloride (334 mg, 2.5 mmol) was added to the intermediate from 14a) (940 mg, 2.5 mmol) in dichloromethane (10 ml) and the mixture was stirred for 0.5 h at room temperature, during which time the suspension converted to a solution. Bromine (0.128 ml, 2.5 mmol) was added slowly, the mixture was stirred overnight, then 1N sodium thiosulfate solution (40 ml) was added slowly and the mixture was stirred for a further 15 min. The aqueous phase was extracted with ethyl acetate and the combined organic phases were dried with magnesium sulfate. The solvent was removed and the residue was purified by column chromatography [silica gel 60; cyclohexane/ethyl acetate 3:1]. White solid. Yield: 935 mg (82% of theory)

1H NMR (400 MHz, DMSO-d6, δ ppm): 2.10 (2H), 2.88 (t, J=7.5, 2H), 2.96 (t, J=7.8, 2H), 3.64 (s, 3H), 3.74 (s, 2H), 6.95 (d, J=8.5, 1H), 7.20 (d, J=8.5, 2H), 7.37 (d, J=8.5, 2H), 7.90 (dd, J=2.1, 8.5, 1H), 8.18 (d, J=2.1, 1H), 10.72 (s, 1H)

LC/MS (method 2): $R_t$=4.02 min, [M]$^+$ calc. for $C_{22}H_{19}BrN_2O_4$ 455.11. found 455.31.

14c) 2-(4-(2-(3-Bromo-4-methoxyphenyl)-6,7-dihydro-5H-cyclopenta[d]pyrimidin-4-yloxy)phenyl) acetic acid methyl ester A solution of the pyrimidine from 14b) (1.35 g, 3 mmol), potassium carbonate (415 mg, 3 mmol) and iodomethane (0.169 ml, 2.7 mmol) in DMF (10 ml) was stirred for 2 h at room temperature. Water was added to the reaction mixture and the aqueous phase was extracted with dichloromethane. The combined organic phases were dried with magnesium sulfate and freed from solvent. Purification of the residue by column chromatography [silica gel 60; cyclohexane/ethyl acetate 5:1] yielded the target compound as a colourless solid. Yield: 840 mg (66% of theory)

1H NMR (400 MHz, CDCl3, δ ppm): 2.19 (2H), 2.96 (t, J=7.5, 2H), 3.05 (t, J=7.8, 2H), 3.73 (s, 3H), 3.91 (s, 2H), 6.87 (d, J=8.5, 1H), 7.19 (d, J=8.5, 2H), 7.34 (d, J=8.5, 2H), 8.13 (dd, J=2.1, 8.5, 1H), 8.44 (d, J=2.1, 1H)

LC/MS (method 2): $R_t$=4.22 min, [M]$^+$ calc. for $C_{23}H_{21}BrN_2O_4$ 469.34. found 469.20.

14d) 2-(4-(2-(3-Bromo-4-methoxyphenyl)-6,7-dihydro-5H-cyclopenta[d]pyrimidin-4-yloxy)phenyl) acetic acid A 1N sodium hydroxide solution (5 ml) was added to the methyl ester from 14c) (469 mg, 1 mmol) in THF (20 ml) and the mixture was stirred overnight at room temperature. Then 2N hydrochloric acid (2.5 ml) was added, the THF was distilled off and the precipitate was filtered off. This was washed with water and then dried. White solid. Yield: 384 mg (84% of theory); melting point: 263-264° C.

1H NMR (400 MHz, DMSO-d6, δ ppm): 2.12 (m, 2H), 2.90 (dd (t-type), J=7.4, 7.5, 2H), 2.96 (dd (t-type), J=7.7, 7.8, 2H), 3.63 (s, 2H), 3.87 (s, 3H), 7.14 (d, J=8.7, 1H), 7.22 (d, J=8.5, 2H), 7.36 (d, J=8.5, 2H), 8.04 (dd, J=2.1, 8.7, 1H), 8.25 (d, J=2.1, 1H)

13C NMR (100 MHz, DMSO-d6, δ ppm): 21.4, 26.3, 33.7, 40.0, 56.4, 110.5, 112.4, 117.9, 121.2, 128.3, 130.3, 130.7, 131.8, 132.0, 150.9, 157.1, 160.6, 164.7, 172.6, 177.3

LC/MS (method 2): $R_t$=4.09 min, [M]$^+$ calc. for $C_{22}H_{19}BrN_2O_4$ 455.31. found 455.10.

Synthesis Example 15: 2-[4-[[2-(5-Fluoro-thiophen-2-yl)-6,6-dioxo-5,7-dihydro-thieno[3,4-d]pyrimidin-4-yl]oxy]-phenyl]-acetic acid

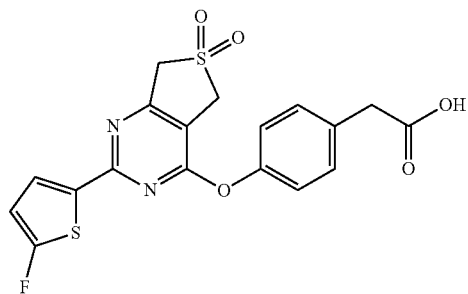 [SMILES: O=C(O)Cc1ccc(Oc2nc(-c3ccc(F)s3)nc3c2CS(=O)(=O)C3)cc1]

15a) 2-(5-Fluorothiophen-2-yl)-5,7-dihydrothieno[3,4-d]pyrimidin-4-ol

A solution of methyl 4-oxotetrahydrothiophene-3-carboxylate (1.42 g, 8.84 mmol), 5-fluorothiophene-2-carboximidamide hydrochloride (800 mg, 4.42 mmol) and Hünig base (0.9 ml, 680 mg, 5.3 mmol) in n-propanol (13 ml) was irradiated with microwaves at 90° C. for 18 h. The mixture was cooled to room temperature, ethyl acetate (50 ml) was added and stirring was continued for 15 min under cooling with an ice bath. The solid which precipitated out was filtered off and washed with ethyl acetate (2×5 ml), ethanol (2×5 ml) and diethyl ether (2×5 ml). Light green solid. Yield: 689 mg (62% yield)

15b) 4-Chloro-2-(5-fluorothiophen-2-yl)-5,7-dihydrothieno[3,4-d]pyrimidine

The thioether of 15a) (689 mg, 2.7 mmol) and phosphorous oxychloride (5.05 ml, 8.3 g, 54.2 mmol) were heated for 2 h at 95° C. The reaction mixture was cooled with an ice bath and water (30 ml) was slowly added. Dichloromethane (30 ml) was added, the mixture was stirred for further 10 min and the aqueous phase was then separated and extracted with dichloromethane (2×30 ml). The combined organic layers were dried over sodium sulfate and evaporated. Beige solid. Yield: 850 mg (99% of theory). Melting range: 119-124° C.

$^{13}$C-NMR (101 MHz, CDCl3, δ ppm): 33.4, 38.8, 109.3, 109.4, 127.3, 127.4, 129.5, 157.6, 160.6, 167.7, 170.6, 171.9

15c) Methyl 2-(4-(2-(5-fluorothiophen-2-yl)-5,7-dihydrothieno[3,4-d]pyrimidin-4-yloxy)phenyl)-acetate The pyrimidine chloride of 15b) (470 mg, 1.72 mmol), methyl 2-(4-hydroxyphenyl)acetate (567 mg, 3.45 mmol) and potassium carbonate (358 mg, 2.58 mmol) in dry acetonitrile (30 ml) were stirred for 16 h at 90° C. The reaction mixture was filtered and the filter washed with acetonitrile (2×5 ml) and dichloromethane (2×10 ml). The filtrate was evaporated and the residue purified by column chromatography [silica gel; ethyl acetate/cyclohexane 1:4]. Colorless solid. Yield: 540 mg (78% of theory)

$^{13}$C-NMR (101 MHz, CDCl3, δ ppm): 31.8, 38.7, 40.6, 52.1, 108.9, 109.0, 115.0, 121.7, 126.3, 126.3, 130.2, 130.6, 130.6, 131.2, 151.2, 160.0, 165.3, 167.2, 170.1, 171.8, 172.4

15d) Methyl 2-[4-[[2-(5-fluoro-thiophen-2-yl)-6,6-dioxo-5,7-dihydro-thieno[3,4-d]pyrimidin-4-yl]oxy]-phenyl]-acetate m-Chloroperoxybenzoic acid (77%, 824 mg, 3.34 mmol) in dichloromethane (10 ml) was added under cooling with an ice bath within 2 min to a solution of the product of 15c) (520 mg, 1.29 mmol) in dichloromethane (30 ml) and the mixture was stirred for 3 h at room temperature. Saturated sodium hydrogen carbonate solution (30 ml) was poured into the mixture and stirring was continued for 10 min. The organic phase was then separated, washed with saturated sodium hydrogen carbonate solution (30 ml), dried over sodium sulfate and evaporated. The residue was purified by column chromatography [silica gel; cyclohexane/ethyl acetate 1:1]. White solid. Yield: 437 mg (78% of theory). Melting range: 192-193° C.

$^{13}$C-NMR (101 MHz, CDCl3-d6, δ ppm): 40.5, 52.1, 53.6, 57.9, 109.0, 109.0, 109.4, 109.5, 121.7, 127.6, 127.7, 130.4, 131.9, 150.6, 160.7, 160.7, 161.8, 164.6, 167.9, 170.9, 171.7

15e) 2-[4-[[2-(5-Fluoro-thiophen-2-yl)-6,6-dioxo-5,7-dihydro-thieno[3,4-d]pyrimidin-4-yl]oxy]-phenyl]-acetic acid 1N sodium hydroxide solution (2.65 ml, 2.65 mmol) was added to the product obtained under 15d) (230 mg, 0.53 mmol) in THF (15 ml) and the mixture was stirred for 16 h at room temperature. The solvent was removed in vacuo and water (10 ml) and 1N hydrochloric acid (3 ml) were added. After stirring for 3 h at room temperature, the precipitate was filtered off and washed with water (2×6 ml). Yield: 210 mg (94% of theory). Melting range: 195-197° C.

$^{13}$C-NMR (101 MHz, DMSO-d6, δ ppm): 30.4, 40.7, 52.7, 57.1, 110.4, 110.5, 121.1, 127.1, 127.1, 129.6, 129.9, 129.9, 133.4, 150.0, 158.8, 163.1, 164.1, 166.0, 168.9, 172.8

Synthesis Example 16: 2-[4-[[2-(3-Fluoro-4-methoxy-phenyl)-6,6-dioxo-5,7-dihydro-thieno[3,4-d]pyrimidin-4-yl]oxy]-phenyl]-acetic acid

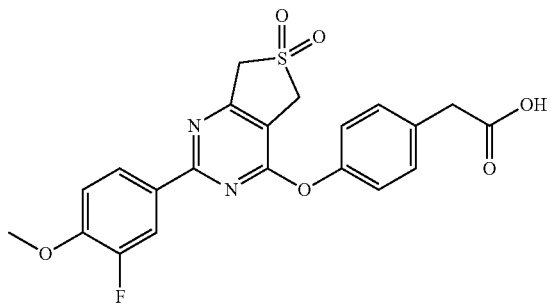 [SMILES: COc1ccc(-c2nc3c(c(Oc4ccc(CC(=O)O)cc4)n2)CS(=O)(=O)C3)cc1F]

16a) Methyl 2-(4-(2-(3-fluoro-4-methoxyphenyl)-5,7-dihydrothieno[3,4-d]pyrimidin-4-yloxy)phenyl) acetate The compound was obtained from 4-chloro-2-(3-fluoro-4-methoxyphenyl)-5,7-dihydrothieno[3,4-d]pyrimidine (313 mg, 1 mmol) and methyl 2-(4-hydroxyphenyl)acetate (329 mg, 2 mmol) according to the procedure described under 15c). Yellow oil. Yield: 250 mg (59% of theory)

$^{13}$C-NMR (101 MHz, CDCl3, δ ppm): 31.9, 38.8, 40.6, 52.1, 56.2, 112.7, 112.7, 115.1, 115.8, 116.0, 121.7, 124.6, 124.7, 130.0, 130.3, 131.2, 149.9, 150.0, 150.9, 151.3, 153.4, 162.9, 162.9, 165.5, 171.8, 172.5

16b) Methyl 2-[4-[[2-(3-fluoro-4-methoxy-phenyl)-6,6-dioxo-5,7-dihydro-thieno[3,4-d]pyrimidin-4-yl]oxy]-phenyl]-acetate Preparation according to the procedure described under 15d) starting with the product of 16a) (230 mg, 0.54 mmol). Yellow solid. Yield: 180 mg (73% of theory). Melting range: 200-202° C.

$^{13}$C-NMR (101 MHz, CDCl3-d6, δ ppm): 40.6, 52.1, 53.7, 56.2, 58.1, 109.3, 112.7, 112.8, 115.9, 116.1, 121.6, 125.0, 125.0, 129.2, 129.3, 130.5, 131.9, 150.6, 150.7, 150.7, 150.9, 161.9, 163.6, 163.7, 164.9, 171.7

16c) 2-[4-[[2-(3-Fluoro-4-methoxy-phenyl)-6,6-dioxo-5,7-dihydro-thieno[3,4-d]pyrimidin-4-yl]oxy]-phenyl]-acetic acid Obtained from the product of 16b) (180 mg, 0.39 mmol) in analogy to the procedure described under 15e).

Yield: 160 mg (93% of theory). Melting range: 204-206° C.

$^{13}$C-NMR (101 MHz, DMSO-d6, δ ppm): 30.4, 52.7, 56.2, 57.2, 110.5, 113.8, 114.6, 114.8, 121.4, 124.7, 124.8, 128.7, 128.8, 130.5, 132.6, 149.9, 150.0, 150.3, 152.4, 161.6, 161.7, 163.2, 164.3, 172.5

The following synthesis examples were prepared according to the procedures for the examples 15 and 16:

Synthesis Example 17: 2-[4-[[2-(3-Chloro-4-methoxy-phenyl)-6,6-dioxo-5,7-dihydro-thieno[3,4-d]pyrimidin-4-yl]oxy]-phenyl]-acetic acid

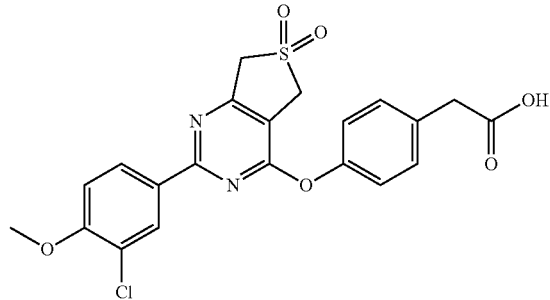 [SMILES: COc1ccc(-c2nc3c(c(Oc4ccc(CC(=O)O)cc4)n2)CS(=O)(=O)C3)cc1Cl]

17a) Preparation of methyl 2-(4-(2-(3-chloro-4-methoxy-phenyl)-5,7-dihydrothieno[3,4-d]pyrimidin-4-yloxy)phenyl)acetate as yellow solid from 4-chloro-2-(3-chloro-4-methoxyphenyl)-5,7-dihydrothieno[3,4-d]pyrimidine (148 mg, 0.47 mmol). Yield: 180 mg (87% of theory).

$^{13}$C-NMR (101 MHz, CDCl3, δ ppm): 31.9, 38.8, 40.2, 40.6, 52.0, 52.1, 56.2, 111.5, 115.2, 115.4, 121.7, 122.5, 126.1, 128.1, 130.2, 130.2, 130.4, 131.2, 151.3, 154.7, 157.1, 162.7, 165.5, 171.9, 172.4, 172.5

17b) Preparation of methyl 2-[4-[[2-(3-chloro-4-methoxy-phenyl)-6,6-dioxo-5,7-dihydro-thieno[3,4-d]pyrimidin-4-yl]oxy]-phenyl]-acetate as yellow solid. Yield: 110 mg (100% of theory). Melting range: 148-151° C.

$^{13}$C-NMR (101 MHz, CDCl3-d6, δ ppm): 40.6, 52.2, 53.7, 56.3, 58.1, 109.3, 111.6, 121.6, 122.8, 128.4, 129.5, 130.4, 130.5, 131.8, 150.7, 157.7, 161.9, 163.5, 164.9, 171.7

17c) Preparation of 2-[4-[[2-(3-chloro-4-methoxy-phenyl)-6,6-dioxo-5,7-dihydro-thieno[3,4-d]pyrimidin-4-yl]oxy]-phenyl]-acetic acid. Yield: 82 mg (77% of theory). Melting range: 210-212° C.

$^{13}$C-NMR (101 MHz, DMSO-d6, δ ppm): 30.4, 52.7, 56.4, 57.2, 110.5, 112.9, 121.3, 121.4, 128.1, 129.0, 129.1, 130.5, 132.7, 150.3, 157.0, 161.5, 163.3, 164.3, 172.5

Synthesis Example 18: 2-[4-[[2-(4-Methoxyphenyl)-6,6-dioxo-5,7-dihydro-thieno[3,4-d]pyrimidin-4-yl]oxy]-phenyl]-acetic acid

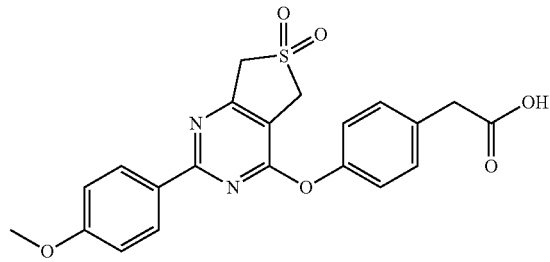 [SMILES: COc1ccc(-c2nc3c(c(Oc4ccc(CC(=O)O)cc4)n2)CS(=O)(=O)C3)cc1]

18a) Preparation of methyl 2-(4-(2-(4-methoxyphenyl)-5,7-dihydrothieno[3,4-d]pyrimidin-4-yloxy)phenyl)acetate as yellow solid. Yield: 80 mg (39% of theory).

18b) Preparation of methyl 2-[4-[[2-(4-methoxyphenyl)-6,6-dioxo-5,7-dihydro-thieno[3,4-d]pyrimidin-4-yl]oxy]-phenyl]-acetate as yellow oil. Yield: 110 mg (57% of theory)

$^{13}$C-NMR (101 MHz, CDCl3-d6, δ ppm): 40.5, 52.1, 53.7, 55.4, 55.5, 58.1, 108.7, 113.9, 121.7, 128.7, 130.2, 130.4, 130.6, 131.6, 150.9, 161.7, 162.5, 164.6, 164.8, 171.7

18c) Preparation of 2-[4-[[2-(4-Methoxyphenyl)-6,6-dioxo-5,7-dihydro-thieno[3,4-d]pyrimidin-4-yl]oxy]-phenyl]-acetic acid 1N sodium hydroxide solution (1.15 ml, 1.15 mmol) was added to the product of 18a) (110 mg, 0.23 mmol) in THF (10 ml) and the mixture was stirred for 16 h at room temperature meanwhile a solid precipitated. The supernatant was removed with a pipette and the precipitate was washed with THF (2×7 ml) and dichloromethane (2×7 ml). Water (10 ml) and 1N hydrochloric acid (1.5 ml) were added and the mixture was stirred for 3.5 h a room temperature. Filtration and subsequent washing of the filter residue with water (2×6 ml) provided the product as a solid. Yield: 82 mg (77% of theory). Melting range: 201-203° C.

$^{13}$C-NMR (101 MHz, DMSO-d6, δ ppm): 30.4, 52.7, 55.3, 57.3, 109.9, 114.1, 121.4, 128.3, 129.5, 130.5, 132.5, 150.4, 162.0, 162.8, 163.2, 164.3, 172.6

Synthesis Example 19: 2-(4-(2-(5-Chlorothiophen-2-yl)-5,7-dihydrothieno[3,4-d]pyrimidin-4-yloxy)phenyl)acetic acid

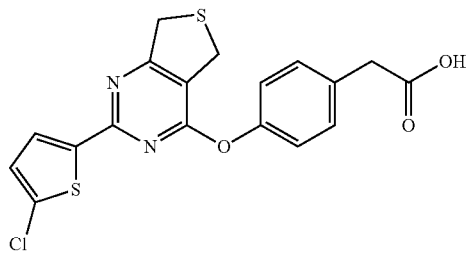 [SMILES: O=C(O)Cc1ccc(Oc2nc(-c3ccc(Cl)s3)nc3c2CSC3)cc1]

19a) 2-(5-Chlorothiophen-2-yl)-5,7-dihydrothieno[3,4-d]pyrimidin-4-ol

A mixture of methyl 4-oxotetrahydrothiophene-3-carboxylate (810 mg, 5.06 mmol), 5-chlorothiophene-2-carboximidamide (500 mg, 2.53 mmol) and Hünig base (0.515 ml, 392 mg, 3.03 mmol) in n-propanol (2 ml) was irradiated with microwaves for 16 h at 90° C. The reaction mixture was cooled to room temperature, diluted with ethyl acetate (10 ml) and stirred for 30 min under cooling with an ice bath. The precipitate was filtered off and washed with ethyl acetate (3 ml) and diethyl ether (3 ml). Beige solid. Yield: 343 mg (50% of theory)

$^{13}$C-NMR (101 MHz, DMSO-d6, δ ppm): 3.9 (2H, d, J=2.8), 4.1 (2H, d, J=3.2), 7.2 (1H, d, J=4.4), 8.0 (1H, d, J=3.6)

19b) 4-Chloro-2-(5-chlorothiophen-2-yl)-5,7-dihydrothieno[3,4-d]pyrimidine

The thioether of 19a) (321 mg, 1.18 mmol) and phosphorus oxychloride (2.2 ml, 3.69 g, 23.7 mmol) were heated for 2 h at 95° C. The reaction mixture was then cooled to 0° C. and water (15 ml) was slowly added. The mixture was diluted with dichloromethane (20 ml) and stirring was continued for 10 min. The aqueous phase was separated and extracted with dichloromethane (2×20 ml). The combined organic layers were dried over sodium sulfate and the solvents were distilled off in vacuo. Orange-colored solid. Yield: 312 mg (92% of theory). Melting range: 150-152° C.

$^{13}$C-NMR (101 MHz, CDCl3, δ ppm): 33.5, 38.8, 127.6, 127.7, 129.4, 135.5, 139.5, 157.7, 160.1, 172.0

19c) Methyl 2-(4-(2-(5-chlorothiophen-2-yl)-5,7-dihydrothieno[3,4-d]pyrimidin-4-yloxy)phenyl)-acetate Prepared from 4-chloro-2-(5-chlorothiophen-2-yl)-5,7-dihydrothieno[3,4-d]pyrimidine (150 mg, 0.52 mmol) and methyl 2-(4-hydroxyphenyl)acetate (155 mg, 0.936 mmol) in an analogous manner as described under 15c). Colorless solid. Yield: 174 mg (80% of theory). Melting range: 163-165° C.

$^{13}$C-NMR (101 MHz, CDCl3, δ ppm): 31.8, 38.6, 40.5, 52.0, 115.3, 121.6, 127.3, 128.4, 130.2, 131.2, 134.4, 140.7, 151.1, 159.5, 165.3, 171.8, 172.4

19d) 2-(4-(2-(5-Chlorothiophen-2-yl)-5,7-dihydrothieno[3,4-d]pyrimidin-4-yloxy)phenyl)acetic acid 1N sodium hydroxide solution (3.72 ml, 3.72 mmol) was added to 19c) (156 mg, 0,372 mmol) in methanol (35 ml) and the mixture was stirred for 24 h at room temperature. The solvents were removed in vacuo, dichloromethane (10 ml) and water (10 ml) were added and the suspension was stirred for 15 min and then filtrated. The precipitate and the aqueous phase were combined and stirred together with 1N hydrochloric acid (3.72 ml) for 3 h. Filtration and washing of the filter residue with water (2×5 ml) finally yielded the product. Beige solid. Yield: 90 mg (60% of theory)

$^{13}$C-NMR (101 MHz, DMSO-d6, δ ppm): 31.0, 37.6, 39.9, 115.7, 121.2, 128.4, 128.5, 130.3, 132.4, 132.5, 140.3, 150.4, 158.2, 164.9, 172.4, 172.5

Synthesis Example 20: 2-[4-[[2-(5-Chloro-thiophen-2-yl)-6-oxo-5,7-dihydro-thieno[3,4-d]pyrimidin-4-yl]oxy]-phenyl]-acetic acid

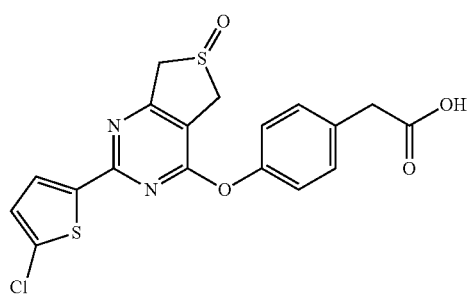 [SMILES: O=C(O)Cc1ccc(Oc2nc(-c3ccc(Cl)s3)nc3c2CS(=O)C3)cc1]

20a) Methyl 2-[4-[[2-(5-chloro-thiophen-2-yl)-6-oxo-5,7-dihydro-thieno[3,4-d]pyrimidin-4-yl]oxy]-phenyl]-acetate A solution of m-chloroperoxybenzoic acid (77%, 146 mg, 0.651 mmol) in dichloromethane (10 ml) was added within 10 min to the product of 19c) (238 mg, 0,592 mmol) in dichloromethane (15 ml) at 0° C. and the mixture was stirred for 2 h at this temperature. Saturated sodium hydrogen carbonate solution (20 ml) was added and stirring was continued for 30 min at room temperature. The organic phase was separated, washed with sodium hydrogen carbonate solution (20 ml), dried over sodium sulfate and evaporated. The residue was purified by column chromatography [silica gel 60; ethyl acetate]. Colorless solid. Yield: 214 mg (83% of theory). Melting range: 195-198° C.

$^{13}$C-NMR (101 MHz, CDCl3, δ ppm): 40.5, 52.1, 54.6, 60.7, 110.3, 121.6, 127.5, 129.0, 130.3, 131.5, 135.1, 140.2, 150.8, 160.9, 166.7, 168.3, 171.7

20b) 2-[4-[[2-(5-Chloro-thiophen-2-yl)-6-oxo-5,7-dihydro-thieno[3,4-d]pyrimidin-4-yl]oxy]-phenyl]-acetic acid Prepared from the ester of 20a) (214 mg, 0.492 mmol) in an analogous manner as described under 15e). Beige solid. Yield: 147 mg (71% of theory). Melting range: 169-172° C.

$^{13}$C-NMR (101 MHz, DMSO-d6, δ ppm): 39.9, 53.9, 60.2, 112.4, 121.2, 128.5, 128.8, 130.4, 132.5, 132.8, 140.1, 150.2, 159.1, 166.3, 170.1, 172.5

Synthesis Example 21: 2-[4-[[2-(5-Chloro-thiophen-2-yl)-6,6-dioxo-5,7-dihydro-thieno[3,4-d]pyrimidin-4-yl]oxy]-phenyl]-acetic acid

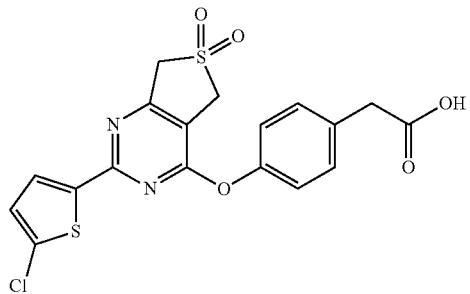 [SMILES: O=C(O)Cc1ccc(Oc2nc(-c3ccc(Cl)s3)nc3c2CS(=O)(=O)C3)cc1]

21a) Methyl 2-[4-[[2-(5-chloro-thiophen-2-yl)-6,6-dioxo-5,7-dihydro-thieno[3,4-d]pyrimidin-4-yl]oxy]-phenyl]-acetate The thioether of 19c) (200 mg, 0,477 mmol) was treated with m-chloroperoxybenzoic acid (77%, 305 mg, 1.34 mmol) in an analogous manner as described under 20a). Colorless solid. Yield: 159 mg (74% of theory). Melting range: 233-234° C.

$^{13}$C-NMR (101 MHz, CDCl3, δ ppm): 40.5, 52.1, 53.6, 57.9, 109.2, 121.5, 127.6, 129.6, 130.4, 131.9, 135.9, 139.8, 150.5, 160.2, 161.8, 164.6, 171.7

21b) 2-[4-[[2-(5-Chloro-thiophen-2-yl)-6,6-dioxo-5,7-dihydro-thieno[3,4-d]pyrimidin-4-yl]oxy]-phenyl]-acetic acid Prepared from the product of 21a) (136 mg, 0.3 mmol) in analogy to the procedure described in 18c). Yield: 82 mg (63% of theory). Melting range: 243-245° C.

$^{13}$C-NMR (101 MHz, DMSO-d6, δ ppm): 39.9, 52.6, 57.0, 110.8, 121.2, 128.6, 129.3, 130.5, 132.7, 133.3, 139.9, 150.1, 158.3, 163.2, 164.1, 172.5

Synthesis Example 22: 2-(4-(2-(5-Chlorothiophen-2-yl)-7,8-dihydro-5H-thiopyrano[4,3-d]pyrimidin-4-yloxy)phenyl)acetic acid

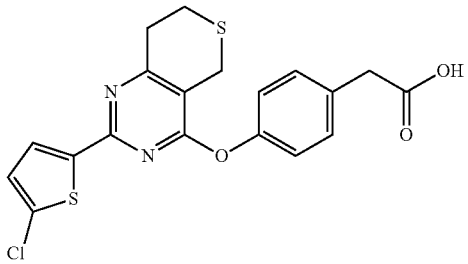 [SMILES: O=C(O)Cc1ccc(Oc2nc(-c3ccc(Cl)s3)nc3c2CSCC3)cc1]

22a) 2-(5-Chlorothiophen-2-yl)-7,8-dihydro-5H-thiopyrano[4,3-d]pyrimidin-4-ol Prepared from methyl 4-oxotetrahydro-2H-thiopyran-3-carboxylate (1.76 g, 10.15 mmol) and 5-chlorothiophene-2-carboximidamide hydrochloride (1.0 g, 5.07 mmol) in analogy to the procedure described in 19a). Colorless solid. Yield: 1.05 g (73% of theory). Melting range: 313-315° C.

22b) 4-Chloro-2-(5-chlorothiophen-2-yl)-7,8-dihydro-5H-thiopyrano[4,3-d]pyrimidine The target compound was obtained from 2-(5-chlorothiophen-2-yl)-7,8-dihydro-5H-thiopyrano[4,3-d]pyrimidin-4-ol (600 mg, 2.1 mmol) in an analogous manner to the procedure of 19b). Orange solid. Yield: 604 mg (95% of theory). Melting range: 158-161° C.
$^{13}$C-NMR (101 MHz, CDCl3, δ ppm): 25.1, 26.4, 34.0, 123.8, 127.6, 128.9, 135.0, 139.9, 157.8, 160.0, 166.9

22c) Methyl 2-(4-(2-(5-chlorothiophen-2-yl)-7,8-dihydro-5H-thiopyrano[4,3-d]pyrimidin-4-yloxy)phenyl)acetate Prepared from pyrimidine chloride of 22b) (285 mg, 0.94 mmol) and methyl 2-(4-hydroxyphenyl)acetate (281 mg, 1.69 mmol) in analogy to the procedure of 15c). Colorless solid. Yield: 267 mg (66% of theory). Melting point: 130° C.
$^{13}$C-NMR (101 MHz, CDCl3, δ ppm): 23.2, 25.3, 33.4, 40.5, 52.0, 112.7, 121.7, 127.2, 127.9, 130.1, 131.0, 133.9, 141.1, 151.5, 156.8, 165.5, 165.8, 171.8

22d) 2-(4-(2-(5-Chlorothiophen-2-yl)-7,8-dihydro-5H-thiopyrano[4,3-d]pyrimidin-4-yloxy)phenyl)acetic acid 1N sodium hydroxide solution (9.0 ml, 9.0 mmol) was added to the ester 22c) (259 mg, 0.598 mmol) in methanol (70 ml) and the mixture was stirred for 65 h at room temperature. The solution was concentrated and the residue was washed with dichloromethane (3×15 ml). Water (30 ml) and 1 N hydrochloric acid (9.0 ml) were added and the suspension was stirred for 17 h at room temperature.

Filtration and washing of the solid with water (2×5 ml) provided the target compound as colorless solid. Yield: 115 mg (46% of theory). Melting range: 193-195° C.
$^{13}$C-NMR (101 MHz, DMSO-d6, δ ppm): 22.4, 24.2, 33.0, 39.9, 113.3, 121.3, 128.0, 128.3, 130.3, 132.1, 140.7, 150.7, 155.5, 165.1, 166.0, 172.5

Synthesis Example 23: 2-[4-[[2-(5-Chloro-thiophen-2-yl)-6-oxo-7,8-dihydro-5H-thiopyrano[4,3-d]pyrimidin-4-yl]oxy]-phenyl]-acetic acid

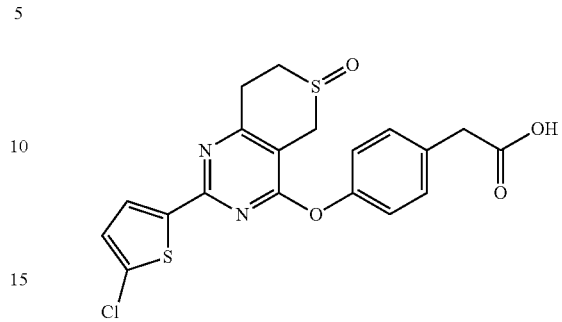

23a) Methyl 2-[4-[[2-(5-chloro-thiophen-2-yl)-6-oxo-7,8-dihydro-5H-thiopyrano[4,3-d]pyrimidin-4-yl]oxy]-phenyl]-acetate The thioether of 22c) (350 mg, 0.81 mmol) was oxidized with m-chloroperoxybenzoic acid (77%, 189 mg, 0.89 mmol) in an analogous manner as described under procedure 20a). Different from procedure 20a), the final product was submitted to the next step 23b) without purification by column chromatography. Beige solid. Yield: 362 mg (99% of theory). Melting range: 210° C.
$^{13}$C-NMR (101 MHz, CDCl3, δ ppm): 23.3, 40.5, 43.0, 43.9, 52.0, 105.2, 121.7, 127.3, 128.6, 130.2, 131.3, 134.6, 140.6, 151.1, 157.8, 163.6, 167.3, 171.7

23b) 2-[4-[[2-(5-Chloro-thiophen-2-yl)-6-oxo-7,8-dihydro-5H-thiopyrano[4,3-d]pyrimidin-4-yl]oxy]-phenyl]-acetic acid Prepared from ester of 23a) (255 mg, 0,568 mmol) in analogy to the procedure of 22d). Colorless solid. Yield: 108 mg (44% of theory). Melting range: 234-240° C.
$^{13}$C-NMR (101 MHz, DMSO-d6, δ ppm): 22.9, 39.9, 41.2, 42.6, 106.9, 121.2, 128.4, 130.9, 132.3, 132.4, 140.4, 150.5, 156.1, 164.5, 167.1, 172.5

Synthesis Example 24: 2-[4-[[2-(5-Chloro-thiophen-2-yl)-6,6-dioxo-7,8-dihydro-5H-thiopyrano[4,3-d]pyrimidin-4-yl]oxy]-phenyl]-acetic acid

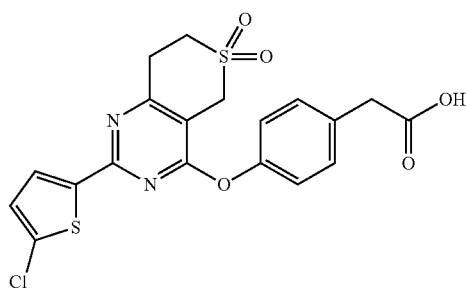 [SMILES: O=C(O)Cc1ccc(Oc2nc(-c3ccc(Cl)s3)nc3c2CS(=O)(=O)CC3)cc1]

24a) Methyl 2-[4-[[2-(5-chloro-thiophen-2-yl)-6,6-dioxo-7,8-dihydro-5H-thiopyrano[4,3-d]pyrimidin-4-yl]oxy]-phenyl]-acetate The thioether of 22c) (425 mg, 0.98 mmol) was oxidized with m-chloroperoxybenzoic acid (77%, 625 mg, 2.95 mmol) in analogy to the procedure of 20a). The final purification of the product was performed by column chromatography [silica gel 60; ethyl acetate/cyclohexane 1:2]. Beige solid. Yield: 345 mg (76% of theory). Melting range: 97-101° C.

$^{13}$C-NMR (101 MHz, CDCl3, δ ppm): 31.9, 39.3, 46.3, 46.7, 51.6, 108.6, 121.4, 128.5, 128.8, 130.4, 131.8, 132.9, 140.0, 150.5, 156.8, 162.5, 166.1, 171.5

24b) 2-[4-[[2-(5-Chloro-thiophen-2-yl)-6,6-dihydro-5H-thiopyrano[4,3-d]pyrimidin-4-yl]oxy]-phenyl]-acetic acid Prepared from ester of 24a) (369 mg, 0,794 mmol) in an analogous manner as described under the procedure of 15d). Colorless solid. Yield: 310 mg (87% of theory). Melting range: 225° C.

$^{13}$C-NMR (101 MHz, DMSO-d6, δ ppm): 32.0, 39.5, 46.3, 46.7, 108.6, 121.3, 128.5, 128.8, 130.3, 132.4, 132.9, 140.0, 150.3, 156.9, 162.5, 166.1, 172.5

Synthesis Example 25: 2-(4-(2-(Thiazol-5-yl)-6,7-dihydro-5H-cyclopenta[d]pyrimidin-4-yloxy)phenyl)acetic acid

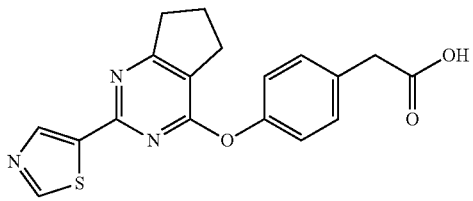 [SMILES: O=C(O)Cc1ccc(Oc2nc(-c3cncs3)nc3c2CCC3)cc1]

25a) 2-(4-(2-(Thiazol-5-yl)-6,7-dihydro-5H-cyclopenta[d]pyrimidin-4-yloxy)phenyl)acetic acid methylester 5-(Tributylstannyl)thiazole (430 mg, 1.15 mmol) and bis(triphenylphosphine)palladium(II) chloride (35 mg, 0.05 mmol) were added to the chloropyrimidine of 1c) (320 mg, 1.01 mmol) in DMF (1 ml) and the mixture was stirred for 2 h at 130° C. The reaction mixture was diluted with water (30 ml) and extracted with dichlormethane (3×15 ml). The combined organic layers were dried over sodium sulfate, the solvents were removed in vacuo and the residue was purified by chromatography [silica gel 60; cyclohexane/ethyl acetate 9:1]. Yellow oil. Yield: 80 mg (22% of theory)

13C-NMR (101 MHz, CDCl3, δ ppm): 22.0, 26.9, 34.3, 40.5, 119.1, 121.7, 130.3, 130.7, 143.9, 151.7, 155.6, 165.1, 175.5, 177.4

25b) 2-(4-(2-(Thiazol-5-yl)-6,7-dihydro-5H-cyclopenta[d]pyrimidin-4-yloxy)phenyl)acetic acid 2N sodium hydroxide solution (1 ml, 2 mmol) was added to the ester obtained from the previous reaction 25a) (80 mg, 0.22 mmol) in dioxane (3 ml) and stirred for 16 h at room temperature. The solvent was distilled off and the residue acidified with 2N hydrochloric acid (1.5 ml, 3 mmol). The precipitating solid was filtered off and washed with water (3×2 ml) and dried. White solid. Yield: 64 mg (82% of theory). Melting range: 191-193° C.

13C-NMR (101 MHz, DMSO-d6, δ ppm): 21.5, 26.5, 33.6, 119.2, 121.0, 123.1, 130.5, 131.9, 151.0, 153.7, 155.0, 158.3, 164.8, 172.6, 176.7

Synthesis Example 26: 2-(4-(2-(2-Chlorothiazol-5-yl)-6,7-dihydro-5H-cyclopenta[d]pyrimidin-4-yloxy)phenyl)acetic acid

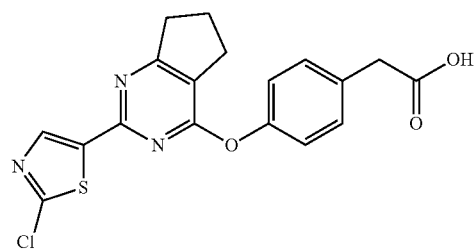 [SMILES: O=C(O)Cc1ccc(Oc2nc(-c3cnc(Cl)s3)nc3c2CCC3)cc1]

26a) 2-Chloro-5-tributylstannylthiazol

A solution of 2N lithium diisopropylamide (6.0 ml, 12.0 mmol, in THF/heptane/ethylbenzene) was added dropwise to a solution of 2-chlorothiazole (1.20 g, 10.04 mmol) in THF (25 ml) at −70° C. The reaction mixture was stirred for 30 minutes at a temperature of −50° C. and then cooled again to −70° C. and Tributylchlorostannane (3.30 ml, 12.12 mmol) was added at that temperature and mixture was slowly warmed up to room temperature (ca. 30 min). The reaction was quenched with ammonium chloride solution (40 ml) and extracted with cyclohexane (3×20 ml). The combined organic phases were washed with 1N hydrochloric acid (3×20 ml), dried over sodium sulfate and evaporated. The residue (yellow oil, 4.60 g) was purified by chromatography [silica gel 60, CH$_2$Cl$_2$/cyclohexane; 1:1]. Colorless oil. Yield: 3.11 g (76% of theory)

13C-NMR (101 MHz, CDCl3, δ ppm): 11.0, 13.6, 27.1, 28.8, 132.3, 147.8, 156.2

26b) 2-(4-(2-Bromo-6,7-dihydro-5H-cyclopenta[d]pyrimidin-4-yloxy)phenyl)acetic acid methyl ester The chloro compound obtained under procedure 1c) (5.62 g, 17.6 mmol) was stirred in HBr/glacial acetic acid (5.7M, 62 ml, 352.6 mmol) for 4 h at room temperature. After addition of water (150 ml), a precipitation occurred which was filtered off and dried in vacuum. Colorless solid. Yield: 4.25 g (66% of theory)

13C-NMR (101 MHz, DMSO-d6, δ ppm): 21.4, 25.9, 33.4, 39.9, 51.7, 120.1, 121.2, 130.7, 131.9, 148.1, 150.7, 165.0, 171.5, 179.6

26c) 2-(4-(2-(2-Chlorothiazol-5-yl)-6,7-dihydro-5H-cyclopenta[d]pyrimidin-4-yloxy)phenyl)acetic acid Bis(triphenylphosphine)palladium-(II)-chloride (59 mg, 0.08 mmol) was added to a solution of the ester obtained in the previous reaction 26b) (610 mg, 1.68 mmol) and the stannane obtained under 26a) (802.9 mg, 1.96 mmol) in DMF (3.6 ml) and the mixture was stirred under an argon atmosphere for 72 h at 130° C. Methanol (10 ml), dioxane (30 ml) and 1N sodium hydroxide solution (5 ml, 5 mmol) were added and stirring was continued for 1 h at 100° C. Upon the addition of 1N hydrochloric acid (7 ml, 7 mmol), a solid precipitated which was filtered off and purified by chromatography [silica gel 60, chloroform/methanol/acetic acid 98:2:1]. Yellow solid. Yield: 78.5 mg (12% of theory). Melting range: 175-180° C.

13C-NMR (101 MHz, CDCl3, δ ppm): 22.0, 26.9, 34.2, 40.3, 119.4, 121.7, 130.3, 130.6, 140.4, 141.8, 151.6, 154.1, 157.2, 165.0, 176.0, 177.3

Synthesis Example 27: 2-(4-(2-(5-Carbamoylthiophen-2-yl)-6,7-dihydro-5H-cyclopenta[d]pyrimidin-4-yloxy)phenyl)acetic acid

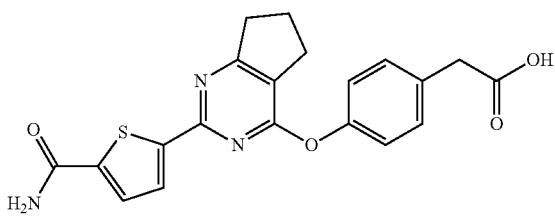 [SMILES: NC(=O)c1ccc(-c2nc3c(c(Oc4ccc(CC(=O)O)cc4)n2)CCC3)s1]

27a) 2-(4-(2-(5-Cyanothiophen-2-yl)-6,7-dihydro-5H-cyclopenta[d]pyrimidin-4-yloxy)phenyl)acetic acid methyl ester A solution of 5-cyanothiophen-2-ylboronic acid (153 mg, 1 mmol) and the pyrimidine bromide from 26b) (363 mg, 1 mmol) in THF (8 ml) was transferred into a pressure reactor with a teflon surface, to which potassium fluoride (116 mg, 2 mmol) and bis(tri-tert-butylphosphine)palladium(0) (26 mg, 0.050 mmol) were added. The reaction mixture was then stirred overnight at 90° C. (oil bath). For the workup, brine (50 ml) was added and the mixture was extracted with ethyl acetate (3×20 ml). The combined organic phases were dried over magnesium sulfate and concentrated to small volume. The residue was purified by chromatography [silica gel 60, cyclohexane/ethyl acetate 4:1]. Colorless Solid. Yield: 271 mg (69% of theory)

1H-NMR (400 MHz, CDCl3, δ ppm): 2.21 (m, 2H), 2.99 (m, 2H), 3.05 (m, 2H), 3.69 (s, 2H), 3.73 (s, 3H), 7.16 (d, J=8.4, 2H), 7.35 (d, J=8.4, 2H), 7.50 (d, J=4.0, 1H), 7.67 (d, J=4.0, 1H)

13C-NMR (101 MHz, CDCl3, δ ppm): 21.9, 26.9, 34.2, 40.5, 52.1, 111.6, 114.3, 119.8, 121.6, 127.6, 130.2, 131.1, 137.9, 150.1, 151.4, 158.0, 165.0, 171.8, 177.4

LC-MS (method 2): $R_t$=4.08 min, m/z: [M+H]$^+$=392.2

27b) 2-(4-(2-(5-Carbamoylthiophen-2-yl)-6,7-dihydro-5H-cyclopenta[d]pyrimidin-4-yloxy)phenyl)acetic acid The ester obtained under 26b) (264 mg, 0.67 mmol) in THF (9 ml) was mixed with a solution of 1N sodium hydroxide (3.2 ml) and stirred for 64 h at room temperature. After the addition of 2N hydrochloric acid (1.6 ml) and the removal of THF, a solid precipitated which was filtered off, washed with water and dried. White solid. Yield: 255 mg (96% of theory). Melting range: 250-253° C.

1H-NMR (400 MHz, DMSO-d6, δ ppm): 2.11 (m, 2H), 2.88 (m, 2H), 2.97 (m, 2H), 3.62 (s, 2H), 7.20 (d, J=8.4, 2H), 7.33 (d, J=8.4, 2H), 7.45 (s, 1H), 7.58 (d, J=4.0, 1H), 7.65 (d, J=4.0, 1H), 8.00 (s, 1H), 12.3 (s, 1H)

13C-NMR (101 MHz, DMSO-d6, δ ppm): 21.4, 26.4, 33.6, 39.9, 118.7, 121.0, 128.3, 129.2, 130.3, 131.9, 142.7, 146.0, 150.8, 158.3, 162.5, 164.4, 172.5, 177.3

LC-MS (method 2): $R_t$=3.66 min, m/z: [M+H]$^+$=396.2

Synthesis Example 28: 2-(4-(2-(5-Cyanothiophen-2-yl)-6,7-dihydro-5H-cyclopenta[d]pyrimidin-4-yloxy)phenyl)acetic acid

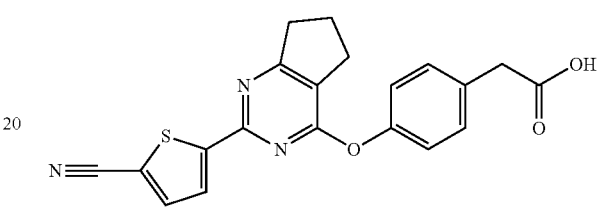

The amide of 27b) (137 mg, 346 µmol) in DMF (1 ml) and thionyl chloride (75 µl, 1.04 mmol) were stirred for 10 min at room temperature. The reaction mixture was then poured on a water/ice mixture (20 ml) and stirred for another 10 min. After addition of solid sodium chloride and extraction with THF (3×20 ml), the combined organic phases were dried over magnesium sulfate and evaporated. The residue was purified by chromatography [silica gel 60, dichloromethane/methanol; 10:1]. White solid. Yield: 73 mg (56% of theory). Melting range: 185-189° C.

1H-NMR (400 MHz, DMSO-d6, δ ppm): 2.14 (m, 2H), 2.89 (m, 2H), 3.00 (s, 2H), 3.62 (s, 2H), 7.21 (d, J=8.4, 2H), 7.36 (d, J=8.4, 2H), 7.63 (d, J=4.0, 1H), 7.91 (d, J=4.0, 1H)

13C-NMR (101 MHz, DMSO-d6, δ ppm): 21.4, 26.4, 33.5, 40.1, 110.3, 114.1, 119.9, 121.0, 128.0, 130.4, 132.3, 139.8, 149.4, 150.6, 157.0, 164.5, 172.7, 177.6

LC-MS (method 2): $R_t$=3.91 min, m/z: [M+H]$^+$=378.2

Synthesis Example 29: 2-(4-(2-(5-Bromothiophen-2-yl)-6,7-dihydro-5H-cyclopenta[d]pyrimidin-4-yloxy)phenyl)acetic acid

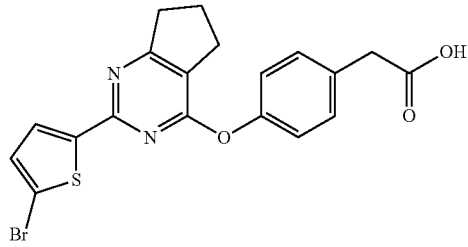 [SMILES: O=C(O)Cc1ccc(Oc2nc(-c3ccc(Br)s3)nc3c2CCC3)cc1]

29a) Methyl 2-aminocyclopent-1-enecarboxylate

Methyl 2-oxocyclopentanecarboxylate (19.84 ml, 160 mmol) in methanol (500 ml) and anhydrous ammonium acetate (72.8 g, 945 mmol) were mixed and stirred for 16 h at room temperature. The solvent was distilled off, water was added (200 ml) and the mixture was extracted with ethyl acetate (3×100 ml). The organic layers were combined, dried over sodium sulfate, and evaporated. The solid residue was recrystallized in hexane (100 ml). White solid. Yield: 19.8 g (80% of theory). Melting range: 52-53° C.

13C-NMR (101 MHz, DMSO-d6, □ ppm): 14.7, 20.5, 29.1, 34.2, 57.5, 91.5, 163.2, 166.8

29b) Potassium 2-(5-bromothiophen-2-yl)-6,7-dihydro-5H-cyclopenta[d]pyrimidin-4-olate 5-Bromothiophen-2-carbonitrile (752 mg, 4 mmol) and methyl 2-aminocyclopent-1-enecarboxylate (480 mg, 3.08 mmol) were dissolved in mesitylene (8 ml), potassium tert-butylate (448 mg, 4 mmol) was added and the suspension was stirred for 4 h at 150° C. The reaction mixture was filtered and the filtrate washed with water and ethyl acetate. Beige solid. Yield: 476 mg (52% of theory)

13C-NMR (101 MHz, DMSO-d6, □ ppm): 20.6, 27.1, 34.0, 117.2, 122.0, 129.3, 131.9, 139.7, 151.8, 161.3, 169.0

29c) Methyl 2-(4-((2-(5-bromothiophen-2-yl)-6,7-dihydro-5H-cyclopenta[d]pyrimidin-4-yl)oxy)phenyl)acetate The product of 29b) (149 mg, 05 mmol) in THF (10 ml), PyBOP (520 mg, 1 mmol) and cesium carbonate (641 mg, 2 mmol) were mixed and stirred for 1 h at room temperature. Thereafter, cesium carbonate (641 mg, 2 mmol) and methyl 2-(4-hydroxyphenyl)acetate (83 mg, 0.5 mmol) were added and the suspension was stirred for another 16 h at room temperature. The reaction mixture was diluted with water (20 ml) and ethyl acetate (20 ml) and the aqueous phase was separated and extracted with ethyl acetate (4×15 ml). The organic layers were combined, dried over magnesium sulfate and evaporated. The residue was purified by chromatography [Silica gel 60; cyclohexan/ethyl acetate 4:1]. Colorless solid. Yield: 170 mg (76% of theory).

1H-NMR (400 MHz, DMSO-d6, δ ppm): 2.15-2.22 (2H), 2.93-3.05 (4H), 3.68 (s, 2H), 3.73 (s, 3H), 6.98-6.99 (1H), 7.16-7.19 (2H), 7.33-7.35 (2H), 7.49-7.50 (1H)

29d) 2-(4-(2-(5-Bromothiophen-2-yl)-6,7-dihydro-5H-cyclopenta[d]pyrimidin-4-yloxy)phenyl)acetic acid Synthesis in an analogous manner to procedure 25b) from the ester of 29c) (160 mg, 0.36 mmol). White solid. Yield: 130 mg (84% of theory). Melting range: 197-199° C.

13C-NMR (101 MHz, DMSO-d6, δ ppm): 21.5, 26.4, 33.6, 115.6, 118.4, 121.1, 128.6, 130.4, 131.7, 132.0, 143.9, 150.8, 157.8, 164.5, 172.6, 177.3

Synthesis Example 30: 2-(4-(2-(4-Bromo-5-methylthiophen-2-yl)-6,7-dihydro-5H-cyclopenta[d]pyrimidin-4-yloxy)phenyl)acetic acid

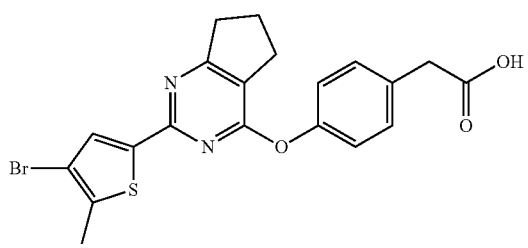 [SMILES: Cc1sc(-c2nc3c(c(Oc4ccc(CC(=O)O)cc4)n2)CCC3)cc1Br]

30a) Potassium 2-(4-bromo-5-methylthiophen-2-yl)-6,7-dihydro-5H-cyclopenta[d]pyrimidin-4-olate Preparation of the target compound in an analogous manner to procedure 29b) using 4-bromo-5-methylthiophene-2-carbonitrile (808 mg, 4 mmol) and methyl 2-aminocyclopent-1-enecarboxylate (480 mg, 3.08 mmol). Beige solid. Yield: 909 mg (84% of theory).

13C-NMR (101 MHz, DMSO-d6, δ ppm): 14.1, 20.8, 26.3, 27.8, 33.8, 108.1, 118.6, 126.9, 134.5, 144.4, 158.3, 166.9, 171.5

30b) Methyl 2-(4-((2-(4-bromo-5-methylthiophen-2-yl)-6,7-dihydro-5H-cyclopenta[d]pyrimidin-4-yl)oxy)phenyl)acetate Prepared in analogy to the procedure 29c) from the pyrimidine salt 30a) (156 mg, 0.45 mmol) and methyl 2-(4-hydroxyphenyl)acetate (83 mg, 0.5 mmol). Purification of the raw product by recrystallization with ethyl acetate Yield: 130 mg (63% of theory)

1H-NMR (400 MHz, DMSO-d6, δ ppm): 2.10-2.16 (2H), 2.36 (s, 3H), 2.87-2.98 (4H), 3.65 (s, 3H), 3.75 (s, 2H), 7.20-7.23 (2H), 7.34-7.39 (3H)

30c) 2-(4-(2-(4-Bromo-5-methylthiophen-2-yl)-6,7-dihydro-5H-cyclopenta[d]pyrimidin-4-yloxy)phenyl) acetic acid 1N sodium hydroxide solution (1.0 ml, 1.0 mmol) was added to the ester of 30b) (130 mg, 0.5 mmol) in dioxane (5 ml) and the mixture was stirred for 48 h at 23° C. The solvent was removed by destillation and the remnant acidified with 2N hydrochloric acid (1.5 ml, 3 mmol). The precipitating solid was filtered off, washed with water (3×2 ml) and dried. White solid. Yield: 115 mg (91% of theory). Melting range: 227-229° C.

13C-NMR (101 MHz, DMSO-d6, δ ppm): 14.8, 21.5, 26.4, 33.6, 109.4, 118.4, 121.1, 129.7, 130.4, 132.0, 138.5, 139.6, 150.8, 157.7, 164.5, 172.6, 177.3

Synthesis Example 31: 2-(4-(2-(5-(Methylthio)thiophen-2-yl)-6,7-dihydro-5H-cyclopenta[d]pyrimidin-4-yloxy)phenyl)acetic acid

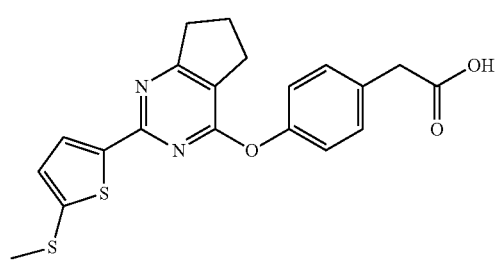 [SMILES: CSc1ccc(-c2nc3c(c(Oc4ccc(CC(=O)O)cc4)n2)CCC3)s1]

31a) 2-(5-(Methylthio)thiophen-2-yl)-6,7-dihydro-5H-cyclopenta[d]pyrimidin-4-ol Methyl 2-oxocyclopentanecarboxylate (1.34 g, 9.43 mmol), 5-(methylthio)thiophene-2-carboximidamide hydrochloride (984 mg, 4.71 mmol) and cesium carbonate (1.84 g, 5.65 mmol) in DMF (15 ml) were stirred for 2 h at 150° C. Addition of water (30 ml) resulted in the formation of a precipitate which was removed by centrifugation (10 min at 5000 rpm). The pellet was rinsed with water (2×30 ml), centrifuged, rinsed with ethanol (2×30 ml) and centrifuged again. From the supernatants of the centrifugation steps, additional target compound precipitated overnight which was separated via centrifugation yielding additional 446 mg of the product. Light brown solid. Yield: 896 mg (72% of theory). Melting range: 265-270° C.

31b) 4-Chloro-2-(5-(methylthio)thiophen-2-yl)-6,7-dihydro-5H-cyclopenta[d]pyrimidine A mixture of the product of 31a) (450 mg, 1.7 mmol) and phosphoroxychloride (3.17 ml, 5.22 g, 34 mmol) was heated for 2 h at 95° C. Water (25 ml) was then added under ice cooling. The mixture was diluted with dichloromethane (30 ml) and stirred for 10 min. The aqueous phase was separated and extracted with dichloromethane (2×30 ml). The organic layers were combined, dried over sodium sulfate and evaporated. Brown solid. Yield: 454 mg (95% of theory). Melting range: 97-99° C.

13C-NMR (101 MHz, CDCl3, δ ppm): 20.5, 21.3, 28.9, 34.6, 129.2, 129.7, 130.6, 141.8, 143.9, 156.8, 159.8, 176.3

31c) Methyl 2-(4-((2-(5-(methylthio)thiophen-2-yl)-6,7-dihydro-5H-cyclopenta[d]pyrimidin-4-yl)oxy)phenyl)acetate Potassium carbonate (332 mg, 2.4 mmol) was added to a solution of the product of 31b) (454 mg, 1.6 mmol) and methyl 2-(4-hydroxyphenyl)acetate (480 mg, 2.88 mmol) in acetonitril (50 ml). The mixture was stirred for 72 h at 80° C. and then filtered. The remnant was washed with acetonitril (10 ml) and dichloromethane (10 ml) and the volume of the combined filtrates was reduced. The residue was purified by chromatography [silica gel 60; ethyl acetate/cyclohexane 1:6]. Colorless solid. Yield: 353 mg (54% of theory). Melting range: 105-106° C.

13C-NMR (101 MHz, CDCl3, δ ppm): 20.9, 21.9, 26.8, 34.3, 40.5, 52.0, 117.8, 121.5, 128.7, 129.7, 130.0, 130.6, 142.1, 143.7, 151.7, 159.3, 164.8, 171.9, 177.1

31d) 2-(4-(2-(5-(Methylthio)thiophen-2-yl)-6,7-dihydro-5H-cyclopenta[d]pyrimidin-4-yloxy)phenyl)acetic acid 1N sodium hydroxide solution (2.46 ml, 2.3 mmol) was added to the ester of 31c) (190 mg, 0.46 mmol) in THF (15 ml) and the mixture was stirred for 16 h at room temperature. 1N hydrochloric acid (2.3 ml) was added and stirring was continued for another 1.5 h at room temperature. The THF was removed under vacuum and the precipitating solid was separated by filtration and washed with water (2×5 ml) and dichloromethane (2×5 ml). Colorless solid. Yield: 150 mg (82% of theory). Melting range: 195-197° C.

13C-NMR (101 MHz, DMSO-d6, δ ppm): 19.5, 21.4, 26.3, 33.5, 39.9, 117.7, 121.0, 128.6, 128.8, 130.3, 131.8, 142.0, 142.2, 150.8, 158.2, 164.3, 172.5, 177.2

Synthesis Example 32: 2-(4-(2-(5-(Methylsulfonyl)thiophen-2-yl)-6,7-dihydro-5H-cyclopenta[d]pyrimidin-4-yloxy)phenyl)acetic acid

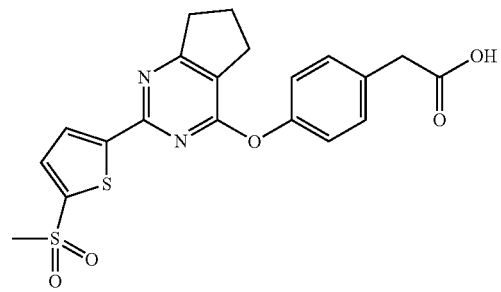 [SMILES: CS(=O)(=O)c1ccc(-c2nc3c(c(Oc4ccc(CC(=O)O)cc4)n2)CCC3)s1]

32a) 2-(4-((2-(5-(Methylsulfonyl)thiophen-2-yl)-6,7-dihydro-5H-cyclopenta[d]pyrimidin-4-yl)oxy)phenyl)acetic acid A solution of m-chloroperbenzoic acid (77%, 505 mg, 2.26 mmol) in dichloromethane (25 ml) was added to the ester of 31c) (358 mg, 0.868 mmol) in dichloromethane (30 ml) and the mixture was stirred for 4 h at room temperature. The reaction mixture was quenched with saturated sodium hydrogencarbonate solution (30 ml) and stirred for 30 min at room temperature. The organic phase was separated, washed with saturated sodium hydrogencarbonate solution (30 ml), dried over sodium sulfate and evaporated. The residue was purified by chromatography [silica gel 60; ethyl acetate/cyclohexane 1:2→1:1, followed by ethyl acetate]. Colorless solid. Yield: 247 mg (64% of theoryl). Melting range: 165-166° C.

13C-NMR (101 MHz, CDCl3, δ ppm): 21.9, 26.9, 34.2, 40.5, 45.9, 52.0, 119.8, 121.5, 127.6, 130.2, 131.0, 133.7, 143.1, 151.2, 151.4, 158.2, 165.0, 171.8, 177.4

32b) 2-(4-(2-(5-(Methylsulfonyl)thiophen-2-yl)-6,7-dihydro-5H-cyclopenta[d]pyrimidin-4-yloxy)phenyl)acetic acid Preparation of the target compound in an analogous manner to procedure 31d) from the sulfone 31a) (227 mg, 0.51 mmol). Colorless solid. Yield: 188 mg (86% of theory). Melting range: 213-220° C.

13C-NMR (101 MHz, DMSO-d6, δ ppm): 21.4, 26.4, 33.6, 40.1, 45.0, 119.7, 121.0, 128.0, 130.4, 132.0, 133.9, 143.7, 149.1, 150.7, 157.4, 164.5, 172.5, 177.5

Synthesis Example 33: 2-(4-((2-(4-Bromophenyl)-6,7-dihydro-5H-cyclopenta[d]pyrimidin-4-yl)oxy)phenyl)acetic acid

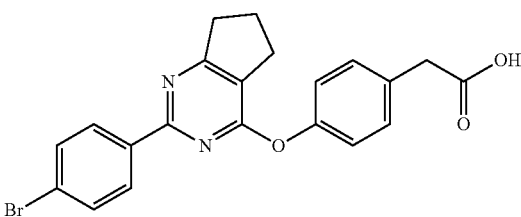 [SMILES: O=C(O)Cc1ccc(Oc2nc(-c3ccc(Br)cc3)nc3c2CCC3)cc1]

33a) 2-(4-Bromophenyl)-6,7-dihydro-5H-cyclopenta[d]pyrimidin-4-ol

Methyl 2-oxocyclopentanecarboxylate (3.12 ml, 25.1 mmol) was added dropwise to a solution of 4-bromobenzimidamide (5.00 g, 25.1 mmol) in dioxane (170 ml). The reaction mixture was stirred overnight at 90° C. and then allowed to cool down to room temperature. The precipitate was separated, washed with diethyl ether and dried. Beige Solid. Yield: 2.20 g (30% of theory).

LC-MS (method 3): $R_t$=0.60 min, m/z: [M+H]$^+$=291.0/293.0

33b) 2-(4-Bromophenyl)-4-chloro-6,7-dihydro-5H-cyclopenta[d]pyrimidine 2-(4-Bromophenyl)-6,7-dihydro-5H-cyclopenta[d]pyrimidin-4-ol (3.00 g, 11.9 mmol) and phosphoroxychloride (44 ml) were stirred under an inert atmosphere for 3 h at 90° C. The mixture was cooled to ambient temperature, then poured into iced water, neutralized with sodium carbonate and sodium hydrogen carbonate and extracted with dichloromethane. The combined organic layers were dried over magnesium sulfate and evaporated. The remnant was titurated in 20 ml diethyl ether, filtered, and washed with 10 ml diethyl ether and then purified by chromatography [silica gel, hexane/ethyl acetate=9:1]. Light grey solid. Yield: 2.20 g (60% of theory).

LC-MS (method 3): $R_t$=1.00 min, m/z: [M+H]$^+$ 309.0/311.0

33c) Methyl 2-(4-((2-(4-bromophenyl)-6,7-dihydro-5H-cyclopenta[d]pyrimidin-4-yl)oxy)phenyl)acetate 2-(4-Bromophenyl)-4-chloro-6,7-dihydro-5H-cyclopenta[d]pyrimidine (200 mg, 0.65 mmol), methyl(4-aminophenyl)acetate (107 mg, 0.65 mmol) and potassium carbonate (267 mg, 1.94 mmol) in anhydrous DMF (4 ml) were stirred overnight at room temperature, followed by 3 h at 70° C. The reaction mixture was diluted with water and extracted with ethyl acetate (3×25 ml). The combined organic layers were washed with brine, dried over magnesium sulfate and concentrated. The raw product was purified by chromatography [silica gel, hexane/ethyl acetate=9:1]. White solid. Yield: 180 mg (63% of theory).

LC-MS (method 3): $R_t$=1.01 min, m/z: [M+H]$^+$=439.1/441.1

33d) 2-(4-((2-(4-Bromophenyl)-6,7-dihydro-5H-cyclopenta[d]pyrimidin-4-yl)oxy)phenyl)acetic acid The product of 33c) (180 mg, 0.41 mmol) and lithium hydroxide (19 mg, 0.82 mmol) were stirred in a THF/water blend (5:1, 3 ml) for 24 h at room temperature. The mixture was diluted with water (15 ml), adjusted to pH 1-2 with 1 N hydrochloric acid and extracted with dichloromethane/THF (4:1). The combined organic layers were dried over magnesium sulfate and evaporated. For the final purification, the product was triturated in diethyl ether. White solid. Yield: 150 mg (86% of theory).

LC-MS (method 3): $R_t$=0.88 min, m/z: [M+H]$^+$=425.0/427.0

Synthesis Example 34: 2-(4-((2-(3-Bromophenyl)-6,7-dihydro-5H-cyclopenta[d]pyrimidin-4-yl)oxy)phenyl)acetic acid

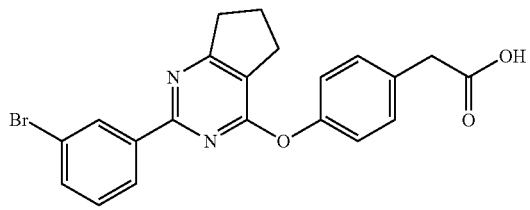 [SMILES: O=C(O)Cc1ccc(Oc2nc(-c3cccc(Br)c3)nc3c2CCC3)cc1]

Preparation of the target compound in an analogous manner to procedures for example 33. White solid.

LC-MS (method 3): $R_t$=0.88 min, m/z: [M+H]$^+$=425.0/427.0

Synthesis Example 35: 2-(4-((2-(Thiazol-4-yl)-6,7-dihydro-5H-cyclopenta[d]pyrimidin-4-yl)oxy)phenyl)acetic acid

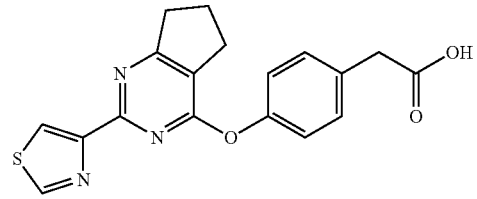 [SMILES: O=C(O)Cc1ccc(Oc2nc(-c3cscn3)nc3c2CCC3)cc1]

35a) Methyl 2-(4-((2-(thiazol-4-yl)-6,7-dihydro-5H-cyclopenta[d]pyrimidin-4-yl)oxy)phenyl)acetate Preparation of the target compound in an analogous manner to procedure 25a) from 4-(tributylstannyl)thiazole (320 mg, 1.01 mmol) and methyl 2-(4-((2-chloro-6,7-dihydro-5H-cyclopenta[d]pyrimidin-4-yl)oxy)phenyl)acetate (430 mg, 1.15 mmol). Yellow solid. Yield: 130 mg (35% of theory)

13C-NMR (101 MHz, DMSO-d6, δ ppm): 21.5, 26.4, 33.7, 51.7, 118.8, 121.1, 122.6, 130.4, 131.0, 151.3, 154.4, 154.7, 158.8, 164.6, 171.5, 177.4

35b) 2-(4-((2-(Thiazol-4-yl)-6,7-dihydro-5H-cyclopenta[d]pyrimidin-4-yl)oxy)phenyl)acetic acid The target compound was prepared in analogy to the procedure 25b) from the ester of 35a) (130 mg, 0.35 mmol). White solid. Yield: 106 mg (85% of theory). Melting range: 127-129° C.

13C-NMR (101 MHz, DMSO-d6, δ ppm): 21.5, 26.5, 33.6, 119.2, 121.0, 123.1, 130.5, 131.9, 151.0, 153.7, 155.0, 158.3, 164.8, 172.6, 176.7

Synthesis Example 36: 2-(4-((2-(2-Chlorothiazol-4-yl)-6,7-dihydro-5H-cyclopenta[d]pyrimidin-4-yl)oxy)phenyl)acetic acid

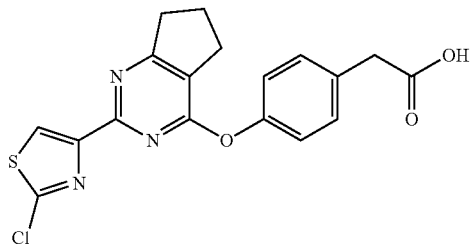 [SMILES: O=C(O)Cc1ccc(Oc2nc(-c3csc(Cl)n3)nc3c2CCC3)cc1]

36a) Methyl 2-(4-((2-(1-ethoxyvinyl)-6,7-dihydro-5H-cyclopenta[d]pyrimidin-4-yl)oxy)phenyl)acetate Methyl 2-(4-((2-chloro-6,7-dihydro-5H-cyclopenta[d]pyrimidin-4-yl)oxy)phenyl)acetate (699 mg, 2.19 mmol), tributyl(1-ethoxyvinyl)stannane (950 mg, 2.63 mmol), caesium fluoride (732 mg, 4.82 mmol) and bis(tri-tert-butylphosphine)palladium(0) in anhydrous dioxane (10 ml) were stirred for 2 h at 120° C. The reaction mixture was diluted with dichloromethane (20 ml) and filtered over silica gel. The solvents were removed and the residue was purified by chromatography [silica gel 60; cyclohexane/ethyl acetate 3:1]. Colorless solid. Yield: 636 mg (82% of theory)

1H-NMR (400 MHz, CDCl3, δ ppm): 1.42 (t, J=7.0, 3H), 2.15 (m, 2H), 2.92 (m, 2H), 3.06 (m, 2H), 3.64 (s, 2H), 3.70 (s, 3H), 3.96 (q, J=7.0, 2H), 4.42 (d, J=1.8, 1H), 5.32 (d, J=1.8, 1H), 7.17 (d, J=8.5, 2H), 7.29 (d, J=8.5, 2H)

13C-NMR (101 MHz, CDCl3, δ ppm): 14.2, 22.1, 26.8, 34.5, 40.5, 52.0, 63.9, 89.5, 119.4, 121.5, 130.0, 130.5, 151.7, 157.1, 160.4, 164.6, 171.8, 177.1

LC-MS (method 2): m/z: [M+H]$^+$=355.20, R$_t$=3.80 min

36b) Methyl 2-(4-((2-(2-bromoacetyl)-6,7-dihydro-5H-cyclopenta[d]pyrimidin-4-yl)oxy)phenyl)acetate N-Bromosuccinimide (314 mg, 1.76 mmol) was added at 0° C. to a solution of the vinyl ether obtained under 36a) (625 mg, 1.76 mmol) in THF (6 ml) and water (2 ml) and the mixture was stirred for 1 h at room temperature. Dichloromethane (30 ml) and brine (30 ml) were added and the aqueous phase was separated and extracted with dichloromethane (3×20 ml). The organic layers were combined, dried over magnesium sulfate and evaporated. The residue was purified by chromatography [silica gel 60; cyclohexane/ethyl acetate 2:1]. Colorless solid. Yield: 580 mg (81% of theory)

1H-NMR (400 MHz, CDCl3, δ ppm): 2.25 (m, 2H), 3.06 (m, 2H), 3.14 (m, 2H), 3.67 (s, 2H), 3.72 (s, 3H), 4.42 (s, 2H), 7.17 (d, J=8.4, 2H), 7.34 (d, J=8.4, 2H)

LC-MS (Method 2): m/z: [M]$^+$=405.10, R$_t$=3.67 min

36c) Methyl 2-(4-((2-(2-aminothiazol-4-yl)-6,7-dihydro-5H-cyclopenta[d]pyrimidin-4-yl)oxy)phenyl)acetate The ester of 36b) (600 mg, 1.48 mmol) and thiourea (113 mg, 1.48 mmol) in methanol (5 ml) were stirred for 1 h at 65° C. The methanol was then distilled off and the remnant dissolved in dichloromethane (20 ml) and saturated sodium carbonate solution (20 ml). The aqueous phase was separated and extracted with dichloromethane (3×20 ml). The combined organic layers were dried over magnesium sulfate and evaporated. The residue was purified by chromatography [silica gel 60; cyclohexane/ethyl acetate 1:1]. Colorless solid. Yield: 369 mg (65% of theory)

1H-NMR (400 MHz, CDCl3, δ ppm): 2.16 (m, 2H), 2.94 (m, 2H), 3.08 (m, 2H), 3.66 (s, 2H), 3.71 (s, 3H), 5.32 (s (breit), 2H), 7.17 (d, J=8.5, 2H), 7.19 (s, 1H), 7.32 (d, J=8.5, 2H)

13C-NMR (101 MHz, CDCl3, δ ppm): 21.9, 26.9, 34.5, 40.5, 52.0, 122.2, 118.7, 121.6, 130.1, 130.6, 149.7, 151.9, 159.9, 164.9, 167.5, 171.8, 177.4

LC-MS (method 2): m/z: [M+H]$^+$=383.20, R$_t$=3.36 min

36d) 2-(4-((2-(2-Chlorothiazol-4-yl)-6,7-dihydro-5H-cyclopenta[d]pyrimidin-4-yl)oxy)phenyl)acetic acid Copper(I) chloride (127 mg, 1.28 mmol) was added to the product of 35c) (350 mg, 0.91 mmol) in concentrated hydrochloric acid (3 ml) at 0° C. Sodium nitrite (88 mg, 1.28 mmol) in water (1 ml) was added dropwise and the reaction mixture was stirred for 16 h at room temperature. The mixture was diluted with water (20 ml), extracted with ethyl acetate (3×20 ml) and the combined organic layers were dried over magnesium sulfate and evaporated. The residue was dissolved in DMSO (3 ml) and water (1 ml), sodium sulfide (600 mg, 7.7 mmol) was added and the mixture was stirred for 1 h at room temperature. A black precipitate occurred which was filtered off, and washed with water and ethyl acetate. The aqueous phase was extrated with ethyl acetate (3×20 ml), and the combined organic phases were dried over Magnesium sulfate and concentrated. The residue was purified by chromatography [silica gel 60; dichloromethane/methanol 95:5]. Colorless solid. Yield: 110 mg (31% of theory). Melting range: 218-220° C.

1H-NMR (400 MHz, DMSO-d6, δ ppm): 2.14 (m, 2H), 2.90 (m, 2H), 3.00 (m, 2H), 3.60 (s, 2H), 7.20 (d, J=8.5, 2H), 7.33 (d, J=8.5, 2H), 8.08 (s, 1H)

13C-NMR (101 MHz, DMSO-d6, δ ppm): 21.4, 26.4, 33.6, 40.1, 119.3, 120.9, 125.4, 130.4, 131.9, 150.7, 150.9, 151.5, 157.5, 164.6, 172.6, 177.4

LC-MS (method 2): m/z: [M+H]$^+$=388.20, R$_t$=3.72 min

Synthesis Example 37: 2-(4-((2-(3,5-Difluoro-4-methoxyphenyl)-6,7-dihydro-5H-cyclopenta[d]pyrimidin-4-yl)oxy)phenyl)acetic acid

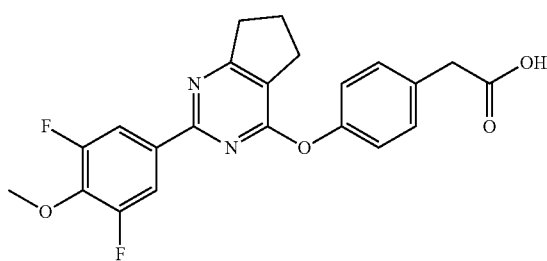 [SMILES: COc1c(F)cc(-c2nc3c(c(Oc4ccc(CC(=O)O)cc4)n2)CCC3)cc1F]

The target compound was prepared in an analogous manner to procedure 1d) from methyl 2-(4-((2-chloro-6,7-dihydro-5H-cyclopenta[d]pyrimidin-4-yl)oxy)phenyl)acetate (319 mg, 1 mmol) and (3,5-difluoro-4-methoxyphenyl) boronic acid (188 mg, 1 mmol). Colorless solid. Yield: 68 mg (17% of theory)

1H NMR (400 MHz, DMSO-d6, δ ppm): 2.14 (2H), 2.95 (t, J=7.5, 2H), 3.00 (t, J=7.8, 2H), 3.64 (s, 2H), 3.96 (s, 3H), 7.22 (d, J=8.5, 1H), 7.36 (d, J=8.5, 2H), 7.67 (m, 2H), 12.35 (s, 1H)

13C NMR (100 MHz, DMSO-d6, δ ppm): 21.5, 26.3, 33.7, 39.9, 61.6, 111.2 (dd, 4JC,F=7.2, 2JC,F=17.5), 118.9, 121.2, 130.4, 132.0 (t, 3JC,F=8.9), 132.1, 137.5 (t, 2JC,F=14.4), 150.7, 134.5 (dd, 3JC,F=6.3, 1JC,F=246.0), 159.5 (t, 4JC,F=3.5), 164.7, 172.5, 177.4

LC/MS (method 2): m/z: [M+H]$^+$=413.20, R$_t$=4.13 min

Synthesis Example 38: 2-(4-((2-(5-Methylthiophen-2-yl)-6,7-dihydro-5H-cyclopenta[d]pyrimidin-4-yl)oxy)phenyl)acetic acid

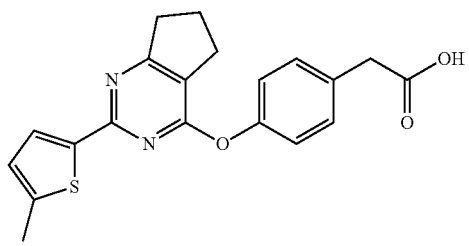 [SMILES: Cc1ccc(-c2nc3c(c(Oc4ccc(CC(=O)O)cc4)n2)CCC3)s1]

38a) Methyl 2-(4-((2-(5-methylthiophen-2-yl)-6,7-dihydro-5H-cyclopenta[d]pyrimidin-4-yl)oxy)phenyl)acetate Potassium phosphate (745 mg, 6.51 mmol), 2-dicyclohexylphosphino-2',6'-dimethoxybiphenyl (SPhos, 80 mg, 0.19 mmol) and palladium(II)-acetate (25 mg, 0.11 mmol) were added under an argon atmosphere to methyl 2-(4-((2-bromo-6,7-dihydro-5H-cyclopenta[d]pyrimidin-4-yl)oxy) phenyl)acetate (365 mg, 1.00 mmol) and (5-methylthiophen-2-yl)boronic acid (200 mg, 1.23 mmol) in n-butanol (0.5 ml) and the reaction mixture was stirred for 90 min at 110° C. (oil bath). The mixture was diluted with chloroform (30 ml) and filtered over kieselgur. The filtrate was concentrated and the residue purified by chromatography [silica gel 60; cyclohexane/ethyl acetate 9:1]. Colorless solid. Yield: 141 mg (37% of theory)

13C-NMR (101 MHz, DMSO-d6, δ ppm): 14.2, 21.5, 26.3, 33.6, 39.4, 51.7, 117.3, 121.2, 126.7, 128.4, 130.3, 131.1, 140.0, 143.9, 151.1, 158.9, 164.3, 171.6, 177.1

38b) 2-(4-((2-(5-Methylthiophen-2-yl)-6,7-dihydro-5H-cyclopenta[d]pyrimidin-4-yl)oxy)phenyl)acetic acid The target compound was prepared from the ester 38a) (125 mg, 0.33 mmol) in an analogous manner to procedure 4c). White solid. Yield: 93 mg (79% of theory). Melting range: 197-199° C.

13C-NMR (101 MHz, DMSO-d6, δ ppm): 15.2, 21.5, 26.3, 33.6, 39.94, 117.3, 121.02, 126.7, 128.4, 130.3, 131.8, 140.0, 143.9, 150.9, 158.9, 164.3, 172.6, 177.1

Synthesis Example 39: 2-(4-((2-(5-Chlorothiophen-2-yl)-6-methyl-6,7-dihydro-5H-cyclopenta[d]pyrimidin-4-yl)oxy)phenyl)acetic acid

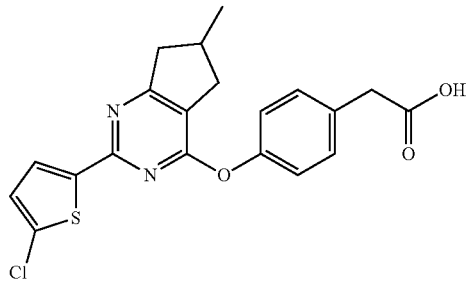 [SMILES: CC1Cc2nc(-c3ccc(Cl)s3)nc(Oc3ccc(CC(=O)O)cc3)c2C1]

39a) 4-Chloro-2-(5-chlorothiophen-2-yl)-6-methyl-6,7-dihydro-5H-cyclopenta[d]pyrimidin 2-(5-Chlorothiophen-2-yl)-6-methyl-6,7-dihydro-5H-cyclopenta[d]pyrimidin-4-ol (326 mg, 1.22 mmol, prepared via base-catalysed condensation reaction of methyl 4-methyl-2-oxocyclopentancarboxylate with 5-chlorothiophen-2-carboximidamide hydrochloride) and phosphoroxychloride (1.14 ml, 12.2 mmol) were stirred for 18 h at room temperature. The reaction mixture was cautiously poured into water and the then extracted with dichloromethane. The combined organic layers were dried over sodium sulfate and evaporated. Yield: 284 mg (81% of theory)

Mass spectroscopy: m/z: [M+H]$^+$=285

39b) Methyl 2-(4-((2-(5-chlorothiophen-2-yl)-6-methyl-6,7-dihydro-5H-cyclopenta[d]pyrimidin-4-yl)oxy)phenyl)acetate The target compound was synthesized in an analogous manner to procedure 7a) from 4-chloro-2-(5-chlorothiophen-2-yl)-6-methyl-6,7-dihydro-5H-cyclopenta[d]pyrimidine (284 mg, 1.00 mmol) and methyl 2-(4-hydroxyphenyl) acetate (248 mg, 1.49 mmol). Yield: 251 mg (61% of theory)

Mass spectroscopy: m/z: [M+H]$^+$=415

39c) 2-(4-((2-(5-Chlorothiophen-2-yl)-6-methyl-6,7-dihydro-5H-cyclopenta[d]pyrimidin-4-yl)oxy)phenyl)acetic acid Preparation of the target compound in an analogous manner to procedure 7b) using the product of 39b) (245 mg, 0.59 mmol). White solid. Yield: 106 mg (45% of theory)

Mass spectroscopy: m/z: [M+H]$^+$=401.0

Unless otherwise specified, the following analytical HPLC methods were used:

Method 1:
Column: Agilent Zorbax Extend, 1.8 μm, 4.6×30 mm
Detection: 254 nm (or 215 nm)
Solvent A: Water/0.1% formic acid
Solvent B: Acetonitrile/0.1% formic acid
Gradient:

| Time in min | % A | % B | Flow rate in ml/min |
| --- | --- | --- | --- |
| 0.0 | 95.0 | 5.0 | 2.5 |
| 3.0 | 5.0 | 95.0 | 2.5 |

-continued

| Time in min | % A | % B | Flow rate in ml/min |
|---|---|---|---|
| 3.01 | 5.0 | 95.0 | 4.5 |
| 3.6 | 5.0 | 95.0 | 4.5 |
| 3.7 | 95.0 | 5.0 | 2.5 |
| 4.0 | 95.0 | 5.0 | 2.5 |

Method 2:
Column: Ascentis Express C18, 2.7 μm, 3 cm×2.1 mm
Detection: MM-ES+APCI+DAD (254 nm)
Solvent A: Water/0.1% formic acid
Solvent B: Methanol/0.1% formic acid
Gradient:

| Time in min | % A | % B | Flow rate in ml/min |
|---|---|---|---|
| 1.0 | 95 | 5 | 0.8 |
| 4.0 | 0 | 100 | 0.8 |
| 5.0 | 0 | 100 | 0.8 |
| 6.0 | 95 | 5 | 0.8 |
| 6.5 | 95 | 5 | 0.8 |

Method 3:
Column: Agilent Zorbax SB-C18, Rapid Resolution HD, 1.8 μm at 80° C.
Detection: time-of-flight mass spectrometer Agilent 6224 at 190-400 nm
Ion source: Dual ESI
Solvent A: Water/0.1% formic acid
Solvent B: $CH_3CN$/0.1% formic acid
Gradient:

| Time in min | % A | % B | Flow rate in ml/min |
|---|---|---|---|
| 0.0 | 98 | 2 | 2.3 |
| 1.0 | 0 | 100 | 2.3 |
| 1.09 | 0 | 100 | 2.3 |
| 1.11 | 98 | 2 | 2.3 |
| 1.3 | 98 | 2 | 2.3 | cAMP HTRF® Assay to Determine the Activity of hPDE4B1

The inhibiting effect of the compounds on the enzyme activity of human PDE4B1 was measured by the quantification of 5'-adenosine monophosphate (5'-AMP), which is formed from 3',5'-adenosine monophosphate (cAMP). Human recombinant enzyme, expressed in Sf9 cells, and the HTRF (homogeneous time-resolved fluorescence) detection method were used in the assay.

The test compound or water (control) was mixed with the human recombinant PDE4B1 enzyme (4.8 U) in a buffer consisting of 44.4 mM tris-HCl, 5.28 mM $MgCl_2$, 2.64 mM DTT and 0.044% Tween 20 (pH 7.8). After adding the cAMP enzyme substrate (final concentration 40 nM) the mixture was incubated for 30 minutes at room temperature. Then a fluorescence acceptor (Dye2 marked with cAMP), a fluorescence donor (anti-cAMP antibody marked with a europium cryptate) and the non-specific phosphodiesterase inhibitor IBMX (3-isobutyl-1-methylxanthine; final concentration 1 mM) were added. After 60 minutes the fluorescence transfer, which correlates with the amount of remaining cAMP, was measured with a microplate reader (Rubystar, BMG) at $\lambda ex=337$ nm, $\lambda em=620$ nm and $\lambda em=665$ nm. The enzyme activity was calculated from the quotient formed from the measured signal at 665 nm and that at 620 nm. The result was expressed as the percentage inhibition of enzyme activity of the control (without PDE4 inhibitor) (literature: N. Saldou et al., Comparison of recombinant human PDE4 isoforms: interaction with substrate and inhibitors, Cell. Signal. Vol. 10, No. 6, 427-440, 1998). The enzyme was omitted for measurement of the basal control.

TABLE 2

(Percentage inhibition of PDE4B at a test substrate concentration of 1 μM):

| Compound no. | Inhibition at 1 μM test concentration [%] |
|---|---|
| 1 | 74 |
| 2 | 75 |
| 3 | 30 |
| 4 | 62 |
| 5 | 71 |
| 6 | 55 |
| 7 | 77 |
| 8 | 84 |
| 9 | 75 |
| 10 | 49 |
| 11 | 44 |
| 12 | 23 |
| 13 | 72 |
| 14 | 68 |
| 15 | 86 |
| 16 | 89 |
| 17 | 95 |
| 18 | 112 |
| 19 | 98 |
| 20 | 103 |
| 21 | 91 |
| 22 | 50 |
| 23 | 18 |
| 24 | 33 |
| 45 | 55 |
| 46 | 76 |
| 47 | 79 |
| 48 | 78 |
| 49 | 59 |
| 50 | 47 |
| 51 | 84 |
| 52 | 53 |
| 53 | 51 |
| 54 | 42 |
| 58 | 65 |
| 59 | 62 |

PDE4B IC50 values below 0.1 μM were measured according to the aforementioned assay for the compound nos.: 7, 15, 16, 17, 18, 19, 20, and 21.

The invention claimed is:
1. A compound of general formula (I):

(I)

in which
G is a phenyl optionally substituted with at least one substituent Z or a 5- or 6-membered heteroaromatic optionally substituted with at least one substituent Z;
Z independently of one another is $(C_1-C_6)$ alkyl, $(C_1-C_6)$ hydroxyalkyl, $(C_1-C_6)$ alkoxy, $(C_1-C_6)$ haloalkyl, $(C_1-C_6)$ haloalkoxy, —$S(C_1-C_6)$ alkyl, halogen, hydroxyl or cyano, wherein aforementioned alkyls are branched or straight-chain and can be substituted;

V is —SO$_2$;

T is oxygen, CH$_2$, CHR$^1$ or CR$^1$R$^2$;

R$^1$ and R$^2$ independently of one another denote (C$_1$-C$_8$) alkyl, (C$_1$-C$_8$) hydroxyalkyl, (C$_1$-C$_8$) haloalkyl and (C$_1$-C$_8$) hydroxyhaloalkyl, wherein the aforementioned alkyl chains are branched or straight-chain and can be substituted, or R$^1$ and R$^2$, together with the carbon atom to which they are bound, form a saturated 3- to 6-membered ring consisting of hydrocarbon groups, optionally substituted with branched or straight-chain (C$_1$-C$_6$) alkyl or hydroxyl groups, which can optionally have one or more heteroatoms;

Q is a phenyl, pyrimidyl, pyrazinyl or pyridyl substituted with a substituent X$^1$ and optionally substituted with at least one substituent X;

X$^1$ is an L-CO$_2$R$^3$ group;

X independently of one another is (C$_1$-C$_6$) alkyl, (C$_3$-C$_6$) cycloalkyl, (C$_1$-C$_6$) alkoxy, (C$_3$-C$_6$) cycloalkoxy, (C$_1$-C$_6$) haloalkyl, (C$_1$-C$_6$) haloalkoxy, halogen, hydroxyl, cyano, carboxyl, —NH$_2$, —NH(C$_1$-C$_6$) alkyl, —N((C$_1$-C$_6$) alkyl)$_2$, N-pyrrolidinyl, N-piperidinyl, N-morpholinyl, —NH—C(O)—(C$_1$-C$_6$) alkyl, —C(O)—NH$_2$, —C(O)—NH(C$_1$-C$_6$) alkyl, —C(O)—N((C$_1$-C$_6$) alkyl)$_2$, —S(O)$_2$—NH$_2$, —S(C$_1$-C$_6$) alkyl, —S(O)—(C$_1$-C$_6$) alkyl, or —S(O)$_2$—(C$_1$-C$_6$) alkyl, wherein the aforementioned alkyl chains are branched or straight-chain and can be substituted;

R$^3$ is hydrogen, branched or straight-chain (C$_1$-C$_6$) alkyl;

L is a bond, (C$_1$-C$_6$) alkylene, (C$_2$-C$_6$) alkenylene, —O—(C$_1$-C$_4$) alkylene, —NH—(C$_1$-C$_4$) alkylene, or —NR$^3$—(C$_1$-C$_4$) alkylene, wherein aforementioned alkylenes or alkenylenes can each be substituted with one or more halogen atoms or wherein aforementioned alkylenes or alkenylenes can be substituted with one or more (C$_1$-C$_6$) alkyl groups, or wherein in aforementioned alkylenes or alkenylenes a CH$_2$ unit can be replaced by an oxygen atom;

n is 1;

K is (C$_1$-C$_6$) alkyl, (C$_1$-C$_6$) alkoxy, (C$_1$-C$_6$) haloalkyl, halogen, hydroxyl or cyano; and m is 0, 1, 2, 3 or 4, as well as pharmacologically tolerable salts, diastereomers, enantiomers, racemates or solvates thereof.

2. The compound according to claim 1, wherein

Z independently of one another is CH$_3$, OCH$_3$, CF$_3$, CHF$_2$, CH$_2$F, OCF$_3$, OCHF$_2$, OCH$_2$F, SCH$_3$, Cl, F, OH or CN;

R$^1$ and R$^2$ independently of one another denote (C$_1$-C$_4$) alkyl, (C$_1$-C$_4$) hydroxyalkyl, (C$_1$-C$_4$) haloalkyl; (C$_1$-C$_4$) hydroxyhaloalkyl;

X$^1$ is an L-CO$_2$R$^3$ group;

R$^3$ is hydrogen or a branched or straight-chain (C$_1$-C$_4$) alkyl;

L is a bond or methylene, wherein the methylene can be substituted with one or two halogen atoms; and K is (C$_1$-C$_4$) alkyl, (C$_1$-C$_4$) alkoxy, (C$_1$-C$_4$) haloalkyl, fluorine, chlorine, bromine, hydroxyl or cyano.

3. The compound according to claim 1, wherein

G is a phenyl optionally substituted with at least one substituent Z, a thiazolyl optionally substituted with at least one substituent Z or a thienyl optionally substituted with at least one substituent Z.

4. The compound according to claim 1, wherein

G is a phenyl optionally substituted with at least one substituent Z or a 5- or 6-membered heteroaromatic optionally substituted with at least one substituent Z, which are selected from the following groups:

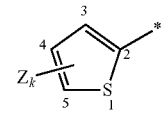
G1

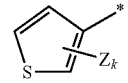
G2

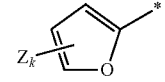
G3

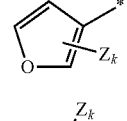
G4

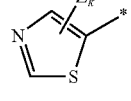
G6

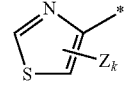
G7

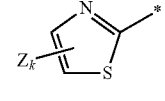
G8

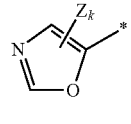
G9

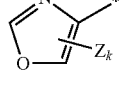
G10

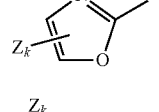
G11

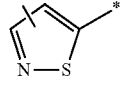
G12

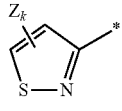
G13

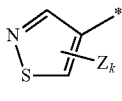
G14

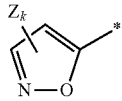
G15

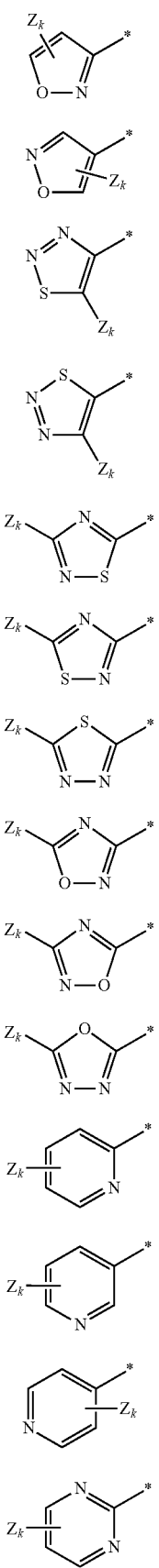
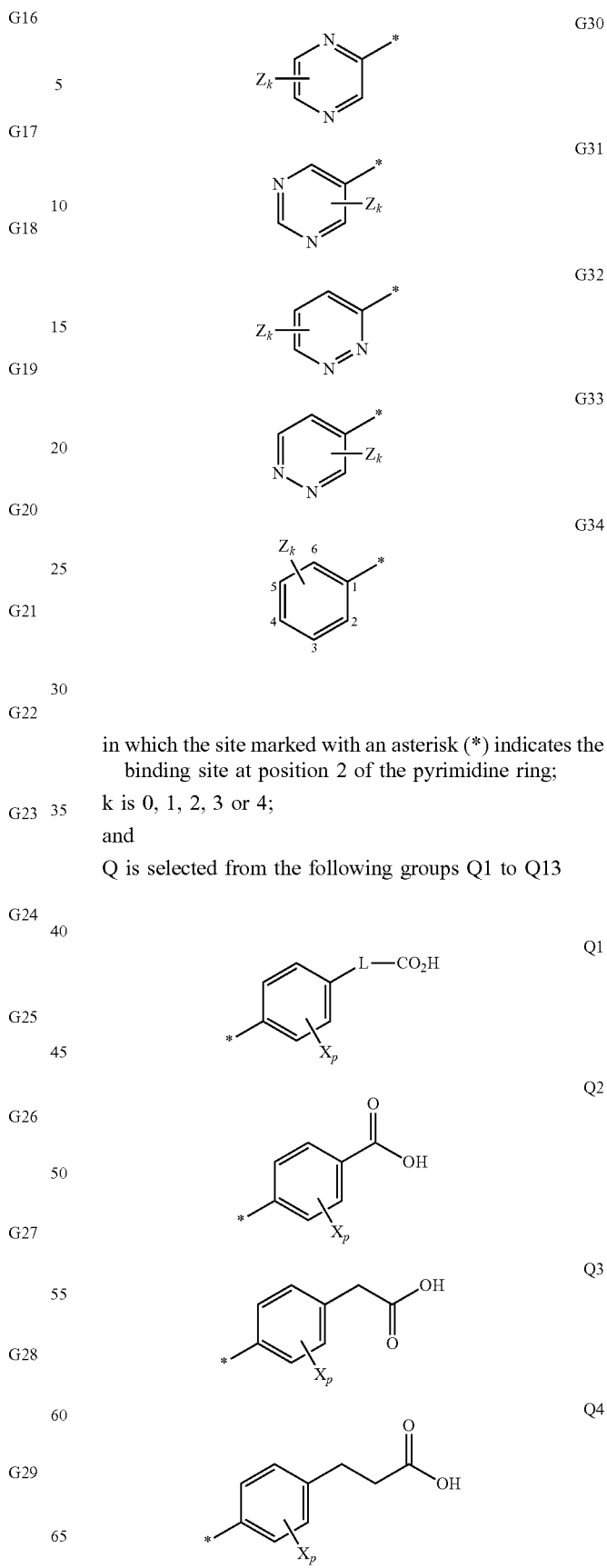
in which the site marked with an asterisk (*) indicates the binding site at position 2 of the pyrimidine ring;
k is 0, 1, 2, 3 or 4;
and
Q is selected from the following groups Q1 to Q13

Q5 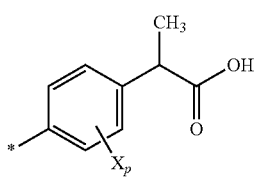

Q6 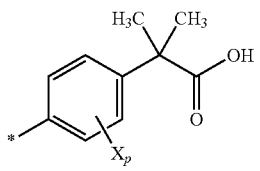

Q7 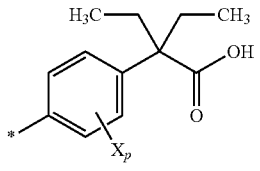

Q8 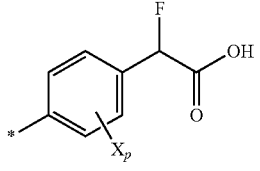

Q9 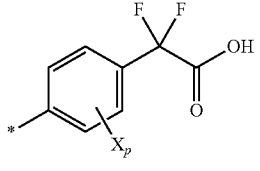

Q10 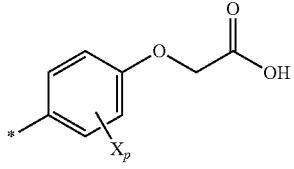

Q11 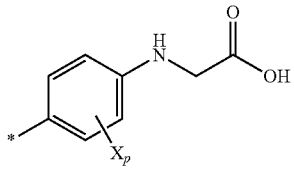

Q12 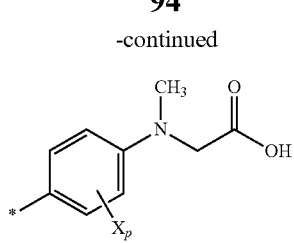

Q13 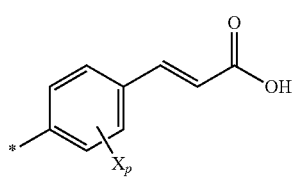

in which the site marked with an asterisk (*) indicates the binding site at group T and p is 0, 1, 2, 3 or 4;

X independently of one another is $(C_1-C_6)$ alkyl, $(C_3-C_6)$ cycloalkyl, $(C_1-C_6)$ alkoxy, $(C_3-C_6)$ cycloalkoxy, $(C_1-C_6)$ haloalkyl, $(C_1-C_6)$ haloalkoxy, halogen, hydroxyl, cyano, carboxyl, —$NH_2$, —$NH(C_1-C_6)$ alkyl, —$N((C_1-C_6)$ alkyl$)_2$, N-pyrrolidinyl, N-piperidinyl, N-morpholinyl, —NH—C(O)—$(C_1-C_6)$ alkyl, —C(O)—$NH_2$, —C(O)—$NH(C_1-C_6)$ alkyl, —C(O)—$N((C_1-C_6)$ alkyl$)_2$, —$S(O)_2$—$NH_2$, —$S(C_1-C_6)$ alkyl, —S(O)—$(C_1-C_6)$ alkyl, or —$S(O)_2$—$(C_1-C_6)$ alkyl, wherein the aforementioned alkyl chains are branched or straight-chain and can be substituted;

L is a bond or methylene, wherein the methylene can be substituted with one or two halogen atoms.

5. The compound according to claim 1, wherein T is oxygen.

6. The compound according to claim 1, wherein T is $CH_2$.

7. The compound according to claim 4, wherein

G is a chemical grouping G1, G2, G6, G7, G8, G12, G13 or G34, optionally substituted with at least one substituent Z; and Q is a chemical grouping Q2 or Q3.

8. A pharmaceutical composition comprising at least one compound as defined in claim 1 and one or more pharmaceutical auxiliary substances.

* * * * *